(12) United States Patent
Soejima et al.

(10) Patent No.: US 10,329,604 B2
(45) Date of Patent: Jun. 25, 2019

(54) METHOD AND KIT FOR DETECTION OF MICROORGANISM

(71) Applicant: Morinaga Milk Industry Co., Ltd., Minato-ku, Tokyo (JP)

(72) Inventors: Takashi Soejima, Zama (JP); Frank Schlitt-Dittrich, Zama (JP)

(73) Assignee: Morinaga Milk Industry Co., Ltd., Tokyo (JP)

(*) Notice: Subject to any disclaimer, the term of this patent is extended or adjusted under 35 U.S.C. 154(b) by 232 days.

(21) Appl. No.: 15/188,755

(22) Filed: Jun. 21, 2016

(65) Prior Publication Data

US 2016/0298181 A1     Oct. 13, 2016

Related U.S. Application Data

(62) Division of application No. 13/386,601, filed as application No. PCT/JP2010/062474 on Jul. 23, 2010, now Pat. No. 9,394,572.

(30) Foreign Application Priority Data

Jul. 24, 2009 (JP) .................................. 2009-173566

(51) Int. Cl.
    C12Q 1/68      (2018.01)
    C12Q 1/6848    (2018.01)
    C12Q 1/689     (2018.01)

(52) U.S. Cl.
    CPC .......... *C12Q 1/6848* (2013.01); *C12Q 1/689* (2013.01)

(58) Field of Classification Search
    None
    See application file for complete search history.

(56) References Cited

U.S. PATENT DOCUMENTS

2009/0093008 A1   4/2009 Yoshida et al.

FOREIGN PATENT DOCUMENTS

| EP | 2077334 | 7/2009 | |
| EP | 2077334 A1 * | 7/2009 | ............... C12Q 1/68 |
| JP | 2001-008685 | 1/2001 | |
| WO | WO 01/77379 | 10/2001 | |
| WO | WO 02/052034 | 7/2002 | |
| WO | WO 2004/104196 | 12/2004 | |
| WO | WO 2007/094077 | 8/2007 | |
| WO | WO 2009/022558 | 2/2009 | |

OTHER PUBLICATIONS

Examination report issued in corresponding Indian Patent Application No. 1571/CHENP/2012, dated Feb. 24, 2017, in 9 pages.
Al-Soud, et al. "Effects of Amplification Facilitators on Diagnostic PCR in the Presence of Blood, Feces and Meat," Journal of Clinical Microbiology, vol. 38, No. 12, pp. 4463-4470, Dec. 2000.
Benson et al., "Detection of Helicobacter pylori in water by direct PCR," Letters in Applied Microbiology, vol. 39, pp. 221-225 (2004).
Bickley, et al. "Polymerase Chain Reaction (PCR) Detection of Listeria monocytogenes in Diluted Milk and Reversal of PCR Inhibition Caused by Calcium Ions," Letters in Applied Microbiology, vol. 22, pp. 153-158, 1996.
Delgado-Viscogliosi et al., "Viability PCR, a Culture-Independent Method for Rapid and Selective Quantification of Viable Legionella pneumophila Cells in Environmental Water Samples," Applied and Environmental Microbiology, vol. 75(11), pp. 3502-3512 (2009).
Extended European Search Report issued in European Patent Application No. 10802360.7 dated Jan. 7, 2013.
Fode-Vaughan, et al. "Detection of Bacteria in Environmental Samples by Direct PCR without DNA Extraction," BioTechniques, vol. 31, No. 3, pp. 598-607, 2001.
Forbes, et al. "Substances Interfering with Direct Detection of *Mycobacterium tuberculosis* in Clinical Specimens by PCR: Effects of Bovine Serum Albumin," Journal of Clinical Microbiology, vol. 34, No. 9, pp. 2125-2128, Sep. 1996.
Hodson et al., "In Situ PCR for Visualization of Microscale Distribution of Specific Genes and Gene Products in Prokaryotic Communities," Applied and Environmental Microbiology, vol. 61(11), pp. 4074-4082 (1995).
International Search Report dated Sep. 21, 2010 issued to priority international application PCT/JP2010/062474.
Kreader, "Relief of Amplification Inhibition in PCR with Bovine Serum Albumin or T4 Gene 32 Protein," Applied and Environmental Microbiology, vol. 62, No. 3, pp. 1102-1106, Mar. 1996.
Layton et al., "Development of Bacteroides 16S rRNA Gene TaqMan-Based Real-Time PCR Assays for Estimation of Total, Human, and Bovine Fecal Pollution in Water," Applied and Environmental Microbiology, vol. 72(6), pp. 4214-4224 (2006).
Nogva et al. (Biotechniques, 2003, 34(4):804-8,10,12-13).

(Continued)

*Primary Examiner* — Stephanie K Mummert
(74) *Attorney, Agent, or Firm* — Knobbe, Martens, Olson & Bear, LLP

(57) ABSTRACT

A kit for detecting live cells of a microorganism in a test sample by distinguishing the live cells from dead cells or injured cells by a nucleic acid amplification method includes the following components:
1) an agent capable of covalently binding to DNA or RNA of the microorganism by irradiation with light having a wavelength of 350 nm to 700 nm;
2) an agent for suppressing a nucleic acid amplification inhibitory substance; and
3) a primer or primers for amplifying a target region of the DNA or RNA of the microorganism to be detected by a nucleic acid amplification method. The agent for suppressing a nucleic acid amplification inhibitory substance is one or more selected from albumin, dextran, T4 gene 32 protein, acetamide, betaine, dimethyl sulfoxide, formamide, glycerol, polyethylene glycol, soybean trypsin inhibitor, $\alpha 2$-macroglobulin, tetramethylammonium chloride, lysozyme, phosphorylase and lactate dehydrogenase.

9 Claims, 17 Drawing Sheets

Specification includes a Sequence Listing.

(56) References Cited

OTHER PUBLICATIONS

Notification of First Office Action dated Aug. 31, 2012, issued to corresponding Chinese application No. 201080033156.X.
Rudi, et al. "Detection of Viable and Dead Listeria monocytogenes on Gouda-like Cheeses by Real-time PCR," Letters in Applied Microbiology, vol. 40, pp. 301-306, 2005.
Soejima, "A Method to Detect Only Live Bacteria During PCR Amplification," Bioindustry, vol. 25, No. 9, pp. 85-93, 2008.
Soejima, et al. "Method to Detect Only Live Bacteria during PCR Amplification," Journal of Clinical Microbiology, vol. 46, No. 7, pp. 2305-2313, Jul. 2008.
Soejima et al., "Rapid detection of viable bacteria by nested polymerase chain reaction via long DNA amplification after ethidium monoazide treatment," Analytical Biochemistry, vol. 418, pp. 286-294 (2011).
Wilson, "Inhibition and Facilitation of Nucleic Acid Amplification," Applied and Environmental Microbiology, vol. 63(10), pp. 3741-3751 (1997).

\* cited by examiner

Fig.3

Fluorescence microscopy images (SYTO9)

Superposed images of the stereoscopic microscopy images and fluorescence microscopy images Stereoscopic microscopy images Fluorescence microscopy images (SYTO9)

Superposed images

Stereoscopic microscopy images

Superposed images

Fluorescence microscopy images (SYTO9)

Stereoscopic microscopy images

Fluorescence microscopy images (SYTO9)

Superposed images

Stereoscopic microscopy images

Superposed images

Fluorescence microscopy images (SYTO9)

Stereoscopic microscopy images

Superposed images

Fluorescence microscopy images (SYTO9)

Stereoscopic microscopy images

Fluorescence microscopy images (SYTO9)

Stereoscopic microscopy images

Superposed images

Fluorescence microscopy images (SYTO9)

Superposed images

Stereoscopic microscopy images

METHOD AND KIT FOR DETECTION OF MICROORGANISM

CROSS-REFERENCE TO RELATED APPLICATIONS

This application is a divisional of U.S. application Ser. No. 13/386,601, filed Jan. 23, 2012 which is the U.S. National Phase under 35 U.S.C. § 371 of International Application PCT/JP2010/062474, filed Jul. 23, 2010, which was published in a non-English language, which claims priority to JP Application No.: 2009-173566, filed Jul. 24, 2009.

TECHNICAL FIELD

The present invention relates to a method and kit for detecting a microorganism contained in a foodstuff, a biological sample and an environmental sample such as industrial water and tap water. More precisely, the present invention relates to a method and kit for detection of a microorganism that enable selective detection of live cells of a microorganism contained in a foodstuff, a biological sample, a swab sample, and an environmental sample such as industrial water and tap water.

BACKGROUND ART

The plate culture method has been conventionally used for measurement of total live bacterial counts in foodstuffs, biological samples, swab samples, or environmental samples. However, the plate culture method requires time of about two days to one month to obtain a result.

Because of the improvements of sterilization techniques and processing techniques for foodstuffs, needs for distinguishing live states of microorganisms from dead states of microorganisms existing in test samples are increasing even for the cases where the cells exist in an extremely small amount. In the fields of food sanitation inspection and clinical test, in particular, as a quick method for detecting bacteria, it is attempted to determine presence or absence of bacteria or quantify bacteria by amplifying genes specific to the bacteria by PCR to such an amount that the genes can be visually observed. However, if a bacterial DNA is targeted, the background of dead cells originally contained in the test sample is also detected, and therefore a positive result obtained by PCR does not necessarily suggest the presence of live bacteria. Therefore, the current situation in the fields of food sanitation and clinical test is that PCR is not used widely, although it is a highly sensitive and quick technique.

In these days, it is attempted to detect and quantify only live cells of microorganism in a test sample by preparing cDNA with reverse transcriptase for mRNA as a target and performing PCR with primers specific to various bacteria. However, in this method, the reverse transcription of mRNA of dead cells itself is not inhibited, and when $10^4$ cfu/ml or $10^4$ cfu/g or more of dead cells are contained in the test sample, background of the dead cells is detected. Therefore, this method cannot be said to be sufficient as a method for determining the live and dead states.

Specifically, as a method for distinguishing live state from dead states of microorganisms such as bacteria using the PCR method, the methods described in Patent document 1 and 2 have been disclosed. However, the following problems remain in these methods for distinguishing live and dead states of microorganisms such as bacteria using the PCR method.

As for the technique disclosed in Patent document 1, examples are mentioned for distinction of dead cells contained in boiled foodstuffs subjected to high temperature long time sterilization at 100° C. for 10 to 30 minutes, and microorganisms contained in foodstuffs subjected to ethanol sterilization or formaldehyde sterilization. However, especially the treatment of the latter type, there are not foodstuffs actually subjected to such pasteurization treatments. Moreover, there are not supposed detection of only live microorganisms in foodstuffs subjected to the currently major sterilization method in the food industry, low temperature long time pasteurization (LILT pasteurization), high temperature short time pasteurization (HTST pasteurization), or ultra high temperature pasteurization (UHT pasteurization), and detection of only live specific pathogenic bacteria in clinical specimens of infectious disease patients administered with antibiotics. Moreover, in the case of a test sample of a foodstuff or clinical specimen containing dead cells background at a concentration of $10^4$ cfu/ml or higher, the amounts of the final PCR amplified products derived from dead cells exceed the detection limit of the technique of Patent document 1, and therefore it is impossible to determine whether a positive response of a test sample obtained by PCR is derived from live cells or dead cells.

Further, as the technique of Patent document 2, disclosed is a method of distinguishing live cells from dead cells by utilizing relative decrease in RNA/DNA molar ratio of dead cells compared with that of live cells. In this method, the total RNA is extracted, complementary DNA is prepared by using a reverse transcription reaction, then PCR is performed to calculate the Ct value thereof, and the molar concentration of RNA is obtained by using a separately prepared calibration curve. Separately, a region of chromosomal DNA corresponding to that RNA is amplified by PCR to obtain the Ct value thereof, and the molar concentration of the chromosomal DNA is calculated on the basis of the calibration curve to obtain the RNA/DNA molar ratio. That is, the above procedure requires to perform troublesome extraction of total RNA and uses two steps of reverse transcription reaction and PCR. Therefore, this technique is inferior to usual PCR targeting DNA in quantification performance and quickness. Further, RNA is continuously produced in live cells, whereas RNA derived from dead cells is decomposed over time at an early stage. Therefore, the technique lacks stability. Furthermore, in a foodstuff or clinical specimen containing dead cells at a high concentration, only live cells of $\frac{1}{10}$ of that concentration can be detected by this technique. Therefore, it is difficult to apply this technique in the fields of food sanitation inspection and clinical test, which require quickness, high sensitivity and accuracy.

A method for selectively detecting live cells (Viable-and-Culturable cells) of a microorganism by distinguishing them from dead cells or injured cells (Viable-but-Non Culturable cells (VNC cells)) is disclosed in Patent document 3. The method disclosed in Patent document 3 is a method comprising the step of treating a test sample with a topoisomerase poison and/or a DNA gyrase poison, the step of extracting DNA from the test sample, and amplifying a target region of the extracted DNA by PCR, and the step of analyzing an amplified product, and as the topoisomerase poison or the DNA gyrase poison, ethidium monoazide is exemplified.

A method in which ethidium monoazide is used is also disclosed in Non-patent document 1. This method is a detection method comprising the step of adding ethidium monoazide to a test sample and irradiating the sample with light, the step of extracting DNA from the sample after the irradiation, and the step of amplifying a specific region by PCR using the extracted DNA as a template. Moreover, a technique of semi-quantitatively quantifying live cells count by a combination of culture of a microorganism and real-time PCR is disclosed in Non-patent document 1.

Moreover, as a method for still more clearly distinguishing live cells and injured cells of a microorganism, the method described in Patent document 4 is disclosed. This method is a method comprising the step of adding a cross-linker capable of cross-linking a DNA by irradiation with light having a wavelength of 350 nm to 700 nm to a test sample, the step of irradiating the test sample to which the cross-linker is added with light having a wavelength of 350 nm to 700 nm, the step of removing the cross-linker contained in the test sample irradiated with light, the step of adding a medium to the test sample from which the cross-linker is removed and incubating the test sample, the step of adding again the cross-linker capable of cross-linking a DNA by irradiation with light having a wavelength of 350 nm to 700 nm to the incubated test sample, the step of irradiating the test sample to which the cross-linker is added with light having a wavelength of 350 nm to 700 nm, the step of extracting a DNA from the test sample and amplifying a target region of the extracted DNA by a nucleic acid amplification method, and the step of analyzing the amplified product.

Meanwhile, there is suggested a possibility that, in amplification of nucleic acid by PCR, albumin may suppress inhibition activity of a PCR inhibitor, or promote the reactions of PCR (Non-patent document 2). Moreover, it is also suggested that calcium inhibits the reactions of PCR, but the inhibition of PCR by calcium can be made tolerable by addition of magnesium ions (Non-patent document 3).

Moreover, there is disclosed a method of performing reactions of PCR using a bacterial DNA as a template, in which the reactions of PCR are performed without extracting the DNA from the bacterium (Non-patent document 4, Patent document 5). In Patent document 5, there is disclosed that random PCR is performed in a bacterium in the DNA fingerprinting method, and phosphates and dodecylsulfates are mentioned as components of the buffer composition for nucleic acid synthesis.

PRIOR ART REFERENCES

Patent Documents

Patent document 1: Domestic Laid-Open Publication of a Japanese translation of PCT Application (KOHYO) No. 2003-530118
Patent document 2: International Patent Publication WO2002/052034
Patent document 3: International Patent Publication WO2007/094077
Patent document 4: International Patent Publication WO2009/022558
Patent document 5: International Patent Publication WO2004/104196

Non-Patent Documents

Non-patent document 1: Rudi, K., et al., Letters in Applied Microbiology, 2005, Vol. 40, pp. 301-306
Non-patent document 2: Forbes, B. E., et al., Journal of Clinical Microbiology, 1996, 34 (9), pp. 2125-2128
Non-patent document 3: Bickley, J., et al., Letter in Applied Microbiology, 1996, 22, pp. 153-158
Non-patent document 4: Kimberly, A., et al., BioTechniques, 31, 2001, pp. 598-607

DISCLOSURE OF THE INVENTION

Problems to be Resolved by the Invention

By the aforementioned method using a topoisomerase poison and/or a DNA gyrase poison, or a cross-linker, live cells of microorganism, especially live cells of *Klebsiella, Citrobacter, Listeria, Salmonella* bacteria and so forth can be selectively detected with high sensitivity. However, a further improved method, especially a method for highly sensitively or highly accurately detecting live cells of *Escherichia* or *Salmonella* bacteria has been desired.

An object of the present invention is to provide a novel method for more selectively detecting live cells of a microorganism contained in a foodstuff or biological sample compared with dead cells or injured cells of the microorganism, and a kit for performing such a method.

Means of Solving the Problems

The inventors of the present invention have made extensive studies on a method of discriminating between life and death of microorganisms, which is applicable to various sterilization methods and is suitable for food sanitation inspections of high detection sensitivity, and on a method of detecting a specific pathogen in a patient with an infection in hospital or clinical practice. As a result, the inventors have found out that the distinction can be attained with high sensitivity by adding an agent capable of covalently binding to DNA or RNA by irradiation with light having a wavelength of 350 nm to 700 nm to a test sample; irradiating the test sample with light having a wavelength of 350 nm to 700 nm; adding an agent for suppressing an action of a nucleic acid amplification inhibitory substance, a magnesium salt, and an organic acid salt or a phosphoric acid salt, and amplifying a chromosomal DNA of a microorganism flowing out of cells by a nucleic acid amplification reaction. Thus, the present invention has been completed.

That is, the present invention provides a method for detecting live cells of a microorganism in a test sample by distinguishing the live cells from dead cells or injured cells, which comprises the steps of:

a) adding an agent capable of covalently binding to a DNA or RNA by irradiation with light having a wavelength of 350 nm to 700 nm to the test sample;

b) irradiating the test sample to which the agent is added with light having a wavelength of 350 nm to 700 nm;

c) amplifying a target region of the DNA or RNA of the microorganism contained in the test sample by a nucleic acid amplification method in the presence of an agent for suppressing an action of a nucleic acid amplification inhibitory substance, without extracting nucleic acids from the cells; and d) analyzing the amplified product.

In a preferred embodiment of the present invention, the amplification of the target region is performed in microbial cells.

In a preferred embodiment of the aforementioned method, in the aforementioned step c), the amplification of the target region is performed in the presence of one or more kinds selected from a surfactant, a magnesium salt, and an organic acid salt or a phosphoric acid salt.

In a preferred embodiment of the aforementioned method, before the aforementioned step c), the steps a) and b) are repeatedly performed.

In a preferred embodiment of the aforementioned method, before the aforementioned step a), the following step e) is performed:

e) treating the test sample with an enzyme having an activity of decomposing cells other than that of microorganism, a colloidal particle of a protein, a lipid, or a saccharide existing in the test sample.

In a preferred embodiment of the aforementioned method, the enzyme is selected from a protease, a lipid-degrading enzyme and a saccharide-degrading enzyme.

In a preferred embodiment of the aforementioned method, the test sample is any one of a foodstuff, a biological sample, drinking water, industrial water, environmental water, wastewater, soil and a swab sample.

In a preferred embodiment of the aforementioned method, the microorganism is a bacterium or a virus.

In a preferred embodiment of the aforementioned method, the bacterium is a gram-negative bacterium.

In a preferred embodiment of the aforementioned method, the agent capable of covalently binding to a DNA or RNA by irradiation with light having a wavelength of 350 nm to 700 nm is selected from ethidium monoazide, ethidium diazide, propidium monoazide, psoralenpsoralen, 4,5',8-trimethylpsoralen, and 8-methoxypsoralenpsoralen.

In a preferred embodiment of the aforementioned method, the agent for suppressing an action of a nucleic acid amplification inhibitory substance consists of one or more kinds selected from albumin, dextran, T4 gene 32 protein, acetamide, betaine, dimethyl sulfoxide, formamide, glycerol, polyethylene glycol, soybean trypsin inhibitor, α2-macroglobulin, tetramethylammonium chloride, lysozyme, phosphorylase, and lactate dehydrogenase.

In a preferred embodiment of the aforementioned method, the organic acid salt is selected from an acetic acid salt, a propionic acid salt and a citric acid salt.

In a preferred embodiment of the aforementioned method, the phosphoric acid salt is a pyrophosphoric acid salt.

In a preferred embodiment of the aforementioned method, the target region is a target region of 50 to 5,000 nucleotides.

In a preferred embodiment of the aforementioned method, the target region is a target region corresponding to a gene selected from 5S rRNA gene, 16S rRNA gene, 23S rRNA gene, and tRNA gene of the DNA of the test sample.

In a preferred embodiment of the aforementioned method, the nucleic acid amplification method is PCR, LAMP, SDA, LCR, TMA, TRC, HC, or the microarray method.

In a preferred embodiment of the aforementioned method, PCR is performed as real-time PCR to simultaneously conduct PCR and analysis of the amplified product.

In a preferred embodiment of the aforementioned method, the analysis of the amplified product is performed by using a standard curve representing relationship between amount of the microorganism and the amplified product and created by using standard samples of the microorganism.

As the kit of the present invention, there is provided a kit for detecting live cells of a microorganism in a test sample by distinguishing the live cells from dead cells or injured cells by a nucleic acid amplification method, which comprises the following components:

1) an agent capable of covalently binding to a DNA or RNA by irradiation with light having a wavelength of 350 nm to 700 nm;

2) an agent for suppressing an action of a nucleic acid amplification inhibitory substance; and 3) a primer or primers for amplifying a target region of a DNA or RNA of the microorganism to be detected by a nucleic acid amplification method.

In a preferred embodiment of the aforementioned kit, the kit further comprises one or more kinds selected from a surfactant, a magnesium salt, and an organic acid salt or a phosphoric acid salt.

In a preferred embodiment of the aforementioned kit, the kit further comprises an enzyme having an activity of decomposing cells other than that of microorganism, a colloidal particle of a protein, a lipid, or a saccharide existing in the test sample.

In a preferred embodiment of the aforementioned kit, the nucleic acid amplification method is PCR, RT-PCR, LAMP, SDA, LCR, TMA, TRC, HC, or the microarray method.

In a preferred embodiment of the aforementioned kit, the agent capable of covalently binding to a DNA or RNA by irradiation with light having a wavelength of 350 nm to 700 nm is selected from ethidium monoazide, ethidium diazide, propidium monoazide, psoralen, 4,5',8-trimethylpsoralen, and 8-methoxypsoralen.

In a preferred embodiment of the aforementioned kit, the agent for suppressing an action of a nucleic acid amplification inhibitory substance consists of one or more kinds selected from albumin, dextran, T4 gene 32 protein, acetamide, betaine, dimethyl sulfoxide, formamide, glycerol, polyethylene glycol, soybean trypsin inhibitor, α2-macroglobulin, tetramethylammonium chloride, lysozyme, phosphorylase, and lactate dehydrogenase.

In a preferred embodiment of the aforementioned kit, the organic acid salt is selected from an acetic acid salt, a propionic acid salt and a citric acid salt.

In a preferred embodiment of the aforementioned kit, the phosphoric acid salt is a pyrophosphoric acid salt.

In a preferred embodiment of the aforementioned kit, the enzyme is selected from a protease, a lipid-degrading enzyme and a saccharide-degrading enzyme.

MODES FOR CARRYING OUT THE INVENTION

Figure 1:
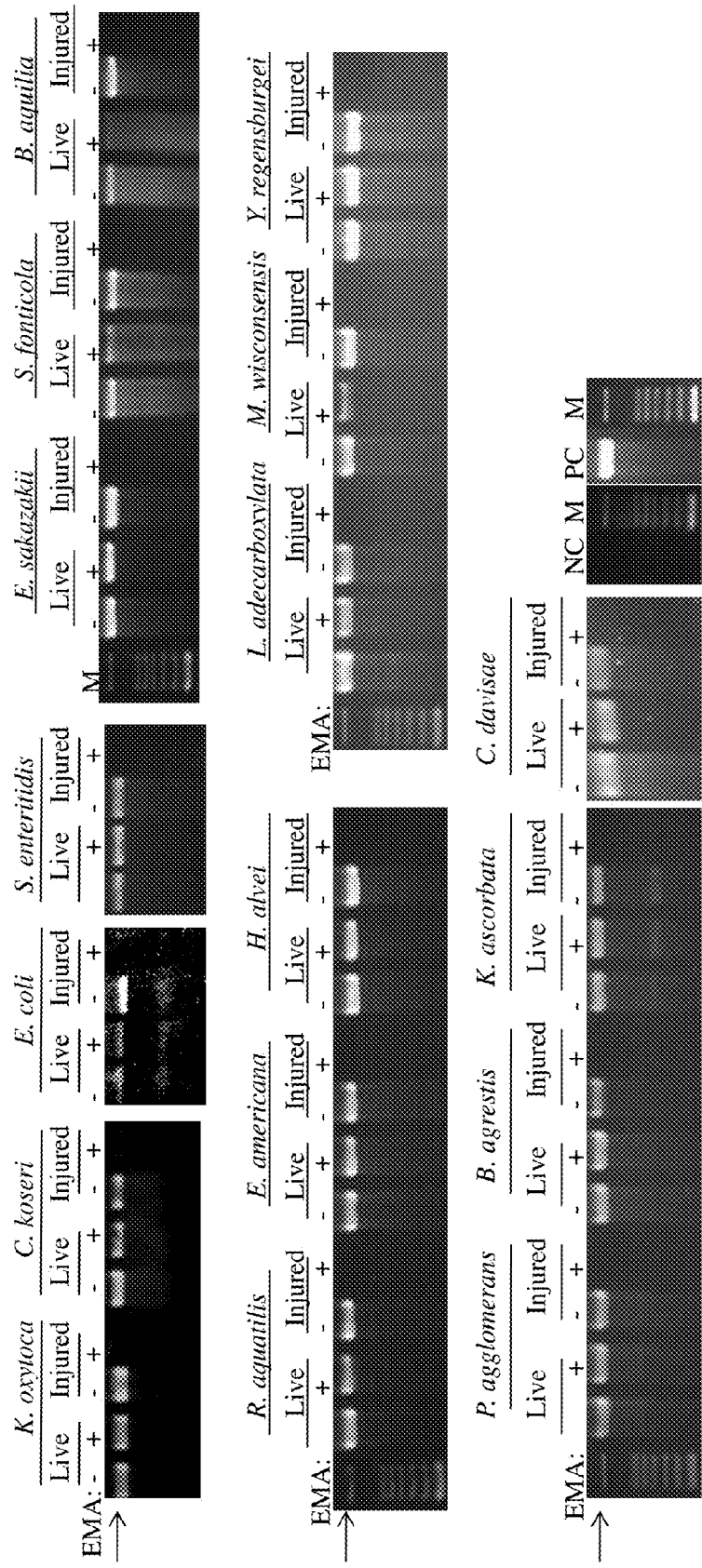
FIG. 1 Electrophoresis photographs of PCR amplified products obtained in the method of the present invention "Live" represents live cells, "Injured" represents injured cells FIG. 2 Electrophoresis photographs showing results of detection of live cells of microorganisms performed by the method of the present invention FIG. 3 Electrophoresis photographs showing results of detection of live cells of microorganisms performed by a conventional method "Live" represents live cells, "Injured" represents injured cells FIG. 4 Fluorescence microphotograph and stereoscopic microphotograph of a not-heated physiological saline suspension of *Enterobacter sakazakii* bacterium FIG. 5 Fluorescence microphotograph and stereoscopic microphotograph of a supernatant of a not-heated physiological saline suspension of *Enterobacter sakazakii* bacterium FIG. 6 Fluorescence microphotograph and stereoscopic microphotograph of a physiological saline suspension of *Enterobacter sakazakii* bacterium after repetition of thermal cycles FIG. 7 Fluorescence microphotograph and stereoscopic microphotograph of a supernatant of a physiological saline suspension of *Enterobacter sakazakii* bacterium after repetition of thermal cycles FIG. 8 Fluorescence microphotograph and stereoscopic microphotograph of *Enterobacter sakazakii* bacterium suspended in a not-heated pretreatment agent solution FIG. 9 Fluorescence microphotograph and stereoscopic microphotograph of a supernatant of *Enterobacter sakazakii* bacterium suspended in a not-heated pretreatment agent solution FIG. 10 Fluorescence microphotograph and stereoscopic microphotograph of *Enterobacter sakazakii* bacterium suspended in a pretreatment agent solution after repetition of thermal cycles FIG. 11 Fluorescence microphotograph and stereoscopic microphotograph of a supernatant of *Enterobacter sakazakii* bacterium suspended in a pretreatment agent solution after repetition of thermal cycles FIG. 12 Drawings showing results of flow cytometry of physiological saline suspensions of the *Enterobacter sakazakii* bacterium or supernatants thereof in a non-heated state or after repetition of thermal cycles FIG. 13 Drawings showing results of flow cytometry of the *Enterobacter sakazakii* bacterium suspended in a pretreatment agent solution or supernatants thereof in a non-heated state or after repetition of thermal cycles FIG. 14 An electrophoresis photograph of the 16S-23S rRNA gene amplified product, obtained in the method of the present invention using the *Enterobacter sakazakii* bacterium treated with various fixation solutions. Ct values are indicated as average and SD, and SD is indicated in parentheses
L: 100-bp DNA ladder
A: Fixation solution A
B: Fixation solution B
C: Fixation solution C
S: No fixation FIG. 15 An electrophoresis photograph of the ompA gene amplified product, obtained in the method of the present invention using the *Enterobacter sakazakii* bacterium treated with various fixation solutions. Ct values are indicated as average and SD, and SD is indicated in parentheses
A: Fixation solution A
B: Fixation solution B
L: 100-bp DNA ladder FIG. 16 Electrophoresis photographs obtained before and after PCR (16S-23S rRNA gene amplification reaction) by using the *Enterobacter sakazakii* bacterium
Lanes 2 and 3: supernatant of PCR reaction mixture
Lanes 5 and 6: DNAs extracted from the pellet washed twice by the centrifugation after PCR reaction
Lanes 7 and 8: DNAs directly extracted from the cells
Lanes 9 and 10: DNAs extracted from the cells actually used in the test just before PCR
Lanes 13 and 14: DNAs extracted from the cells washed after addition of the PCR product
L: 100-bp DNA ladder
B: Fixation solution B
S: No fixation FIG. 17 Electrophoresis photographs of suspensions of the *Enterobacter sakazakii* bacterium subjected to a heat treatment in the presence of physiological saline or pretreatment agent, and centrifugation supernatants thereof
L: 100-bp DNA ladder

Hereinafter, preferred embodiments of the present invention are described in detail. However, the present invention is not limited to the following preferred embodiments and may be freely modified within the scope of the present invention. The percentage in the present description is expressed as a percentage by mass unless otherwise specified.

A target to be detected by the method of the present invention includes all kinds of nucleic acids, specifically, single-stranded DNA, double-stranded DNA, single-stranded RNA, and double-stranded RNA, as long as the target can be amplified eventually. Of those, the detection target is preferably DNA, particularly preferably double-stranded DNA.

<1> Method of the Present Invention

The method of the present invention is a method for detecting live cells of a microorganism in a test sample by distinguishing the live cells from dead cells or injured cells, which comprises the steps of:

a) adding an agent capable of covalently binding to a DNA or RNA by irradiation with light having a wavelength of 350 nm to 700 nm to the test sample;

b) irradiating the test sample to which the agent is added with light having a wavelength of 350 nm to 700 nm;

c) amplifying a target region of the DNA or RNA of the microorganism contained in the test sample by a nucleic acid amplification method in the presence of an agent for suppressing an action of a nucleic acid amplification inhibitory substance, without extracting nucleic acids from the cells; and d) analyzing the amplified product.

In the specification of the present invention, the term "test sample" refers to an object containing live cells of microorganism to be detected. The test sample is not particularly limited as long as the presence of the microorganism can be detected by amplification of a specific region of chromosomal DNA or RNA by a nucleic acid amplification method. Preferred examples thereof include foodstuffs, biological samples, drinking water, industrial water, environmental water, wastewater, soil, swab samples, and so forth.

In particular, preferred examples of the foodstuffs include: drinks such as soft drinks, carbonated soft drinks, supplement drinks, fruit juice drinks, and *lactobacillus* drinks (including concentrates and powders of these drinks); ice confectionery products such as ice creams, ice sherbets, and shaved ice; dairy products such as processed milk, milk drinks, fermented milk, and butter; enteral foods, fluid diets, milk for infant, sports drinks; functional foods such as foods for specified health use and dietary supplements, and so forth.

Examples of the biological samples include blood samples, urine samples, cerebrospinal fluid samples, synovial fluid samples, pleural effusion samples, sputum samples, feces samples, nasal cavity mucosa samples, laryngeal mucosa samples, gastric lavage solution samples, pus samples, skin mucus membrane samples, oral cavity mucosa samples, respiratory organ mucus membrane samples, digestive organ mucus membrane samples, eye conjunctiva samples, placenta samples, reproductive cell samples, parturient canal samples, mother's milk samples, saliva samples, vomits, contents of bulla and so forth.

Examples of the environmental water include tap water, groundwater, river water, rainwater, and so forth.

In the present invention, the test sample may be any of such foodstuffs, biological samples, drinking water, industrial water, environmental water, wastewater, soil, swab samples as mentioned above, etc. themselves or may be any of diluted or concentrated products thereof or any of products obtained by a pretreatment other than the method of the present invention. Examples of the pretreatment include heat treatment, filtration, centrifugation, and so forth.

Further, foreign substances such as cells other than microorganisms, protein colloidal particles, lipids, saccharides and so forth in the test sample may be removed or reduced by a treatment with an enzyme having an activity for degrading them or the like. In the case where the test sample is any of milk, dairy products, and foods produced from milk or dairy products, examples of the cells other than microorganisms in the test sample include bovine leukocytes, mammary epitheliocytes, and so forth. Meanwhile, in the case where the test sample is any of biological samples such as blood samples, urine samples, spinal fluid samples, synovial fluid samples, and pleural effusion samples, examples of the cells include erythrocytes, leukocytes (such as granulocytes, neutrophils, basophils, monocytes, and lymphocytes), thrombocytes, and so forth.

The enzyme is not particularly limited as long as it can degrade the foreign substances and does not damage live cells of microorganism to be detected, and examples thereof include, for example, lipid-degrading enzymes, protein-degrading enzymes and saccharide-degrading enzymes. Of those, one enzyme or two or more enzymes may be used, but it is preferable to use both the lipid-degrading enzyme and protein-degrading enzyme, or all of the lipid-degrading enzyme, protein-degrading enzyme and saccharide-degrading enzyme.

Examples of the lipid-degrading enzymes include lipase, phosphatase, and so forth, examples of the protein-degrading enzymes include serine protease, cysteine protease, proteinase K, pronase, and so forth, and examples of the saccharide-degrading enzyme include amylase, cellulase, and so forth.

The "microorganism" is an object to be detected by the method of the present invention, and is not particularly limited so long as it can be detected by nucleic acid amplification methods, and the agent capable of covalently binding to a DNA or RNA by irradiation with light having a wavelength of 350 nm to 700 nm act on live cells of the microorganism in a manner different from that for dead cells and injured cells of the microorganism. Preferred examples include bacteria, fungi, yeasts, viruses, and so forth. The bacteria include both gram-positive bacteria and gram-negative bacteria. Examples of the gram-positive bacteria include *Staphylococcus* bacteria such as *Staphylococcus epidermidis*, *Streptococcus* bacteria such as *Streptococcus pneumoniae*, *Listeria* bacteria such as *Listeria monocytogenes*, *Bacillus* bacteria such as *Bacillus cereus* and *Bacillus anthracis*, *Mycobacterium* bacteria such as *Mycobacterium tuberculosis*, *Mycobacterium bovis* and *Mycobacterium avium*, *Clostridium* bacteria such as *Clostridium botulinum* and *Clostridium perfringens* and so forth. Examples of the gram-negative bacteria include enterobacteria of which typical examples are *Escherichia* bacteria such as *Escherichia coli*, *Enterobacter* bacteria such as *Enterobacter sakazakii*, *Citrobacter* bacteria such as *Citrobacter koseri*, and *Klebsiella* bacteria such as *Klebsiella oxytoca*, and, *Salmonella* bacteria, *Vibrio* bacteria, *Pseudomonas* bacteria, *Legionella* bacteria, and so forth. Examples of virus include viruses having an envelope such as influenza virus, and viruses not having envelope but having only a nucleocapsid, such as noroviruses, rotaviruses and adenoviruses.

As for viruses, there is known a method for measuring activation and inactivation of virus in water, in which a photoreactive nucleic acid cross-linker (EMA) is allowed to act on a test sample, and then only activated viruses are measured by RT-PCR (Development of ethidium monoazide (EMA)-RT-PCR for selective detection of enteric viruses, 15th International Symposium on Health-Related Water Microbiology, (May 31-Jun. 5, 2009, Ursulines Conference Centre, Naxos, Greece)). That is, it is suggested that EMA does not penetrate activated viruses, but penetrates only inactivated viruses having severely physically injured nucleocapsids, and therefore, activated viruses (live) and inactivated viruses (dead) can be distinguished with EMA. Therefore, it is thought that the present invention can be applied not only to bacteria, filamentous fungi and yeast, but also to viruses.

In the present invention, the "live cell" refers to a cell in a state that the cell can proliferate, and exhibits metabolic activities of the microorganism (viable-and-culturable state), when it is cultured under generally preferred culture conditions, and is a cell substantially free from injury of cell wall. As the metabolic activities mentioned above, ATP activity, esterase activity etc. can be exemplified. In the present invention, viral particles are also called "cells" for convenience. As for viruses, "live cell" refers to a virus in a state that it can infect a mammalian cell and proliferate.

The "dead cell" is a cell in a state that it cannot proliferate, and does not exhibit metabolic activities (dead state), even if it is cultured under an optimum culture condition. Moreover, it is in a state that although structure of cell wall is maintained, the cell wall itself is highly injured, and a nuclear stain agent exhibiting weak permeability such as propidium iodide can penetrate or permeate the cell wall. As for viruses, "dead cell" refers to a virus in a state that it cannot infect a mammalian cell.

The "injured cell" (injured cell or viable-but-non culturable cell) is a cell in a state that even when it is cultured under a generally preferred culture condition, it hardly proliferates because it is injured due to artificial stress or environmental stress, and it shows metabolic activities at a lower level compared with a live cell, but a significant level compared with a dead cell. As for viruses, "injured cell" refers to a virus in a state that even if it infects a mammalian cell, it cannot proliferate in the cell.

In this specification, unless specially mentioned, the "live cell", "dead cell", and "injured cell" mean a live cell, dead cell, and injured cell of a microorganism, respectively.

Detection of bacteria exhibiting the state of injured cells due to mild heat treatment or administration of antibiotics is attracting attention, in particular, in the field of food sanitation inspection and clinical test, and the present invention provides a method for detecting a microorganism, which enables not only detection of live cells, but also distinction of live cells from dead cells or injured cells.

The unit of cell number is usually cell number (cells)/ml for all of live cells, injured cells and dead cells. In this specification, the cell number is represented by a logarithm, and "a $\log_{10}$ cells/ml" means $10^a$ cells/ml.

The number of live cells can be approximated with a number of formed colonies (cfu/ml (colony forming units/ml)) obtainable by culturing the cells under an optimum condition on a suitable plate medium. A standard sample of injured cells of microorganism can be prepared by, for example, subjecting a live cell suspension to a heat treatment, for example, a heat treatment in boiling water. The number of injured cells in such a sample can be approximated with cfu/ml in the live cell suspension before the heat treatment. Although time of the heat treatment in boiling water for preparing injured cells varies depending on type of microorganism, injured cells of the bacteria described in the examples, for example, can be prepared by a heat treatment of about 50 seconds. Further, a standard sample of injured cells of microorganism can also be prepared by a treatment with an antibiotic. In such a case, the cell number of the injured cells can be approximated based on the number of formed colonies (cfu/ml) observed when the cells are cultured under an optimum condition on a suitable plate medium, that is, a live cell suspension is treated with an antibiotic, then the antibiotic is removed, transmittance of visible light (wavelength: 600 nm) through the suspension, i.e., turbidity of the suspension, is measured, and the measured turbidity can be compared with that of a live cell suspension of a known live cell density to calculate the number of injured cells treated with the antibiotic.

As for viruses, unit of cell number is represented by plaque-forming unit (pfu or PFU).

The method of the present invention is for detection of live cells of microorganism, and cells of the microorganism distinguished from live cells may be injured cells or dead cells.

In the present invention, the "detection of live cells" includes both determination of presence or absence of live cells in a test sample and determination of amount of live cells in a test sample. The amount of live cells is not limited to an absolute amount, and may be a relative amount with respect to that in a control sample. Moreover, "to detect live cells by distinguishing the live cells from dead cells or injured cells" means to more selectively detect live cells compared with dead cells or injured cells. In addition, the "distinction of live cells from dead cells or injured cells" includes distinction of live cells from both dead cells and injured cells.

Hereafter, the method of the present invention will be explained for each step. As described above, the method of the present invention may comprise the step of treating the test sample with an enzyme having an activity of decomposing cells other than those of microorganism, colloidal particles of proteins, lipids, or saccharides existing in the test sample, before the steps described below.

(1) Step a)

An agent capable of covalently binding to a DNA or RNA by irradiation with light having a wavelength of 350 nm to 700 nm is added to the test sample. That is, microorganisms in the test sample are treated with the agent.

As described later, the agent intercalates into a double-stranded DNA or RNA and covalently binds to the DNA or RNA by irradiation with light to cross-link the molecules. Further, it is estimated that the agent covalently binds to a single-stranded DNA or RNA by irradiation with light to inhibit reactions of PCR. The agent may henceforth also be simply referred to as "cross-linker".

The cross-linker preferably has different actions on live cells of microorganism compared with injured or dead cells of microorganism and somatic cells such as bovine leukocytes, leukocytes, or thrombocytes. More specifically, the cross-linker is preferably one which can more easily pass through cell walls of injured or dead cells of microorganism and cell membranes of somatic cells such as bovine leukocytes, leukocytes, or thrombocytes compared with cell walls of live cells of microorganism.

Examples of the cross-linker include ethidium monoazide, ethidium diazide, psoralen, 4,5',8-trimethylpsoralen, 8-methoxypsoralen, propidium monoazide, and so forth. One kind of those cross-linkers may be used alone, or two or more kinds thereof may be used in combination.

The conditions of the treatment with the cross-linker may be appropriately set. For example, conditions for easily distinguishing live cells of microorganism from dead or injured cells of microorganism can be determined by: adding various concentrations of a cross-linker to suspensions of live cells of microorganism to be detected and dead or injured cells of microorganism; allowing the suspensions to stand for various periods of time; separating the cells by centrifugation; and analyzing the cells by the nucleic acid amplification method. Moreover, conditions for easily distinguishing live cells of microorganism from various cells can be determined by: adding various concentrations of a cross-linker to suspensions of live cells of microorganism to be detected and somatic cells such as bovine leukocytes or thrombocytes; allowing the suspensions to stand for various periods of time; separating the cells and the various cells by centrifugation; and analyzing the cells by the nucleic acid amplification method. Specifically: conditions of a treatment with ethidium monoazide at a final concentration of 1 to 100 µg/ml for 5 minutes to 48 hours at 4 to 10° C.; conditions of a treatment with ethidium diazide at a final concentration of 1 to 100 µg/ml for 5 minutes to 48 hours at 4 to 10° C.; conditions of a treatment with propidium monoazide at a final concentration of 1 to 100 µg/ml for 5 minutes to 48 hours at 4 to 10° C.; conditions of a treatment with psoralen at a final concentration of $1\times10^{-5}$ to 10 µg/ml for 5 minutes to 48 hours at 25 to 37° C.; conditions of a treatment with 4,5',8-trimethylpsoralen at a final concentration of $1\times10^{-5}$ to 10 µg/ml for 5 minutes to 48 hours at 25 to 37° C.; and conditions of a treatment with 8-methoxypsoralen at a final concentration of $1\times10^{-5}$ to 10 µg/ml for 5 minutes to 48 hours at 25 to 37° C. are exemplified.

(2) Step b)

Next, each test sample containing the cross-linker is irradiated with light having a wavelength of 350 nm to 700 nm.

The cross-linker can easily pass through cell walls of dead cells and injured cells compared with cell walls of live cells of microorganism. Therefore, it is presumed that the cross-linker does not substantially pass through cell walls of live cells of microorganism but passes through cell walls of injured or dead cells of microorganism, or dead somatic cells, provided that the treatment is performed within the above-mentioned periods of time. It is presumed that, as a result, the cross-linker moves into dead somatic cells, dead and injured cells of microorganism, and subsequently form hydrogen bonds with chromosomal DNA or RNA, and then the cross-linker irradiated with light having a wavelength of 350 nm to 700 nm cross-links DNA molecules or covalently binds with RNA and, as a result, causes a deformation in the chromosomal DNA or modification of RNA with the cross-linker, eventually resulting in disruption (fragmentation/cleavage) of the chromosomal DNA, or RNA not serving as a template of a nucleic acid amplification reaction.

The light having a wavelength of 350 nm to 700 nm may include at least light having a wavelength of 350 nm to 700 nm, and the light may be single-wavelength light or multi-wavelength light. In addition, all light components may be in the range of 350 nm to 700 nm, or the light may include short-wavelength light having a wavelength shorter than 350 nm and/or long-wavelength light having a wavelength longer than 700 nm. The peak in an intensity distribution is preferably in the range of 350 nm to 700 nm. Preferably, the light does not include a component with a short wavelength to such a degree that chromosomal DNA of a microorganism is cleaved only by light irradiation.

When chromosomal DNA of injured or dead cells is more preferentially disrupted than that of live cells of microorganism, a target region of the chromosomal DNA of the live cells is amplified by the nucleic acid amplification method, while a target region of the injured or dead cells is disrupted (cleaved), resulting in inhibiting the nucleic acid amplification reactions. As a result, the live cells of microorganism can be detected more selectively than the injured or dead cells.

Further, when RNA of injured or dead cells is more preferentially modified with the cross-linker than that of live cells of microorganism, a target region of RNA of the live cells is amplified by the nucleic acid amplification method, while a target region of RNA of the injured or dead cells is modified, resulting in inhibiting the nucleic acid amplification reactions. As a result, the live cells of microorganism can be detected more selectively than the injured or dead cells.

In a preferred embodiment of the present invention, the cross-linker is ethidium monoazide, and the method includes the step of irradiating a test sample to which ethidium monoazide is added with light having a wavelength of 350 nm to 700 nm. Ethidium monoazide (EMA) can easily pass through cell walls of injured or dead cells compared with cell walls of live cells of microorganism. Therefore, it is presumed that EMA does not substantially pass through cell walls of live cells of microorganism but passes through cell walls of injured or dead cells of microorganism or cell membranes of dead somatic cells.

Note that, in the case where leukocytes and thrombocytes in blood are live cells, EMA can more easily pass through cell walls of the cells in sterilized water or a hypotonic salt solution.

Concerning DNA, in particular, EMA moves into dead somatic cells and injured and dead cells of microorganism and intercalates randomly into nuclear DNA, and intercalated EMA is converted into nitrene by irradiation with light having a wavelength of 350 nm to 700 nm and binds covalently to nuclear DNA to cross-link DNA molecules. Then, it is presumed that EMA which binds covalently to bases and deoxyriboses in chromosomal DNA at many points causes a large deformation in the chromosomal DNA, resulting in disrupting (fragmentating) the chromosomal DNA.

Further, concerning double-stranded RNA (including partially double-stranded RNA), EMA moves into dead somatic cells and injured and dead cells of microorganism and intercalates randomly into RNA, and then intercalated EMA is converted into nitrene by irradiation with light having a wavelength of 350 nm to 700 nm and binds covalently to the RNA to cross-link RNA molecules. Then, it is presumed that EMA which binds covalently to bases of RNA at many points causes a large deformation in the RNA, resulting in disrupting (fragmentating) the RNA.

Furthermore, concerning single-stranded DNA or RNA, it is presumed that EMA moves into dead somatic cells and injured and dead cells of microorganism, and then converted into nitrene by irradiation with light having a wavelength of 350 nm to 700 nm, which binds covalently to the DNA or RNA.

A cross-linker other than ethidium monoazide may also be used so long as the cross-linker can more easily pass through cell walls of injured or dead cells compared with cell walls of live cells of microorganism and can cross-link DNA or covalently binds to RNA by irradiation with light having a wavelength of 350 nm to 700 nm (long-wavelength ultra-violet light or visible light) to thereby disrupt the chromosomal DNA or modify RNA.

Conditions for the treatment with EMA can be appropriately determined. For example, conditions that enables easy distinction of live cells of microorganism from dead cells and injured cells can be determined by adding EMA at various concentrations to suspensions of live cells and injured cells or dead cells of the microorganism to be detected, leaving them for various periods of time, then irradiating them with visible light, removing the cells by centrifugation or the like as required, and performing analysis by nucleic acid amplification methods. Preferred conditions for the irradiation of light can also be appropriately determined by performing such an experiment as mentioned above using various irradiation times. Specific examples of the conditions for the irradiation of light include irradiation of lights of 100 to 750 W and the aforementioned wavelength for 5 minutes to 2 hours from a distance of 10 to 50 cm from the test sample. The irradiation of light is preferably performed at a low temperature, for example, with ice cooling of the sample.

The addition of the cross-linker in the aforementioned step a) and the light irradiation treatment of the step b) may be repeated for 2 or more cycles. In such a case, the concentration of the cross-linker is preferably made higher in the step a) of the first time compared with that in the step a) of the second time or thereafter, and made lower in the step a) of the second time or thereafter compared with that in the step a) of the first time.

For example, if EMA is allowed to act at a high concentration, for example, 10 µg/ml or higher, although permeability for the cell wall or cell membrane of dead cells becomes higher, the permeability for live cells also becomes high (Microbiology and Immunology, 2007, 51, pp. 763-775; Journal of Clinical Microbiology, 2008, 46, pp. 2305-2313). On the other hand, if EMA is allowed to act at a low concentration, for example, lower than 10 µg/ml, although permeation into live cells can be avoided, permeation rate into dead cells also decreases, and therefore, dead cells may also be detected by nucleic acid amplification reactions. Therefore, it is preferable to use a high concentration of the cross-linker in the step a) of the first time, and make the concentration of the cross-linker low in the step b) of second time and thereafter.

Specifically, the final concentration of the cross-linker in the step a) of the first time is, for example, 10 to 100 µg/ml in the case of ethidium monoazide, 10 to 100 µg/ml in the case of ethidium diazide, 10 to 100 µg/ml in the case of propidium monoazide, $2 \times 10^{-5}$ to 10 µg/ml in the case of psoralen, $2 \times 10^{-5}$ to 10 µg/ml in the case of 4,5',8-trimethylpsoralen, or $2 \times 10^{-5}$ to 10 µg/ml in the case of 8-methoxypsoralen. Further, the final concentration of the cross-linker in the step a) of the second time and thereafter is, for example, 1 to 10 µg/ml in the case of ethidium monoazide, 1 to 10 µg/ml in the case of ethidium diazide, 1 to 10 µg/ml in the case of propidium monoazide, $1 \times 10^{-5}$ to 9 µg/ml in the case of psoralen, $1 \times 10^{-5}$ to 9 µg/ml in the case of 4,5',8-trimethylpsoralen, or $1 \times 10^{-5}$ to 9 µg/ml in the case of 8-methoxypsoralen.

Further, the treatment time of the step a) of the first time is preferably made shorter than that of the step a) of the second time and thereafter. Specifically, the treatment time of the step a) of the first time is, for example, 5 minutes to 1 hour in the case of ethidium monoazide, 5 minutes to 1 hour in the case of ethidium diazide, 5 minutes to 1 hour in the case of propidium monoazide, 5 minutes to 1 hour in the case of psoralen, 5 minutes to 1 hour in the case of 4,5',8-trimethylpsoralen, or 5 minutes to 1 hour in the case of 8-methoxypsoralen. The treatment time of the step a) of the second time and thereafter is, for example, 6 minutes to 48 hours in the case of ethidium monoazide, 6 minutes to 48 hours in the case of ethidium diazide, 6 minutes to 48 hours in the case of propidium monoazide, 6 minutes to 48 hours in the case of psoralen, 6 minutes to 48 hours in the case of 4,5',8-trimethylpsoralen, or 6 minutes to 48 hours in the case of 8-methoxypsoralen.

Between the step b) of a previous cycle and the step a) of a following cycle, the step of removing the unreacted cross-linker may be added. Moreover, between the step b) and the step c) described below, the step of removing the cross-linker may be added. The cross-linker that does not react in the step a) is usually substantially inactivated in the step b). Therefore, as a method for removing the cross-linker, a method of centrifuging the test sample to separate precipitates containing microorganism and a supernatant containing the cross-linker, and removing the supernatant is mentioned. In this case, after the cross-linker is removed, the step of washing the microorganism with a washing agent may optionally be added.

(3) Step c)

Then, a target region of the DNA or RNA of the microorganism contained in the test sample after the light irradiation treatment is amplified by a nucleic acid amplification method in the presence of an agent for suppressing an action of a nucleic acid amplification inhibitory substance, without extracting nucleic acids from the cells.

Specifically, the agent for suppressing an action of a nucleic acid amplification inhibitory substance is added to a nucleic acid amplification reaction solution containing the test sample, and the nucleic acid amplification reaction is performed.

Furthermore, in addition to the agent for suppressing an action of a nucleic acid amplification inhibitory substance, a surfactant, a magnesium salt, or an organic acid salt or a phosphoric acid salt may be added to the amplification reaction solution. These substances may be used independently or as a combination of any two or more kinds of these. It is particularly preferable to add all of these substances. The order of the addition of the agent for suppressing an action of a nucleic acid amplification inhibitory substance, the surfactant, the magnesium salt, and the organic acid salt or the phosphoric acid salt is not limited, and they may be simultaneously added.

The nucleic acid amplification inhibitory substance is a substance which inhibits a nucleic acid amplification reaction or a nucleic acid extension reaction, and examples include positively charged inhibitory substances adsorbing to template of nucleic acid (DNA or RNA), negatively charged inhibitory substances adsorbing to nucleic acid biosynthesis enzymes (DNA polymerase etc.), and so forth. Examples of the positively charged inhibitory substances include calcium ion, polyamines, heme, and so forth. Examples of the negatively charged inhibitory substances include phenol, phenol type compounds, heparin, gram-negative bacterium cell wall having outer membranes, and so forth. It is said that such substances that inhibit a nucleic acid amplification reaction are abundantly contained in foodstuffs or clinical test samples.

Examples of the agent for suppressing an action of a nucleic acid amplification inhibitory substance mentioned above include one or more kinds selected from albumin, dextran, T4 gene 32 protein, acetamide, betaine, dimethyl sulfoxide, formamide, glycerol, polyethylene glycol, soybean trypsin inhibitor, α2-macroglobulin, tetramethylammonium chloride, lysozyme, phosphorylase, and lactate dehydrogenase. Examples of the polyethylene glycol include polyethylene glycol 400 and polyethylene glycol 4000. Examples of the betaine include trimethylglycine, derivatives thereof, and so forth. Examples of the phosphorylase and lactate dehydrogenase include rabbit muscular glycogen phosphorylase and lactate dehydrogenase. As the glycogen phosphorylase, glycogen phosphorylase b is preferred.

It is particularly preferable to use albumin, dextran, T4 gene 32 protein, or lysozyme.

As an attempt to reduce the inhibitory action of the nucleic acid amplification inhibitory substance contained in a test sample for which blood, feces, and meat are supposed, reduction of the inhibitory action by adding such substances as described above to a PCR reaction mixture is evaluated (Abu Al-Soud, W. et al, Journal of Clinical Microbiology, 38:4463-4470, 2000).

There is suggested a possibility that albumin of which representative example is BSA (bovine serum albumin) may reduce inhibition of nucleic acid amplification by binding to a nucleic acid amplification inhibitory substance such as heme (Abu Al-Soud et al., as mentioned above). Moreover, there are considered two ways of possibility, that is, the T4 gene 32 protein is a single-stranded DNA binding protein, and it binds to a single-stranded DNA serving as a template in a nucleic acid amplification process in advance so that degradation of the template by a nuclease is avoided, and the nucleic acid amplification reaction is not inhibited, but promoted, or it binds to a nucleic acid amplification inhibitory substance like BSA so that the nucleic acid amplification reaction is not inhibited, but promoted (Abu Al-Soud et al., as mentioned above). Furthermore, there is further suggested a possibility that BSA, the T4 gene 32 protein, and a proteinase inhibitor bind to a proteinase to reduce the proteolysis activity to bring out the actions of nucleic acid biosynthesis enzymes to the maximum extent. In fact, proteinases may remain in cow's milk or blood, and an example is also reported that, in such a case, decomposition of nucleic acid biosynthesis enzymes was avoided by adding BSA or a proteinase inhibitor (e.g., soybean trypsin inhibitor and α2-macroglobulin), and the nucleic acid amplification reaction favorably advanced (Abu Al-Soud et al., as mentioned above). Further, dextran is generally a polysaccharide that is synthesized by lactic acid bacteria using glucose as a raw material, and it is also reported that a complex of a similar polysaccharide and peptide called mucin adheres to the intestinal mucosa (Ruas-Madiedo, P., Applied and Environmental Microbiology, 74:1936-1940, 2008). Therefore, it is possibly estimated that dextran adsorbs to negatively charged inhibitory substances (adsorbs to nucleic acid biosynthesis enzymes), or positively charged inhibitory substances (adsorbs to nucleic acids) in advance, and then binds to these inhibitory substances.

Moreover, it is estimated that lysozyme adsorbs to nucleic acid amplification inhibitory substances considered to be abundantly contained in cow's milk (Abu Al-Soud et al., as mentioned above).

From the above, it can be said that such substances as mentioned above represented by albumin, T4 gene 32 protein, dextran, and lysozyme are agents for suppressing an action of a nucleic acid amplification inhibitory substance.

Examples of albumin include bovine serum albumin, ovalbumin, lactalbumin, human serum albumin, and so forth. Among these, bovine serum albumin is preferred. Albumin may be a purified product, and unless the effect of the present invention is degraded, it may contain other components such as globulin. Further, albumin may also be a fractionation product.

Concentration of albumin in the test sample (nucleic acid amplification reaction solution) is, for example, usually 0.0001 to 1 mass %, preferably 0.01 to 1 mass %, more preferably 0.2 to 0.6 mass %.

Examples of dextran include dextran 40, dextran 500, and so forth. Among these, dextran 40 is preferred. Concentration of the dextran in the test sample (nucleic acid amplification reaction solution) is, for example, usually 1 to 8%, preferably 1 to 6%, more preferably 1 to 4%.

Concentration of the T4 gene 32 protein (e.g., produced by Roche A. G., also called gp32) in the test sample (nucleic acid amplification reaction solution) is usually 0.01 to 1%, preferably 0.01 to 0.1%, more preferably 0.01 to 0.02%.

Examples of lysozyme include lysozyme derived from egg white. Concentration of lysozyme in the test sample (nucleic acid amplification reaction solution) is, for example, usually 1 to 20 µg/ml, preferably 6 to 15 µg/ml, more preferably 9 to 13 µg/ml.

Examples of the surfactant include nonionic surfactants such as those of Triton (registered trademark of Union Carbide), Nonidet (Shell), Tween (registered trademark of ICI) and Brij (registered trademark of ICI) series, anionic surfactants such as SDS (sodium dodecylsulfate), and cationic surfactants such as stearyldimethylbenzylammonium chloride. Examples of the Triton series surfactant include Triton X-100 etc., examples of the Nonidet series surfactant include Nonidet P-40 etc., examples of the Tween series surfactant include Tween 20, Tween 40, Tween 60, Tween 80 etc., and examples of the Brij series surfactant include Brij 56 etc.

Type and concentration of the surfactant in the nucleic acid amplification reaction solution are not particularly limited, so long as the penetration of the PCR reagents into cells of the microorganism is promoted, and the nucleic acid amplification reaction is not substantially inhibited. Specifically, concentration of SDS is, for example, usually 0.0005 to 0.01%, preferably 0.001 to 0.01%, more preferably 0.001 to 0.005%, still more preferably 0.001 to 0.002%. As for the other surfactants, for example, in the case of Nonidet P-40, the concentration is usually 0.001 to 1.5%, preferably 0.002 to 1.2%, more preferably 0.9 to 1.1%. In the case of Tween 20, the concentration is usually 0.001 to 1.5%, preferably 0.002 to 1.2%, more preferably 0.9 to 1.1%. In the case of Brij56, the concentration is usually 0.1 to 1.5%, preferably 0.4 to 1.2%, more preferably 0.7 to 1.1%.

When a surfactant is contained in an enzyme solution used for the nucleic acid amplification reaction, the surfactant may consist of only the surfactant derived from the enzyme solution, or a surfactant of the same type or different type may be further added.

Examples of the magnesium salt include magnesium chloride, magnesium sulfate, magnesium carbonate, and so forth. Concentration of the magnesium salt in the test sample (nucleic acid amplification reaction solution) is, for example, usually 1 to 10 mM, preferably 2 to 6 mM, more preferably 2 to 5 mM.

Examples of the organic acid salt include salts of citric acid, tartaric acid, propionic acid, butyric acid, and so forth. Examples of type of the salt include sodium salt, potassium salt, and so forth. Further, examples of the phosphoric acid salt include salts of pyrophosphoric acid and so forth. These may be used independently or as a mixture of two or three or more kinds of them. Concentration of the organic acid salt or the phosphoric acid salt in the test sample (nucleic acid amplification reaction solution) is, for example, usually 0.1 to 20 mM, preferably 1 to 10 mM, more preferably 1 to 5 mM, in terms of the total amount.

In the present invention, extraction of nucleic acids from the cells is not performed, which is performed before the nucleic acid amplification reaction in conventional methods. The extraction of nucleic acids from cells means, for example, collection or purification of nucleic acids from cells disrupted or lysed by an enzymatic or physical means. In the present invention, such a treatment for extracting nucleic acids from cells, for example, a treatment of collecting or purifying nucleic acids by disrupting or lysing the cells by an enzymatic or physical means, is not performed.

A target region of the DNA or RNA which has existed in the cells is amplified by a nucleic acid amplification method in the presence of the agent for suppressing an action of a nucleic acid amplification inhibitory substance, and other components, if needed. As the template for the nucleic acid amplification, a microbial cell suspension or a microbial cell suspension treated with a protein-degrading enzyme, a lipid-degrading enzyme, a saccharide-degrading enzyme etc. is used, and extraction of nucleic acids for preparing the template is not performed. The nucleic acid amplification method preferably comprises the step of thermal denaturation of nucleic acids at a high temperature, for example, 90 to 95° C., preferably 93 to 95° C., more preferably 94 to 95° C.

The amplification of the target region is preferably performed in microbial cells. In the present invention, the amplification is highly possibly attained in microbial cells as shown in the examples. That is, it is presumed that the morphology of the cells is maintained by the high temperature treatment in the nucleic acid amplification reaction, and, in a preferred embodiment, actions the of aforementioned components, so that the chromosomal DNA is retained in the cells, but pinholes or voids are formed in the cell membranes or cell walls of the microorganism, thus primers, enzymes required for the nucleic acid amplification etc. flow into the cells, the amplification reaction occurs in the cells, and then a part of the amplified product remains in the cells or flow out of the cells depending on the gene length of the amplified product. However, a possibility that an extremely small part of the chromosomal DNA or RNA flows out of the cells through the pinholes or voids of the cell membranes or cell walls cannot be denied, either.

In any case, inflow of components required for the nucleic acid amplification such as primers into the cells without substantial disruption or lysis of the cells, retention in the cells or outflow from the cells of a part of the amplified product, and outflow of the chromosomal DNA or RNA from the cells are not included in the "extraction of nucleic acids". Moreover, although existence of a mechanism other than that described above cannot be negated, even in such a case, the method complies with the definition that "extraction of nucleic acids is not performed", so long as a treatment of collecting or purifying nucleic acids by disrupting or lysing the cells by, for example, an enzymatic or physical means, is not performed.

In addition, even when the chromosomal DNA or RNA flown out from the cells serves as a template, and the nucleic acid amplification reaction occurs out of the cells, if the major amplified product is formed in the cells, it can be said that the nucleic acid amplification reaction is "performed in microbial cells". Specifically, for example, if 80% or more, preferably 90% or more, more preferably 99% or more, of the amplified product is formed in the microbial cells, it can be estimated that the nucleic acid amplification reaction is performed in the microbial cells.

Examples of the nucleic acid amplification method include PCR method (White, T. J. et al., Trends Genet., 5, 185 (1989)), LAMP method (Loop-Mediated Isothermal Amplification: Principal and application of novel gene amplification method (LAMP method), Tsugunori Notomi, Toru Nagatani, BIO INDUSTRY, Vol. 18, No. 2, 15-23, 2001), SDA method (Strand Displacement Amplification: Edward L. Chan, et al., Arch. Pathol. Lab. Med., 124:1649-1652, 2000), LCR method (Ligase Chain Reaction: Barany, F., Proc. Natl. Acad. Sci. USA, Vol. 88, p. 189-193, 1991), TMA method (Transcription-Mediated-Amplification: Sarrazin C. et al., J. Clin. Microbiol., vol. 39: pp. 2850-2855 (2001)), TRC method (Transcription-Reverse Transcription-Concerted method: Nakaguchi Y. et al., J. Clin. Microbiol., vol. 42: pp. 4248-4292 (2004)), HC method (Hybrid Capture: Nazarenko I., Kobayashi L. et al., J. Virol. Methods, vol. 154: pp. 76-81, 2008), microarray method (Richard P. Spence, et al., J. Clin. Microbiol., Vol. 46, No. 5, pp. 1620-1627, 2008), and so forth. In the present invention, although the PCR method is particularly preferably used, the nucleic acid amplification method is not limited thereto.

In the present invention, the "target region" is not particularly limited so long as a region of a chromosomal DNA or RNA that can be amplified by PCR using primers used for the present invention and enables detection of a microorganism to be detected is selected, and it can be suitably selected depending on the purpose. For example, when cells of a type different from that of the microorganism to be detected are contained in the test sample, the target region preferably contains a sequence specific to the microorganism to be detected. Further, depending on the purpose, the target region may be one containing a sequence common to several kinds of microorganisms. Furthermore, the target region may consist of a single region or two or more regions. If a primer set suitable for a target region specific to the microorganism to be detected and a primer set suitable for chromosomal DNAs of wide varieties of microorganisms are used, live cell amount of the microorganism as the object of the detection and live cell amount of the wide varieties of microorganisms can be simultaneously measured. Length of the target region is, for example, usually 50 to 5000 nucleotides.

The primers to be used in amplification of a nucleic acid may be selected based on principles of various nucleic acid amplification methods and are not particularly limited as long as the primers can specifically amplify the above-mentioned target region.

Preferred examples of the target region include various specific genes such as a 5S rRNA gene, 16S rRNA gene, 23S rRNA gene, tRNA gene, and pathogen gene. Any one of these genes or a part of any one of these genes may be targeted, or a region extending over two or more genes may be targeted. For example, as for coliform bacteria and bacteria of the family Enterobacteriaceae, a part of the 16S rRNA gene can be amplified by using the primer set shown in SEQ ID NOS: 1 and 2. Further, a region extending over a part of the 16S rRNA gene, a tRNA gene, and a part of the 23S rRNA gene can be amplified by using the primer set shown in SEQ ID NOS: 3 and 4.

In the case where the microorganism of the detection target is a pathogenic bacterium, the target region may be a pathogenic gene. Examples of the pathogenic gene include: listeriolysin O (hlyA) gene of a *Listeria* bacterium; enterotoxin gene and invasion (invA) gene of a *Salmonella* bacterium; verotoxin genes of pathogenic *Escherichia coli* 0-157, 0-26, 0-111 etc.; outer-membrane-protein A (ompA) gene (*Enterobacter sakazakii*) and macromolecular synthesis (MMS) operon (*Enterobacter sakazakii*) of an *Enterobacter* bacterium; macrophage-invasion protein (mip) gene of a *Legionella* bacterium; heat-resistant hemolysin gene and heat-resistant hemolysin-like toxin gene of *Vibrio parahaemolyticus*; ipa gene (invasion plasmid antigen gene) and invE gene (invasion gene) of *Shigella dysenteriae* and enteroinvasive *Escherichia coli*; enterotoxin gene of *Staphylococcus aureus*; cereulide gene and enterotoxin gene of *Bacillus cereus*; various toxin genes of *Clostridium botulinum*, and so forth. Further, examples of primers for a pathogenic gene include, for example, a set of primers shown in SEQ ID NOS: 5 and 6 for hlyA gene of *Listeria* bacterium; a set of primers shown in SEQ ID NOS: 7 and 8 for ompA gene of *Enterobacter sakazakii*; and a set of primers shown in SEQ ID NOS: 9 and 10 for MMS operon of *Enterobacter sakazakii*.

Furthermore, in the case of the influenza virus having an envelope, examples of the target region include the hemagglutinin (H protein) gene and the neuraminidase (N protein) gene, RNA polymerase gene of the Calicivirus family viruses of which representative examples include noroviruses, genetic regions coding for various capsid proteins, and so forth. As food poisoning viruses, besides noroviruses, there are also rotaviruses and adenoviruses, and as the objective gene, RNA polymerase genes and genetic regions coding for various capsid proteins thereof may be used as the target region as in the case of noroviruses.

If primers suitable for two or more kinds of microorganisms are used, live cells of two or more kinds of the microorganisms in a test sample can be detected. Moreover, if a primer(s) specific to a particular bacterium are used, live cells of the particular bacterium in a test sample can be detected.

Conditions of nucleic acid amplification reactions are not particularly limited as long as a nucleic acid can be specifically amplified based on principles of various nucleic acid amplification methods (such as PCR, LAMP, SDA, LCR, TMA, TRC, HC, microarray method, etc.), and the conditions may be appropriately set.

(4) Step d)

Subsequently, amplified products obtained by the nucleic acid amplification method are analyzed. The analysis of the amplified products is performed following the step c), or performed simultaneously with the step c), depending on the nucleic acid amplification method adopted in the step c). For example, in the case of using real-time PCR, the step d) may be performed simultaneously with the step c).

The analysis method is not particularly limited as long as the method can detect or quantify the nucleic acid amplified products, and examples thereof include electrophoresis. Note that, in the case of using PCR method for the nucleic acid amplification method, a real-time PCR method (Nogva et al., Appl. Environ. Microbiol., vol. 66, 2000, pp. 4266-4271; Nogva et al., Appl. Environ. Microbiol., vol. 66, 2000, pp. 4029-4036) can be used.

The electrophoresis enables evaluation of the amounts and sizes of the nucleic acid amplified products. In addition, real-time PCR enables rapid quantification of PCR amplified products.

In the case where the real-time PCR is employed, changes in fluorescent intensities are generally noise levels and about zero if the number of amplification cycles is in the range of 1 to 10. Therefore, the intensities are regarded as sample blanks containing no amplified products. The standard deviation (SD) of the changes is calculated, and a value obtained by multiplying the SD value by 10 is defined as a threshold value. The number of PCR cycles in which a value larger than the threshold value is achieved for the first time referred to as "cycle threshold value (Ct value)". Therefore, the larger the initial amount of a DNA template in a PCR reaction solution, the smaller the Ct value, while the smaller the amount of the template DNA, the larger the Ct value. Even if the amounts of the template DNA are the same, the higher the proportion of the template where a target region of PCR has been cleaved, the larger the Ct value in PCR reactions for the region.

Further, presence or absence of the amplified product can also be determined by analyzing the melting temperature (TM) pattern of the amplified product.

All the aforementioned methods can also be used for optimization of various conditions for the method of the present invention.

When live cells of microorganism are detected by the method of the present invention, precisions of the determination of the presence or absence of live cells of microorganism and quantification of the same in the analysis of the PCR amplified product can be increased by using a standard curve representing relationship between the amount of microorganism and the amplified product, which is prepared by using standard samples of the microorganism in which the microorganism is identified. Although a preliminarily prepared standard curve may be used, it is preferable to use a standard curve prepared by performing the steps of the method of the present invention for standard samples at the same time with a test sample. Moreover, if relationship between amount of microorganism and amount of DNA or RNA is determined beforehand, DNA or RNA isolated from the microorganism can also be used as a standard sample.

<2> Kit of the Present Invention

The kit of the present invention is a kit for detecting live cells of a microorganism in a test sample by a nucleic acid amplification method by distinguishing the live cells from a dead cells or injured cells and comprises an agent capable of covalently binding to a DNA or RNA by irradiation with light having a wavelength of 350 nm to 700 nm, an agent for suppressing an action of a nucleic acid amplification inhibitory substance, and a primer(s) for amplifying a target region of DNA or RNA of a microorganism to be detected by the nucleic acid amplification method. The kit of the present invention can be used for implementing the method of the present invention.

In addition, the kit of the present invention may further comprise any one or more kinds selected from a surfactant, a magnesium salt and an organic acid salt or a phosphoric acid salt.

Moreover, the kit of the present invention may further comprise an enzyme having an activity of decomposing cells other than that of microorganism, a colloidal particle of a protein, a lipid, or a saccharide existing in the test sample.

The enzyme, the agent capable of covalently binding to a DNA or RNA, and the agent for suppressing an action of a nucleic acid amplification inhibitory substance, as well as the surfactant, the magnesium salt and the organic acid salt or phosphoric acid salt, as required, may be in the form of a single composition containing all of these components, or two or more solutions or compositions containing the components in arbitrary combinations.

The nucleic acid amplification reaction is preferably PCR, LAMP, SDA, LCR, TMA, TRC, HC or microarray method. The cross-linker and the medium in the kit are the same as those described for the method of the present invention.

In a preferred embodiment of the kit of the present invention, the agent capable of covalently binding to a DNA or RNA is preferably selected from ethidium monoazide, ethidium diazide, propidium monoazide, psoralen, 4,5',8-trimethylpsoralen, and 8-methoxypsoralen. Ethidium monoazide is particularly preferably used.

Furthermore, examples of the agent for suppressing an action of a nucleic acid amplification inhibitory substance include one or more kinds selected from albumin, dextran, T4 gene 32 protein, acetamide, betaine, dimethyl sulfoxide, formamide, glycerol, polyethylene glycol, soybean trypsin inhibitor, α2-macroglobulin, tetramethylammonium chloride, lysozyme, phosphorylase, and lactate dehydrogenase.

Furthermore, examples of the magnesium salt include magnesium chloride, magnesium sulfate, magnesium carbonate, and so forth.

Furthermore, examples of the organic acid salt include salts of citric acid, tartaric acid, propionic acid, butyric acid, and so forth. Examples of type of the salt include sodium salt, potassium salt, and so forth. Further, examples of the phosphoric acid salt include salts of pyrophosphoric acid and so forth. These may be used independently or as a mixture of two or three or more kinds of them.

Furthermore, the enzyme is not particularly limited as long as it can degrade the foreign substances such as cells other than microorganisms, protein colloidal particles, lipids and saccharides existing in the test sample, and does not damage live cells of microorganism to be detected, and examples thereof include lipid-degrading enzymes, protein-degrading enzymes and saccharide-degrading enzymes. Of those, one enzyme or two or more enzymes may be used, but it is preferable to use both the lipid-degrading enzyme and protein-degrading enzyme, or all of the lipid-degrading enzyme, protein-degrading enzyme and saccharide-degrading enzyme.

Examples of the lipid-degrading enzymes include lipase, phosphatase, and so forth, examples of the protein-degrading enzymes include serine protease, cysteine protease, proteinase K, pronase, and so forth, and examples of the saccharide-degrading enzyme include amylase, cellulase, and so forth.

The kit of the present invention may further comprise a diluting solution, a reaction solution for the reaction of the agent capable of covalently binding to a DNA or RNA, enzymes and reaction solutions for nucleic acid amplification, an instruction describing the method of the present invention, and so forth.

EXAMPLES

Hereinafter, the present invention is described more specifically with reference to the following examples. However, the present invention is not limited to the examples.

Example 1

By using *Enterobacter sakazakii* as a representative bacterium of coliform bacteria, conditions for definite distinction of live cells and dead cells were examined.
1. Test Materials and Culture Method
1-1) Used Strain and Culture Method The *Enterobacter sakazakii* ATCC51329 was cultured at 37° C. for 16 hours by using the Brain Heart Infusion Broth (BHI broth, Eiken Chemical Co., Ltd., Tokyo, Japan). The culture broth in a volume of 5 ml was put into a 15-ml falcon tube (Becton Dickinson Labware, NJ), and subjected to refrigerated centrifugation at 4° C. and 3,000×G for 10 minutes, the supernatant was removed, and then 5 ml of physiological saline was added to the pellet to prepare a stock live cell suspension of *Enterobacter sakazakii* (8.95±0.01 $\log_{10}$ cells/ml, n=2). Further, this live cell suspension was diluted 10 times with physiological saline to prepare a live cell suspension of *Enterobacter sakazakii* (7.95±0.01 $\log_{10}$ cells/ml, n=2).

Further, 1 ml of the aforementioned stock live cell suspension was put into a 1.5-ml volume microtube (Eppendorf, Hamburg, Germany), the tube was immersed into boiling water for 50 seconds and quenched, and it was confirmed that the bacterium thereafter did not form any colony on a standard agar medium (Eiken, Tokyo, Japan) to prepare a stock injured cell suspension of *Enterobacter sakazakii*. The live cell count of *Enterobacter sakazakii* in the live cell suspension was counted on the standard agar medium, and turbidimetry was simultaneously carried out at a wavelength of 600 nm by using a spectrophotometer U-2800A (Hitachi, Japan) to figure out the relationship between the live cell count and the turbidity.

Further, the stock live cell suspension was diluted 10 times with marketed pasteurized cow's milk to prepare a live cell milk suspension of *Enterobacter sakazakii* (7.95±0.01 $\log_{10}$ cells/ml, n=2).

Furthermore, the stock injured cell suspension was diluted 10 times with marketed pasteurized cow's milk to prepare an injured cell milk suspension of *Enterobacter sakazakii* (7.95±0.01 $\log_{10}$ cells/ml, n=2).

1-2) Ethidium Monoazide (EMA) Treatment and Light Irradiation Treatment

Ethidium monoazide (EMA, Sigma, St. Louis, Mo.) was dissolved at 1000 µg/ml using sterilized water, and subjected to filtration sterilization by using 0.20-µm filter (Minisartplus, Sartorius AG, Gottingen, Germany) to prepare a stock solution, which was stored at −20° C. under light shielding.

The EMA solution (1000 µg/ml) in a volume of 10 µl was added to the live cell and injured cell suspensions (1 ml) of *Enterobacter sakazakii*, and the suspensions were left at 4° C. for 10 minutes under light shielding. Then, the suspensions were placed at a distance of 20 cm from a visible light source (100V PRF 500W Flood eye, Iwasaki Electric Co., Ltd., Tokyo, Japan), and irradiated with light for 5 minutes on ice. Each EMA-treated sample was subjected to refrigerated centrifugation at 4° C. and 15,000×G for 10 minutes, the supernatant was removed, then 1 ml of physiological saline was added to the pellet for washing, 10 µl of sterilized water was added to the precipitates (cells) to suspend the cells in the sterilized water, and 5 µl of the suspension was used as a sample for PCR amplification.

The live cell and injured cell milk suspensions (1 ml) of *Enterobacter sakazakii* were subjected to an EMA treatment and light irradiation treatment by the following methods. First, each of the live cell and injured cell milk suspensions (1 ml) of *Enterobacter sakazakii* was subjected to refrigerated centrifugation at 4° C. and 15,000×G for 10 minutes, the supernatant was removed, and then 1 ml of physiological saline was added. A protease (derived from *Bacillus* bacterium, Sigma) in a volume of 3 µl was added to treat the cells with the protease at 37° C. for 1 hour, then the suspension was subjected to refrigerated centrifugation (4° C., 15,000×G, 10 minutes), the supernatant was removed, 1 ml of physiological saline was added, and then 10 µl of the EMA solution (1000 µg/ml) was added under light shielding. The methods used thereafter were the same as those described for the aforementioned "live cell and injured cell suspensions of *Enterobacter sakazakii* (1 ml)".

1-3) PCR Amplification

An agent comprising trisodium citrate dihydrate (TSC, Kanto Kagaku) and magnesium chloride hexahydrate (Nakarai-Tesque) and further containing one or more selected from bovine serum albumin (BSA, Sigma), dextran (low molecule, M.W.: 50,000 to 70,000, Nakarai-Tesque), T4 gene protein 32 (gp32, Nippon Gene), sodium laurylsulfate (SDS, Nakarai-Tesque), Brij56 (Sigma), and egg white lysozyme (Wako Pure Chemical Industries) was added to 5 µl of the sample for PCR amplification. Each agent added to the sample for PCR amplification and having each composition may also be referred to as pretreatment agent. Compositions of the pretreatment agents are shown below.

Composition 1:
2% BSA: 5 µl
50 mM TSC: 1 µl
100 mM $MgCl_2$: 1.5 µl
0.05% SDS: 1 µl Composition 2:
2% BSA: 5 µl
50 mM TSC: 1 µl
100 mM $MgCl_2$: 1.5 µl Composition 3:
20% Dextran: 2.5 µl
50 mM TSC: 1 µl
100 mM $MgCl_2$: 1.5 µl Composition 4:
0.1% gp32: 5 µl
50 mM TSC: 1 µl
100 mM $MgCl_2$: 1.5 µl Composition 5:
2% BSA: 5 µl
50 mM TSC: 1 µl
100 mM $MgCl_2$: 1.5 µl
4% Brij56: 12.6 µl Composition 6:
2% BSA: 5 µl
50 mM TSC: 1 µl
100 mM $MgCl_2$: 1.5 µl
500 µg/ml Egg white lysozyme: 1.0 µl Composition 7:
2% BSA: 5 µl
50 mM TSC: 1 µl
100 mM $MgCl_2$: 1.5 µl
0.05% SDS: 1 µl
4% Brij56: 12.6 µl
500 µg/ml Egg white lysozyme: 1.0 µl Composition 8:
2% BSA: 5 µl
50 mM TSC: 1 µl
100 mM $MgCl_2$: 1.5 µl
4% Brij56: 12.6 µl
500 µg/ml Egg white lysozyme: 1.0 µl Composition 9:
2% BSA: 5 µl Composition 10:
Only the PCR buffer consisting of the component a) to g) mentioned below, not containing the components of the compositions 1 to 9

For the PCR amplification, Primer F: forward primer 16S_10F for 16S rRNA gene detection (5'-AGTTTGATC-CTGGCTC-3', SEQ ID NO: 1), and Primer R: reverse primer 16S_1500R for 16S rRNA gene detection (5'-GGC-TACCTTGTTACGA-3', SEQ ID NO: 2) were used as PCR primers.

Further, in order to maximize variation (primary differential peak) of the fluorescent substance amount depending on the temperature to perform high sensitivity detection in the melt analysis of the amplified products after the real-time PCR, a PCR buffer consisting of the following components a) to g) was prepared, and the PCR amplification was performed by adding this PCR buffer to the mixture of the sample for PCR amplification and the pretreatment agent.

The target of the aforementioned primers was a long DNA (1491 bp) comprising 10 to 1500th nucleotides of 16S rRNA gene.

a) Primer F (10 pmol/μl): 4 μl
b) Primer R (10 pmol/μl): 4 μl
c) Ex-Taq (5 U/μl, Takara-Bio): 0.5 μl (containing 0.5% Tween 20, 0.5% Nonidet P-40, and 50% glycerol)
d) 10×Ex-Taq Buffer (Takara-Bio): 5 μl
e) dNTP mixture (Takara-Bio): 4 μl
f) 10×SYBR Green I (BMA): 8 μl
g) Sterilized water: volume required to obtain the total volume of 55 μl including 5 μl of the sample for PCR amplification and the pretreatment agent Real-time PCR was performed according to the following PCR thermal cycle conditions by using a real-time PCR apparatus (iCycler iQ, Bio-Rad, Hercules, Calif.).
1) 4° C. for 3 minutes (1 cycle)
2) 94° C. for 30 seconds (1 cycle)
3) 94° C. for 20 seconds; 55° C. for 30 seconds; 72° C. for 1 minute and 30 seconds (50 cycles)
4) 95° C. for 3 minutes (1 cycle)

Then, according to the protocol of the melt analysis of the PCR amplified product (temperature was raised at intervals of 0.1° C. from 60° C., each temperature was maintained for 8 seconds, and this procedure was repeated 350 times in total up to the final temperature of 95° C.), the melting temperature of the PCR amplified product was measured.

As a positive control, 8 $\log_{10}$ cells/ml live cell suspension of *Enterobacter sakazakii* was used. Further, as a blank sample, the PCR buffer itself to which nothing was added was used for PCR.

2. Results

The results of the real-time PCR are shown in Table 1.

The symbols a) to f) used in Table 1 indicate the followings. Further, "Lyso" used for the pretreatment agent means egg white lysozyme.

a) Live cell counts and injured cell counts of *Enterobacter sakazakii*: 7.95±0.01 $\log_{10}$ cells/ml (in physiological saline and marketed pasteurized cow's milk)
b) Injured cells were prepared by immersing live cells in boiling water for 50 seconds.
c) No treatment with EMA is meant.
d) EMA treatment (10 μg/ml, 10 minutes, 4° C. under light shielding)+visible light irradiation (5 minutes)
e) Ct value of real-time PCR indicated as mean±SD (n=2)
f) nd means that amplification of the objective gene was not attained by the real-time PCR.

tion of live state and injured state of *Enterobacter sakazakii* in cow's milk were clearly attained, and according to the evaluation based on the Ct value serving as an index of the reaction rate of the real-time PCR, significant differences were not observed among the Ct values of *Enterobacter sakazakii* in physiological saline and cow's milk (live cells, not treated with EMA), or among those of the live cells subjected to the EMA treatments of various conditions. From these results, it was found that it makes no difference if the surfactant SDS is contained or not contained in the pretreatment agent. The same phenomenon as mentioned above was also observed in comparison of the results obtained with the compositions 7 and 8.

As seen from comparison of the results obtained with the compositions 2, 3 and 4, for all the cases where any of albumin, dextran, and the T4 gene protein 32 was contained in the composition, distinction of live state and injured state of *Enterobacter sakazakii* (in physiological saline and cow's milk) was clearly attained, and significant differences were not observed among the Ct values of *Enterobacter sakazakii* in physiological saline and cow's milk (live cells, not treated with EMA), or among those of the live cells subjected to the EMA treatments of various conditions. On the basis of these data, it was found that any of albumin, dextran, and the T4 gene protein 32 may be used.

As seen from comparison of the results obtained with the compositions 2 and 5, distinction of live state and injured state of *Enterobacter sakazakii* was clearly attained with both compositions (in physiological saline and cow's milk), but it was suggested that addition of the nonionic surfactant Brij56 provided a significant decrease of the Ct values of *Enterobacter sakazakii* (live cells, not treated with EMA and treated with EMA), especially that of the cells in cow's milk, and thus sensitivity for detection of live cells was improved. Furthermore, in comparison of the results obtained with the compositions 2 and 6, it was observed that distinction of live state and injured state was clearly attained with both compositions (in physiological saline and cow's milk), but there was a tendency that addition of lysozyme more improved the sensitivity for detection of live cells in cow's milk (not treated with EMA and treated with EMA).

On the basis of comparison of the results obtained with the compositions 5, 6 and 8, it was found that distinction of live state and injured state was clearly attained with all of the

TABLE 1

| Composition | Pretreatment agent | | | | | | | | In physiological saline | | | | In cow's milk | | | |
|---|---|---|---|---|---|---|---|---|---|---|---|---|---|---|---|---|
| | | | | | | | | | Live cell [a] | | Injured cell [a)b)] | | Live cell [a] | | Injured cell [a)b)] | |
| | BSA | Dex | Gp32 | TSC | MgCl$_2$ | SDS | Brij56 | Lyso | 0 [c] | 10 [d] | 0 | 10 | 0 [c] | 10 [d] | 0 | 10 |
| 1 | + | − | − | + | + | + | − | − | 17 ± 0.9 | 21 ± 3.2 | 20 ± 4.2 [e] | nd [f] | 32 ± 0.8 | 35 ± 0.9 | 35 ± 1.1 | nd |
| 2 | + | − | − | + | + | − | − | − | 17 ± 0.6 | 20 ± 1.4 | 20 ± 1.1 | nd | 31 ± 1.4 | 34 ± 1.6 | 35 ± 1.0 | nd |
| 3 | − | + | − | + | + | − | − | − | 17 ± 0.7 | 20 ± 0.8 | 20 ± 1.2 | nd | 32 ± 0.7 | 34 ± 1.4 | 35 ± 1.2 | nd |
| 4 | − | − | + | + | + | − | − | − | 18 ± 0.5 | 20 ± 1.8 | 20 ± 1.8 | nd | 33 ± 0.6 | 35 ± 0.6 | 35 ± 1.8 | nd |
| 5 | + | − | − | + | + | − | + | − | 16 ± 0.8 | 19 ± 0.9 | 19 ± 0.8 | nd | 25 ± 1.2 | 27 ± 0.8 | 27 ± 1.4 | nd |
| 6 | + | − | − | + | + | − | − | + | 17 ± 1.1 | 19 ± 0.7 | 19 ± 0.6 | nd | 28 ± 0.9 | 31 ± 0.8 | 32 ± 0.9 | nd |
| 7 | + | − | − | + | + | + | + | + | 15 ± 0.6 | 18 ± 1.2 | 18 ± 0.8 | nd | 22 ± 0.8 | 24 ± 0.5 | 24 ± 1.5 | nd |
| 8 | + | − | − | + | + | − | + | + | 16 ± 0.4 | 19 ± 1.3 | 19 ± 1.2 | nd | 22 ± 0.8 | 24 ± 0.8 | 24 ± 1.2 | nd |
| 9 | + | − | − | − | − | − | − | − | 18 ± 0.8 | 21 ± 1.1 | 21 ± 1.3 | nd | 34 ± 1.1 | 37 ± 1.4 | 38 ± 1.6 | nd |
| 10 | − | − | − | − | − | − | − | − | 25 ± 0.7 | 28 ± 1.1 | 28 ± 1.8 | nd | nd | nd | nd | nd |

As seen from the results for the compositions 1 and 2 shown in Table 1, in this system where PCR was directly performed in the bacterium, distinction of live state and injured state (distinction of live cells and injured cells) of *Enterobacter sakazakii* in physiological saline, and distinccompositions (in physiological saline and cow's milk), but coexistence of Brij56 and egg white lysozyme clearly improved the sensitivity for detection of live cells (not treated with EMA and treated with EMA) as shown by the results obtained with the composition 8. Egg white lysozyme directly acts on the peptidoglycans of gram-positive bacteria to hydrolyze the polysaccharides (β-1,4-linkages of N-acetylglucosamine and N-acetylmuramic acid), however, in the case of gram-negative bacteria, there is an outer membrane outside the peptidoglycan containing these polysaccharides (on the side where egg white lysozyme functions), and therefore egg white lysozyme cannot act on. Taking this action mechanism into consideration, it can be considered that egg white lysozyme in the composition 8 did not promote lysis (disruption) of the cells of *Enterobacter sakazakii*, which is a gram-negative bacterium, but strongly acted on cell walls of dead cells of gram-positive bacteria existing in cow's milk in advance (≥5 $\log_{10}$ cells/ml) in the presence of Brij56 to physicochemically change the cell wall surface structures of gram-positive bacteria, which are conventionally considered to be PCR inhibitory components, and therefore the cell wall surface structures could no longer function as PCR inhibitory components. In fact, in comparison of the results obtained with the compositions 5, 6 and 8, it can be seen that the sensitivity for detection of live cells in cow's milk was significantly improved with the composition 8, but gram-positive bacteria did not exist as contaminants among the live cells suspended in physiological saline, and any data indicating that the composition 8 especially promotes reactions in PCR have not been obtained for live cells of *Enterobacter sakazakii*, which is a gram-negative bacterium.

From the above, it can be considered that egg white lysozyme did not participate in the lysis of gram-negative bacteria in the presence of Brij56, but physicochemically changed the cell walls of the gram-positive bacteria originally contained in the test sample and considered as PCR contaminants to make them not function as PCR inhibitory components, and therefore it markedly improved the sensitivity for detection of live cells of *Enterobacter sakazakii* as the object, which is a gram-negative bacterium, as a result. This also agrees with the fact that, in comparison of the results obtained with the compositions 2 and 8, any significant difference was not observed in the sensitivity (Ct value) for detecting live cells in physiological saline, but extremely superior sensitivity for detecting live cells in cow's milk (containing many injured cells and dead cells of gram-positive bacteria) was obtained with the composition 8. Moreover, it is considered that egg white lysozyme adsorbs to a nucleic acid amplification inhibitory substance to normally advance the nucleic acid amplification reaction.

On the basis of comparison of the results obtained with the compositions 1, 2 and 9, it is considered that if the function of a nucleic acid amplification reaction inhibitory substance can be suppressed with BSA, distinction of live cells and injured cells is possible, even if a magnesium salt or an organic acid salt is not contained. In addition, with the composition 9, the Ct values for the live cells (not treated with EMA and treated with EMA) and injured cells (not treated with EMA) delayed by about 3, and therefore the compositions 1 and 2 containing the magnesium salt or the organic acid salt are more advantageous in view of the reactivity.

Finally, as seen from comparison of the results obtained with the compositions 2 and 10, although distinction of live state and injured state of *Enterobacter sakazakii* suspended in physiological saline was possible only with the PCR buffer, but the sensitivity (Ct value) for live cells (not treated with EMA and treated with EMA) was extremely significantly unfavorable, in addition, in the case of supposing cow's milk as a usual typical test sample, live cells (not treated with EMA and treated with EMA) and injured cells not treated with EMA cannot be detected only with the PCR buffer, and therefore it is considered that it is preferred that at least an agent that can reduce the influence of a PCR inhibitory substance, of which representative example is albumin, and a magnesium salt and an organic acid salt or a phosphoric acid salt are contained.

Example 2

Distinctions of live cells and injured cells of coliform bacteria and Enterobacteriaceae bacteria were performed.
1. Test Materials and Test Methods
1-1) Used Strains and Culture Method Bacteria of 16 genera of the coliform bacteria and 1 genus of Enterobacteriaceae not belonging to the coliform bacteria, *Klebsiella oxytoca* JCM1665, *Citrobacter koseri* JCM1658, *Enterobacter sakazakii* ATCC51329, *Serratia fonticola* JCM1242, *Budvicia aquilia* JCM3902, *Rahnella aquatilis* NBRC13544, *Hafnia alvei* JCM1666, *Leclercia adecarboxylata* JCM1667, *Yokenella regensburgei* JCM2403, *Pantoea agglomerans* JCM1236, *Buttiauxella agrestis* JCM1090, *Kluyvera ascorbata* JCM2107, *Cedecea davisae* JCM1685, *E. coli* (*Escherichia coli*) DH5α, and *Salmonella enteritidis* IID604 were cultured at 37° C. for 16 hours by using the Brain Heart Infusion Broth (BHI broth, Eiken Chemical Co., Ltd., Tokyo, Japan).

Further, bacteria of 2 species belonging to 2 genera of the coliform bacteria, *Ewingella americana* JCM4911 and *Moellerella wisconsensis* JCM5894 were cultured at 30° C. for 16 hours by using the BHI broth.

Each culture broth in a volume of 5 ml after the culture was collected in a 15-ml falcon tube (Becton Dickinson Labware, NJ), and subjected to refrigerated centrifugation at 4° C. and 3,000×G for 10 minutes, the supernatant was removed, then 5 ml of physiological saline was added to the precipitates (pellet), and the suspension was diluted 10 times with physiological saline to prepare a live cell suspension of each strain.

Further, 1 ml of the aforementioned live cell suspension was put into a 1.5-ml volume microtube (Eppendorf, Hamburg, Germany), and the tube was immersed into boiling water for 50 seconds and quenched. It was confirmed that each suspension immersed in boiling water did not form any colony on the standard agar medium (Eiken, Tokyo, Japan) to prepare injured cell suspensions of the coliform bacteria and Enterobacteriaceae bacteria.

The live cell suspensions and injured cell suspensions prepared as described above were used as test samples for the following tests.

The live cell counts of the coliform bacteria and Enterobacteriaceae bacteria in the live cell suspensions were counted on the standard agar medium, and turbidimetry was simultaneously carried out at a wavelength of 600 nm by using a spectrophotometer U-2800A (Hitachi, Japan) to figure out the relationship between the live cell count and the turbidity.
1-2) Ethidium Monoazide (EMA) Treatment and Light Irradiation Treatment Ethidium monoazide (EMA, Sigma, St. Louis, Mo.) was dissolved at 1000 μg/ml using sterilized water, and subjected to filtration sterilization by using 0.20-μm filter (Minisart-plus, Sartorius AG, Gottingen, Germany) to prepare a stock solution (EMA solution), which was stored at −20° C. under light shielding.

The EMA solution (1000 μg/ml) in a volume of 10 μl was added to each test sample (live cell suspension or injured cell suspension) in a volume of 1 ml, and the mixture was left at 4° C. for 10 minutes under light shielding.

Then, the test sample was set at a distance of 20 cm from a visible light source (100V PRF 500W Flood eye, Iwasaki Electric Co., Ltd., Tokyo, Japan), and irradiated with visible light for 5 minutes on ice.

The EMA-treated and visible light-irradiated test sample was subjected to refrigerated centrifugation at 4° C. and 15,000×G for 10 minutes, the supernatant was removed, then 1 ml of physiological saline was added to the pellet for washing, and the suspension was further subjected to refrigerated centrifugation to collect the precipitates. Such a washing treatment was repeated several times, and then 10 µl of sterilized water was added to the precipitates (cells) to suspend the cells in the sterilized water to prepare a sample for PCR amplification.

1-3) PCR Amplification

An agent comprising bovine serum albumin (BSA, Sigma), trisodium citrate dihydrate (TSC, Kanto Kagaku), and magnesium chloride hexahydrate (Nakarai-Tesque) in the compositions 1) to 3) mentioned below was added to each sample for PCR amplification, and a surfactant of 4) comprising sodium laurylsulfate (SDS, Nakarai-Tesque) was added to 5 µl of the sample for PCR amplification.

In the following descriptions, a combination consisting of the agent having the compositions of 1) to 3) and the surfactant of 4) may also be referred to as a pretreatment agent.

1) 2% BSA: 5 µl
2) 50 mM TSC: 1 µl
3) 100 mM $MgCl_2$: 1.5 µl
4) 0.05% SDS: 1 µl

For the PCR amplification, Primer F: forward primer 16S_10F for 16S rRNA gene detection (SEQ ID NO: 1), and Primer R: reverse primer 16S_1500R for 16S rRNA gene detection (SEQ ID NO: 2) were used as PCR primers.

Further, in order to maximize variation (primary differential peak) of the fluorescent substance amount depending on the temperature to perform high sensitivity detection in the melt analysis of the amplified products after the real-time PCR, a PCR buffer consisting of the following components a) to g) was prepared, and the PCR amplification was performed by adding this PCR buffer to the mixture of the sample for PCR amplification and the pretreatment agent.

a) Primer F (10 pmol/µl): 4 µl
b) Primer R (10 pmol/µl): 4 µl
c) Ex-Taq (5 U/µl, Takara-Bio): 0.5 µl (containing 0.005% Tween 20 and 0.005% Nonidet P-40)
d) 10×Ex-Taq Buffer (Takara-Bio): 5 µl
e) dNTP mixture (Takara-Bio): 4 µl
f) 10×SYBR Green I (BMA): 8 µl
g) Sterilized water: 16 µl Real-time PCR was performed according to the following PCR thermal cycle conditions by using a real-time PCR apparatus (iCycler iQ, Bio-Rad, Hercules, Calif.).

1) 4° C. for 3 minutes (1 cycle)
2) 94° C. for 30 seconds (1 cycle)
3) 94° C. for 20 seconds; 55° C. for 30 seconds; 72° C. for 90 seconds (50 cycles)
4) 95° C. for 3 minutes (1 cycle)

Then, according to the protocol of the melt analysis of the PCR amplified product (temperature was raised at intervals of 0.1° C. from 60° C., each temperature was maintained for 8 seconds, and this procedure was repeated 350 times in total up to the final temperature of 95° C.), the melting temperature of the PCR amplified product was measured.

As a positive control, live cell suspension of *Enterobacter sakazakii* (8 $log_{10}$ cells/ml) was used to perform PCR amplification in the same manner. Further, as a blank sample, the PCR buffer itself to which any test sample was not added was used to perform PCR amplification.

1-4) Gel Electrophoresis

2% Agarose gel (2% Seakem GTG agarose, FCM Bio-Products, Rockland, Me.) was prepared by using 0.5×TAE.

The PCR amplified product was applied in a volume of 10 µl to the agarose gel, and electrophoresis was performed.

The gel was stained with 1 µg/ml ethidium bromide solution, and observed as a densitograph, and the image thereof was captured and stored by using AE-6905H Image Saver HR (Atto Co., Japan).

2. Results

The results of the real-time PCR are shown in Table 2. Further, the results of the electrophoresis of the final PCR amplified products are shown in FIG. 1.

The meanings of the symbols used in FIG. 1 are as follows.

EMA+: EMA treatment (10 µg/ml, 10 minutes, 4° C. under light shielding)+visible light irradiation (5 minutes)
EMA−: No EMA treatment
PC: Positive control in which 8 $log_{10}$ cells/ml live cell suspension of *Enterobacter sakazakii* was used in a volume of 5 µl
NC: Negative control in which sterilized water was used instead of the DNA template
M: 100 bp DNA ladder
Injured cell: Injured cells prepared by immersing the live cell suspension in boiling water for 50 seconds was used.
The cell counts in the live cell suspensions of each strain is as follows.
*E. coli*: *Escherichia coli* DH5α (7.91±0.20 $log_{10}$ cells/ml)
*S. enteritidis*: *Salmonella enteritidis* IIP 604 (8.07±0.02 $log_{10}$ cells/ml)
*K. oxytoca*: *Klebsiella oxytoca* JCM1665 (8.38±0.08 $log_{10}$ cells/ml)
*C. koseri*: *Citrobacter koseri* JCM1658 (8.02±0.06 $log_{10}$ cells/ml)
*E. sakazakii*: *Enterobacter sakazakii* ATCC51329 (7.95±0.01 $log_{10}$ cells/ml)
*S. fonticola*: *Serratia fonticola* JCM1242 (7.47±0.01 $log_{10}$ cells/ml)
*B. aquilia*: *Budvicia aquilia* JCM3902 (6.98±1.50 $log_{10}$ cells/ml)
*R. aquatilis*: *Rahnella aquatilis* NBRC13544 (7.38±0.14 $log_{10}$ cells/ml)
*E. americana*: *Ewingella americana* JCM4911 (7.47±0.43 $log_{10}$ cells/ml)
*H. alvei*: *Hafnia alvei* JCM1666 (8.04±0.22 $log_{10}$ cells/ml)
*L. adecarboxylata*: *Leclercia adecarboxylata* JCM1667 (7.46±0.20 $log_{10}$ cells/ml)
*M. wisconsensis*: *Moellerella wisconsensis* JCM5894 (7.85±0.34 $log_{10}$ cells/ml)
*Y. regensburgei*: *Yokenella regensburgei* JCM2403 (8.03±0.13 $log_{10}$ cells/ml)
*P. agglomerans*: *Pantoea agglomerans* JCM1236 (7.67±0.78 $log_{10}$ cells/ml)
*B. agrestis*: *Buttiauxella agrestis* JCM1090 (7.76±0.00 $log_{10}$ cells/ml)
*K. ascorbata*: *Kluyvera ascorbata* JCM2107 (7.80±0.02 $log_{10}$ cells/ml)
*C. davisae*: *Cedecea davisae* JCM1685 (7.56±0.10 $log_{10}$ cells/ml).

TABLE 2

| Coliform bacteria/ Enterobacteriaceae bacteria | log₁₀ cells/ml | Live cell [a] | | Injured cell [b] | |
|---|---|---|---|---|---|
| | | 0 [c] | 10 [d] | 0 | 10 |
| Klebsiella oxytoca JCM1665 | 8.38 ± 0.08 | 19 ± 0.5 | 20 ± 1.3 | 20 ± 1.2 | n.d. [f] |
| Citrobacter koseri JCM1658 | 8.02 ± 0.06 | 18 ± 0.8 | 19 ± 0.7 | 19 ± 1.3 | n.d. |
| Escherichia coli DH5 α | 7.91 ± 0.20 | 22 ± 0.8 [e] | 23 ± 0.5 | 20 ± 1.3 | n.d. |
| Salmonella enteritidis IIP 604 | 8.47 ± 0.02 | 19 ± 1.4 | 19 ± 0.6 | 18 ± 0.8 | n.d. |
| Enterobacter sakazakii ATCC 51329 | 7.95 ± 0.01 | 17 ± 0.9 | 21 ± 3.2 | 20 ± 4.2 | n.d. |
| Serratia fonticola JCM 1242 | 7.47 ± 0.01 | 17 ± 1.6 | 20 ± 1.2 | 18 ± 1.1 | n.d. |
| Buclvicia aquilia JCM 3902 | 6.98 ± 1.50 | 16 ± 3.2 | 24 ± 1.7 | 15 ± 2.0 | n.d. |
| Rahnella aquatilis NBRC 13544 | 7.38 ± 0.14 | 20 ± 0.4 | 23 ± 0.0 | 21 ± 1.4 | n.d. |
| Ewingella americana JCM 4911 | 7.47 ± 0.43 | 15 ± 0.2 | 17 ± 0.4 | 17 ± 0.1 | n.d. |
| Hafnia alvei JCM1666 | 8.04 ± 0.22 | 17 ± 0.2 | 18 ± 1.6 | 16 ± 1.3 | n.d. |
| Leclerda adecarboxylata E1667 | 7.46 ± 0.20 | 13 ± 0.5 | 16 ± 1.0 | 16 ± 1.5 | n.d. |
| Moellerella wisconsensis JCM 5894 | 7.85 ± 0.34 | 15 ± 2.7 | 19 ± 5.6 | 16 ± 1.3 | n.d. |
| Yokenella regensburgei JCM 2403 | 8.03 ± 0.13 | 17 ± 0.2 | 16 ± 0.4 | 15 ± 0.4 | n.d. |
| Pantoea agglomerans JCM 1236 | 7.67 ± 0.78 | 15 ± 0.1 | 16 ± 1.5 | 16 ± 0.2 | n.d. |
| Buttiauxella agrestis JCM 1090 | 7.76 ± 0.00 | 13 ± 1.0 | 17 ± 1.1 | 18 ± 2.8 | n.d. |
| Kluyvera ascorbata JCM 2107 | 7.80 ± 0.02 | 17 ± 1.4 | 18 ± 0.8 | 18 ± 0.4 | n.d. |
| Cedecea davisae JCM 1685 | 7.56 ± 0.10 | 21 ± 1.4 | 24 ± 2.1 | 22 ± 1.4 | n.d. |

The symbols [a] to [f] used in Table 2 have the following meanings.
[a] Live cell counts of the coliform bacteria/Enterobacteriaceae bacteria numerical values in the columns mean Ct values in real-time PCR.
[b] Injured cells were prepared by immersing the live cell suspension in boiling water for 50 seconds.
[c] No treatment with EMA is meant.
[d] EMA final concentration of 10 μg/ml is meant.
[e] Ct value is indicated as mean ± SD (n = 2).
[f] n.d. means that PCR was performed twice, but the objective gene did not amplified in both PCRs.

As shown in the results of Table 2, the Ct values (number of cycles corresponding to rising of real-time PCR curve) of the EMA-untreated group of live cells were 13 to 22, and the Ct values of the EMA-treated group of live cells were 16 to 24. Further, the Ct values of the EMA-untreated group of injured cells were 15 to 22, and all the groups provided good PCR amplification results. However, in the EMA-treated groups of injured cells of all the coliform bacteria and Enterobacteriaceae bacteria, amplification of the target gene was not attained.

Furthermore, as shown in the results of the electrophoresis shown in FIG. 1, any band indicating positive result for the PCR amplified product could not be detected only for the EMA-treated groups of injured cells of all the coliform bacteria and Enterobacteriaceae bacteria.

On the basis of the above results, it became clear that, by carrying out the method of the present invention, distinction of live cells and injured cells as well as distinction of live cells and dead cells are enabled for 16 genera of coliform bacteria and 2 genera of the family Enterobacteriaceae. Further, distinction of live cells and injured cells was also made possible for species of which detection has conventionally been difficult, for example, Escherichia bacteria and Salmonella bacteria.

Example 3

Distinctions of live cells and injured cells of coliform bacteria and Enterobacteriaceae bacteria inoculated into a foodstuff, i.e., cow's milk, were performed.
1. Test Materials and Test Methods
1-1) Used Strains and Culture Method Bacteria of 1 genus of the family Enterobacteriaceae and 12 genera of the coliform bacteria, Kluyvera ascorbata JCM2107, Cedecea davisae JCM1685, Citrobacter koseri JCM1658, Klebsiella pneumoniae NRBC3321, Serratia fonticola JCM1242, Yokenella regensburgei JCM2403, Rahnella aquatilis NBRC13544, Hafnia alvei JCM1666, Leclercia adecarboxylata JCM1667, Pantoea agglomerans JCM1236, Enterobacter sakazakii ATCC51329, E. coli DH5α, and Salmonella enteritidis IID604 were cultured at 37° C. for 16 hours by using the Brain Heart Infusion Broth (BHI broth, Eiken Chemical Co., Ltd., Tokyo, Japan).

Each culture broth in a volume of 5 ml after the culture was collected in a 15-ml falcon tube (Becton Dickinson Labware, NJ), and subjected to refrigerated centrifugation at 4° C. and 3,000×G for 10 minutes, the supernatant was removed, then 5 ml of physiological saline was added to the precipitates (pellet), and the suspension was diluted 10 times with physiological saline to prepare a live cell suspension of each strain.

The live cell suspensions prepared as described above were used as test sample for the following tests.

The live cell counts of the coliform bacteria and Enterobacteriaceae bacteria in the live cell suspensions were counted on the standard agar medium, and turbidimetry was simultaneously carried out at a wavelength of 600 nm by using a spectrophotometer U-2800A (Hitachi, Japan) to figure out the relationship between the live cell count and the turbidity.
1-2) Inoculation of Bacterium Suspension to Foodstuff and Collection of Precipitates To 22.2 ml of marketed pasteurized cow's milk (live cells were not detected by the cultivation method), 9 to 25 cells were inoculated by using the live cell suspensions of various coliform bacteria and Enterobacteriaceae bacteria prepared above.

To 22.2 ml of the cow's milk, one kind of coliform bacterium or Enterobacteriaceae bacterium was inoculated.

Further, as a sample blank, 22.2 ml of cow's milk to which any live cell suspension was not added was prepared (bacterium not inoculated).

The cow's milk to which live cells of coliform bacterium Enterobacteriaceae bacterium was inoculated and the cow's milk to which any bacterium was not inoculated, as prepared above, were subjected to centrifugation at 37° C. and 3,000×G for 5 minutes, and the lipid layer on the surface of the supernatant and the aqueous layer existing as an interlayer were removed by decantation to collect the precipitates.

The collected precipitates (pellets) of the cow's milk to which live cells of coliform bacterium or Enterobacteriaceae bacterium was inoculated, and to which any bacterium was not inoculated both, contained dead cells of bacteria originally existed in the marketed cow's milk and made extinct by sterilization (gram-negative bacteria or gram-positive bacteria including coliform bacteria etc. (≥6 $\log_{10}$ cells)).

Therefore, it was judged that the precipitates prepared from the cow's milk to which live cells of the coliform bacterium or Enterobacteriaceae bacterium was inoculated contained dead cells and live cells.

1-3) Enzyme Treatment

To each of the precipitates (test sample) prepared from the cow's milk to which live cells of the coliform bacterium or Enterobacteriaceae bacterium as prepared above, 10 ml of the Brain Heart Infusion (BHI) broth kept warm at 37° C. beforehand was added, and the cells were suspended therein. To the suspension, 25 μl of a diluted enzyme solution prepared by diluting a proteinase K solution (equivalent to 1250 U/ml, EC.3.4.21.64, Sigma) 50 times with physiological saline (25 U/ml) was added to perform an enzyme treatment at 37° C. for 3 hours.

The enzyme-treated test sample was centrifuged at 37° C. and 3,000×G for 5 minutes, the supernatant was removed, and the precipitates were collected again.

1-4) Ethidium Monoazide (EMA) Treatment and Light Irradiation Treatment

After 1 ml of physiological saline was added to the precipitates after the enzyme treatment, and the mixture was stirred, 10 μl of an EMA solution (1000 μg/ml) prepared in the same manner as that of Example 2 was added to the mixture, and the mixture was left at 4° C. for 10 minutes under light shielding.

Then, visible light irradiation and washing treatment were performed in the same manner as that of Example 2, and 5 μl of sterilized water was added to the precipitates to prepare a sample for PCR amplification.

1-5) PCR Amplification

A pretreatment agent was added to 5 μl of the sample for PCR amplification as in Example 2.

For the PCR amplification, Primer F: forward primer 16S_1234F for 16S rRNA gene detection (5'-CTACAATG-GCGCATACAAAGAGAAG-3', SEQ ID NO: 3), and Primer R: reverse primer 23S_1703R for 23S rRNA gene detection (5'-CCTTCTCCCGAAGTTACGGCACCAT-3', SEQ ID NO: 4) were used as PCR primers.

Further, in order to maximize variation (primary differential peak) of the fluorescent substance amount depending on the temperature to perform high sensitivity detection in the melt analysis of the amplified products after the real-time PCR, a PCR buffer comprising the following components a) to g) was prepared, and PCR amplification was performed by adding 41.5 μl of this PCR buffer to the mixture of the sample for PCR amplification and the pretreatment agent.

The PCR primers contained the nucleotides of the 1234 to 1258 positions of the 16S rRNA gene, a tRNA gene (76 bp) and the nucleotides of the positions 1 to 1703 of the 23S rRNA gene, and the target thereof was a long DNA (about 2450 bp) containing a spacer region (about 364 bp).

a) Primer F (10 pmol/μl): 4 μl
b) Primer R (10 pmol/μl): 4 μl
c) Ex-Taq (5 U/μl, Takara-Bio): 0.5 μl (containing 0.5% Tween 20, 0.5% Nonidet P-40, and 50% glycerol)
d) 10×Ex-Taq Buffer (Takara-Bio): 5 μl
e) dNTP mixture (Takara-Bio): 4 μl
f) 10×SYBR Green I (BMA): 8 μl
g) Sterilized water: 16 μl Real-time PCR was performed according to the following PCR thermal cycle conditions by using a real-time PCR apparatus (iCycler iQ, Bio-Rad, Hercules, Calif.).

1) 95° C. for 3 minutes (1 cycle)
2) 95° C. for 30 seconds; 60° C. for 40 seconds; 68° C. for 3 minutes (40 cycles)
3) 95° C. for 3 minutes (1 cycle)

Then, according to the protocol of the melt analysis of the PCR amplified product (temperature was raised at intervals of 0.1° C. from 60° C., each temperature was maintained for 8 seconds, and this procedure was repeated 350 times in total up to the final temperature of 95° C.), the melting temperature of the PCR amplified product was measured.

As a positive control, 8 $\log_{10}$ cells/ml live cell suspension of *Enterobacter sakazakii* was used to perform PCR amplification in the same manner. Further, as a blank sample, the PCR buffer itself to which any test sample was not added was used to perform PCR amplification.

1-6) Gel Electrophoresis 0.8% Agarose gel (Seakem GTG agarose, FCM BioProducts, Rockland, Me.) was prepared by using 0.5×TAE.

The PCR amplified product in a volume of 5 to 10 μl was applied to the agarose gel to perform electrophoresis.

In a solution prepared by diluting SYBR Gold nucleic acid gel stain (Invitrogen, Eugene, Oreg., USA) 10,000 times with 0.5×TAE, the agarose gel after the electrophoresis was immersed for 15 minutes and thereby stained, then the gel was observed as a densitograph, and the image thereof was captured and stored by using AE-6905H Image Saver HR (Atto Co., Japan).

2. Results

The results of the real-time PCR are shown in Table 3. Further, the results of the electrophoresis of the final PCR amplified products are shown in FIG. 2.

Figure 2:
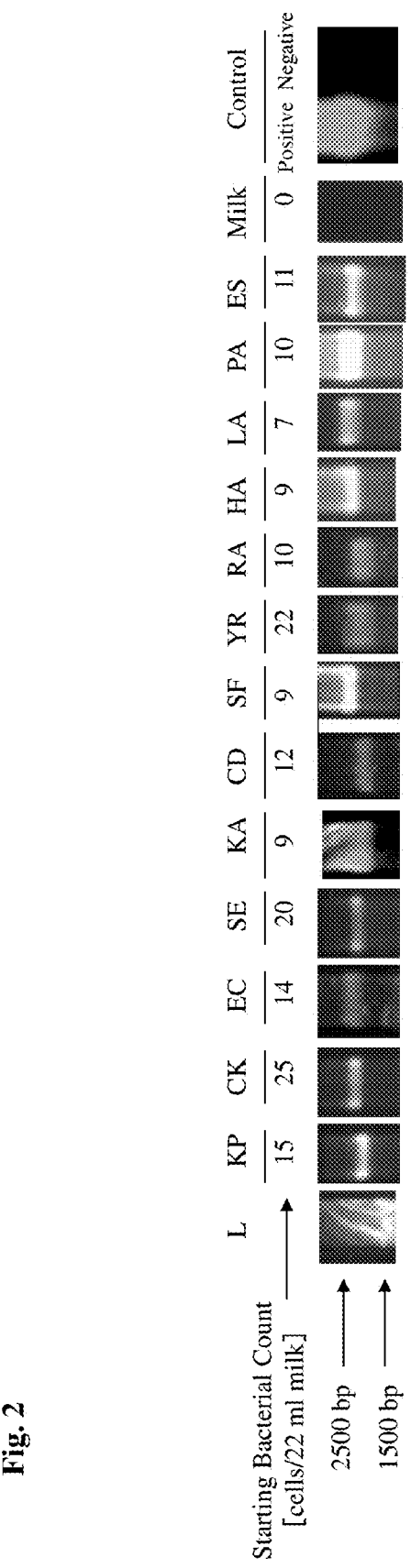

The meanings of the symbols used in FIG. 2 are as follows.

KP: *K. pneumoniae*
CK: *C. koseri*
EC: *E. coli*.
SE: *S. enteritidis*
KA: *K. ascorbata*
CD: *C. davisae*
SF: *S. fonticola*
YR: *Y. regensburgei*
RA: *R. aquatilis*
HA: *H. alvei*
LA: *L. adecarboxylata*
PA: *P. agglomerans*
ES: *E. sakazakii*
Milk: Marketed pasteurized cow's milk not inoculated with coliform bacterium
Positive: Positive control (*Enterobacter sakazakii*, 5 μl of 8 $\log_{10}$ CFU/ml was used as a template for PCR)
Negative: Negative control (5 μl of sterilized water was used as a PCR template)
L: 100 bp DNA ladder.

TABLE 3

| Coliform bacteria/Enterobacteriaceae bacteria | | Live cell count [a] [logCFU/sample] | | | Real time PCR | | | |
|---|---|---|---|---|---|---|---|---|
| | | | | | TM pattern [b] | | Electrophoresis/ gel staining [c] | |
| | | Initial | After incubation for 3 hours | Δ cell count | F = 5 | F = 10 | F = 5 | F = 10 |
| Klebsiella pneumoniae | NBRC 3321 | 1.4 ± 0.0 | 3.4 ± 0.2 | 2.0 | 4/4 | 4/4 | 4/4 | 4/4 |
| Citrobacter kosei | JCM 1658 | 1.4 ± 0.0 | 3.3 ± 0.1 | 1.9 | 2/2 | 1/2 | 2/2 | 1/2 |
| Kluyvera ascorbata | JCM 21070 | 1.2 ± 0.0 | 4.4 ± 1.1 | 3.2 | 2/2 | 2/2 | 2/2 | 2/2 |
| Escherichia coli | DH5 α | 1.1 ± 0.1 | 2.3 ± 0.1 | 1.2 | 2/2 | 1/2 | 2/2 | 2/2 |
| Cedecea davisae | JCM 1685 | 1.0 ± 0.1 | 2.7 ± 0.4 | 1.7 | 0/2 | 0/2 | 2/2 | 2/2 |
| Salmonella enteritidis | IID 604 | 1.4 ± 0.1 | 3.5 ± 0.2 | 2.1 | 2/2 | 1/2 | 2/2 | 2/2 |
| Serratia fonticola | JCM 1242 | 0.9 ± 0.1 | 2.3 ± 0.1 | 1.4 | 1/2 | 1/2 | 2/2 | 1/2 |
| Yokenella regensburgei | JCM 2403 | 1.0 ± 0.5 | 3.0 ± 0.4 | 2.0 | 2/2 | 2/2 | 2/2 | 2/2 |
| Rahnella aquatilis | NBRC 13544 | 1.0 ± 0.0 | 2.3 ± 0.4 | 1.3 | 1/2 | 2/2 | 2/2 | 2/2 |
| Hafnia alvei | JCM 1666 | 1.3 ± 0.1 | 3.3 ± 0.6 | 2.0 | 2/2 | 2/2 | 2/2 | 2/2 |
| Leclercia adecarboxylata | JCM 1667 | 0.8 ± 0.0 | 2.6 ± 0.3 | 1.8 | 2/2 | 2/2 | 2/2 | 2/2 |
| Pantoea agglomerans | JCM 1236 | 1.1 ± 0.3 | 2.2 ± 0.4 | 1.1 | 0/2 | 2/2 | 2/2 | 2/2 |
| Enterobacter sakazakii | ATCC 51329 | 1.2 ± 0.2 | 3.1 ± 0.2 | 1.8 | 8/8 | 8/8 | 8/8 | 8/8 |
| Average or tatal | | 1.1 ± 0.2 | 2.9 ± 0.6 | 1.8 ± 0.6 | 28/34 | 28/34 | 34/34 | 32/34 |

Meanings of the symbols a) to c) used in Table 3 are as follows.
a) Live cell counts of the coliform bacteria, the measurement was performed with n=2 to 8.
b) Number of positive results to the total number of the measurement of the amplified product by the melt analysis (TM pattern) based on real-time PCR
c) Number of positive results to the total number of the measurement of the PCR amplified product by the electrophoresis and gel staining (SYBR Gold) method.

From the results shown in Table 3, in the samples prepared by inoculating 9 to 25 cells of the various coliform bacteria (live cells) in 22.2 ml of pasteurized cow's milk, then centrifuging the milk, and performing a proteinase K treatment in the BHI broth and incubation (proliferation step of live coliform bacteria), the number of the coliform bacteria (live cells) increased to 90 to 2,900 cells.

Further, as a result of performing melt analysis of the PCR amplified products and electrophoresis of the PCR amplified products, it was possible to detect live cells for all the 13 strains. In addition, the PCR amplification product obtained from the cow's milk not inoculated with coliform bacteria (live cells) showed a negative result in both the melt analysis and the electrophoresis.

From the above results, it was revealed that it was made possible to detect live cells of coliform bacteria and Enterobacteriaceae bacteria inoculated into a foodstuff such as cow's milk by distinguishing them from dead cells (detection of live cells) by the method of the present invention. Therefore, it became possible to widely apply such distinction to foodstuffs such as cow's milk and detect live cells with high sensitivity, even for various cells for which distinction of live cells and dead cells have been difficult (bacteria, viruses, etc.).

Control Example 1

Detection of Live Cells by Conventional Method

High concentration of injured cells of coliform bacterium (also including Enterobacteriaceae bacteria cells) were detected by the EMA-PCR method targeting 16S rRNA (long DNA) in which cells were subjected to an EMA treatment, and then DNA was purified by DNA extraction and used as a template.

1. Test Materials and Test Methods
1-1) Used Strains and Culture Method
The method of this test was carried out according to the method of Japanese Patent No. 4217797 (International Patent Publication No. WO2002/052034).

*Escherichia coli* DH5α, *Salmonella enteritidis* IID604, *Klebsiella oxytoca* JCM1665, and *Citrobacter koseri* JCM1658 were cultured at 37° C. by using the Brain Heart Infusion Broth (BHI broth, Eiken, Tokyo).

A predetermined volume (10 ml) aliquot was collected from each culture broth in which the cells were in the logarithmic phase, and subjected to refrigerated centrifugation at 4° C. and 8,000×G for 15 minutes. After the supernatant was removed, 10 ml of physiological saline was added to the pellet to suspend the cells again, a similar washing operation was performed, then 10 ml of physiological saline was added to the pellet, and the resulting suspension was used as a live cell suspension. Live cell count was measured by using an L agar plate medium.

Injured cells were prepared by putting 1 ml of the live cell suspension into a 1.5-ml microtube, and immersing the microtube in boiling water for 50 seconds (injured cell suspension). The injured cells obtained by this treatment did not form colonies on a standard agar medium.

1-2) EMA Treatment and Light Irradiation Treatment of Bacteria
EMA (Sigma, St. Louis, Mo., USA) was dissolved at 1000 μg/ml using sterilized water, and subjected to filtration sterilization by using 0.20-μm filter (Minisart-plus, Sartorius AG, Gottingen, Germany).

The EMA solution (1000 μg/ml) in a volume of 10 μl was added to the live cell and injured cell suspensions (1 ml) of *E. coli* DH5α (7.91±0.20 $\log_{10}$ cells/ml), and left at 4° C. for 10 minutes under light shielding.

Then, the suspensions were placed at a distance of 20 cm from a visible light source (100V PRF 500W Flood eye, Iwasaki Electric Co., Ltd., Tokyo, Japan), and irradiated with light for 5 minutes on ice.

Each EMA-treated sample was subjected to refrigerated centrifugation at 4° C. and 15,000×G for 10 minutes, the supernatant was removed, and then a similar washing operation was performed with 1 ml of physiological saline.

The live cell suspensions and the injured cell suspensions of the *Salmonella enteritidis* IID604 (8.47±0.02 $\log_{10}$ cells/ml), *Klebsiella oxytoca* JCM1665 (8.38±0.08 $\log_{10}$ cells/ ml), and *Citrobacter koseri* JCM1658 (8.02±0.06 $\log_{10}$ cells/ml) were also subjected to the same EMA treatment as that used for the *E. coli* DH5α.

1-3) Extraction of DNA from Coliform Bacteria (Including Enterobacteriaceae Bacteria)

The supernatant of each suspension obtained after the EMA treatment was removed, then 0.5 ml of 10 mM Tris-HCl (pH 8.0) was added to the precipitates (cells), 10 µl of a Proteinase K solution (corresponding to 1,250 U/ml, Sigma) was added to the mixture, 200 µl of a 10% (w/v) SDS solution was added to the mixture, and the mixture was incubated overnight at 50° C.

Then, DNA extraction was performed by the phenol/chloroform extraction and ethanol precipitation method (EP).

Sterilized water in a volume of 150 µl was added to the extracted and purified DNA, and the concentration was estimated on the basis of the absorbance at UV 260 nm ($OD_{260}$). Further, purity was estimated on the basis of $OD_{260}/OD_{280}$.

1-4) Real-Time PCR

By using Primer F: forward primer 16S_10F for 16S rRNA gene detection (SEQ ID NO: 1), and Primer R: reverse primer 16S_1500R for 16S rRNA gene detection (SEQ ID NO: 2), a PCR buffer having the composition shown below was prepared.

The gel was stained with 1 µg/ml ethidium bromide solution, and observed as a densitograph, and the image thereof was captured and stored by using AE-6905H Image Saver HR (Atto Co., Japan).

2. Results

Ct values (number of PCR cycles at which the amplification curve exceeds a limit value) obtained by performing real-time PCR are shown in Table 4. Further, the results of the electrophoresis are shown in FIG. 3.

Figure 3:
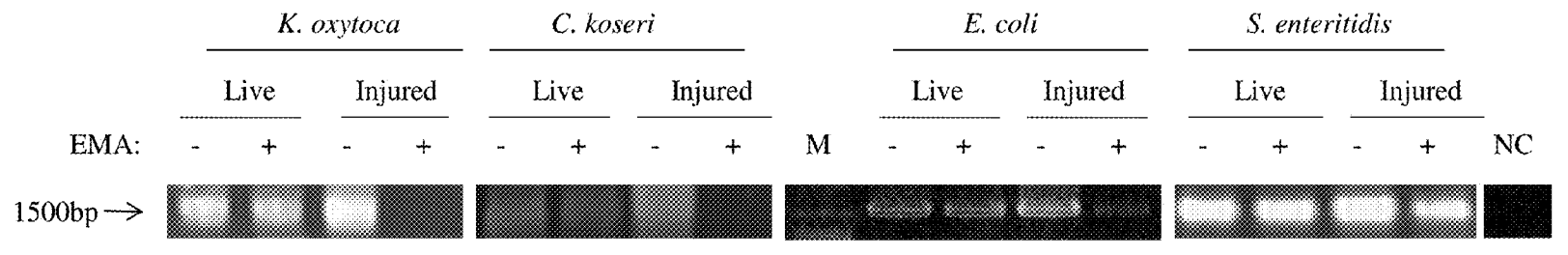

The meanings of the symbols used in FIG. 3 are as follows.

*Klebsiella* bacterium: *K. oxytoca* JCM1665 (8.38±0.08 $\log_{10}$ cells/ml)

*Citrobacter* bacterium: *C. koseri* JCM1658 (8.02±0.06 $\log_{10}$ cells/ml)

*Escherichia* bacterium: *E. coli* DH5α (7.91±0.20 $\log_{10}$ cells/ml)

*Salmonella* bacterium: *S. enteritidis* IIP604 (8.47±0.02 $\log_{10}$ cells/ml)

EMA+: EMA treatment (10 µg/ml, 10 minutes, 4° C. under light shielding)+visible light irradiation (5 minutes)

EMA−: No EMA treatment

NC: Negative control in which sterilized water was used instead of the DNA template M: 100 bp DNA ladder Injured cell: Injured cells prepared by immersing the live cell suspension in boiling water for 50 seconds.

TABLE 4

| Bacrerium | $\log_{10}$ cells/ml | Live cell [a] 0 [c] | Live cell [a] 10 [d] | Injured cell [b] 0 [e] | Injured cell [b] 10 |
|---|---|---|---|---|---|
| *Klebsiella oxytoca* JCM1665 | 8.38 ± 0.08 | 21 ± 0.9 | 22 ± 1.1 | 22 ± 1.0 | n. d. [f] |
| *Citrobacter koseri* JCM1658 | 8.02 ± 0.06 | 19 ± 0.7 | 21 ± 0.8 | 20 ± 1.1 | n. d. |
| *Escherichia coli* DH5 α | 7.91 ± 0.20 | 24 ± 1.2 | 25 ± 0.8 | 22 ± 1.4 | 40 ± 1.4 |
| *Salmonella enteritidis* IIP604 | 8.47 ± 0.02 | 21 ± 1.4 | 21 ± 0.5 | 20 ± 0.8 | 34 ± 1.1 | a) Ex-Taq (5 U/µl, Takara-Bio): 0.5 µl
b) 10×Ex-Taq Buffer (Takara-Bio): 5 µl
c) dNTP mixture (Takara-Bio): 4 µl
d) Primer F (10 pmol/µl): 4 µl
e) Primer R (10 pmol/µl): 4 µl
f) SYBR Green I (2×) (BMA): 10 µl
g) Sterilized water: 22.5 µl The template DNA in an amount equivalent to 150 ng was added to 50 µl of the aforementioned PCR buffer, and real-time PCR was performed according to the following PCR thermal cycle conditions by using a real-time PCR apparatus (iCycler iQ, Bio-Rad, Hercules, Calif.).

1) 4° C. for 3 minutes (1 cycle)
2) 94° C. for 30 seconds (1 cycle)
3) 94° C. for 20 seconds; 55° C. for 30 seconds; 72° C. for 90 seconds (50 cycles)
4) 95° C. for 3 minutes (1 cycle)

Then, according to the protocol of the melt analysis of the PCR amplified product (temperature was raised at intervals of 0.1° C. from 60° C., each temperature was maintained for 8 seconds, and this procedure was repeated 350 times in total up to the final temperature of 95° C.), the melting temperature of the PCR amplified product was measured.

1-5) Gel Electrophoresis

2% Agarose gel (2% Seakem GTG agarose, FCM Bio-Products, Rockland, Me.) was prepared by using 0.5×TAE.

The PCR amplified product was applied in a volume of 10 µl to the agarose gel, and electrophoresis was performed.

The symbols a) to f) used in Table 4 indicate the followings.

a) Live cell counts of the *Klebsiella* bacterium, *Citrobacter* bacterium, *Escherichia* bacterium, and *Salmonella* bacterium
numerical values in the columns mean Ct values obtained in real-time PCR.
b) Injured cells prepared by immersing the live cell suspension in boiling water for 50 seconds.
c) No treatment with EMA is meant.
d) EMA final concentration of 10 µg/ml is meant.
e) Ct value is indicated as mean±SD (n=2).
f) n.d. means that the PCR amplification reaction did not advance, and the Ct value could not be observed.

According to the results shown in Table 4, significant change of the Ct value was not provided in the real-time PCR by performing the EMA treatment for the live cells of *E. coli* and *S. enteritidis*. Further, in the case of the injured cells, the EMA-treated *E. coli* cells showed a higher Ct value of about 18, the EMA-treated *S. enteritidis* cells showed a higher Ct value of about 14, compared with those of the untreated cells, thus there was observed a tendency that the PCR amplification was suppressed, but PCR showed a positive reaction (Ct value: 40±1.4 and 34±1.1).

As seen from the results of distinction of live cells and injured cells using the final PCR amplified products (FIG. 3), the band of the objective gene was obtained also in the sample of EMA-treated injured cells for *E. coli* DH5α and *S. enteritidis* IID604, and thus distinction of live cells and injured cells could not sufficiently be confirmed.

On the other hand, as for the *Klebsiella* bacterium and the *Citrobacter* bacterium, when the live cells were subjected to the EMA treatment, any phenomenon concerning significant increase of the Ct value was not observed, but when the injured cells were subjected to the EMA treatment, the PCR amplification reaction was completely inhibited, thus the Ct value could not be measured, and therefore distinction of the live cells and injured cells was possible.

Example 4

It was examined how much degree the cells of *Enterobacter sakazakii* were lysed (lysis) in the presence of a pretreatment agent after 50 times of PCR thermal cycles.
1. Test Methods
Cells of *Enterobacter* Sakazakii ATCC51329 strain (ES) in an amount of $10^8$ cells/ml were suspended in physiological saline or the pretreatment agent solution mentioned in Table 5 (henceforth also referred to as "DB (direct buffer)") to prepare suspensions (0.25 mL). Each suspension was divided into 25 μl portions, and they were put into 200-μl PCR tubes, respectively, subjected to PCR thermal cycle repetition step using a cycle of 95° C. for 15 seconds, 60° C. for 20 seconds, and 72° C. 30 seconds (50 times), and combined into one again (total 0.25 ml) as a sample for PCR amplification. From the sample of 0.25 ml mentioned above, a portion of 2.5 μl was collected, and added to 12.25 μl of the pretreatment agent solution mentioned in Table 5 (provided that the volume of sterilized water was changed to 2.7 μl), and 12.75 μl of the PCR buffer mentioned below was added to the mixture to perform PCR (corresponding to the suspension I mentioned in Table 6). As the primers, ompA_F: forward primer for ompA gene detection (5'-ggatttaaccgtgaactttcc-3', SEQ ID NO: 7), and ompA_R: reverse primer for ompA gene detection (5'-cgccagcgatgtta-gaaga-3', SEQ ID NO: 8) were used.
Composition of PCR Buffer:
a) ompA_F (10 pmol/μl): 2 μl
b) ompA_R (10 pmol/μl): 2 μl
c) Ex-Taq (5 U/μl, Takara-Bio): 0.25 μl (containing 0.5% Tween 20, 0.5% Nonidet P-40, and 50% glycerol)
d) 10×Ex-Taq Buffer (Takara-Bio): 2.5 μl
e) dNTP mixture (Takara-Bio): 2 μl
f) 10×SYBR Green I (BMA): 4 μl Then, 247.5 μl of the remainder sample for PCR amplification (the sample for PCR amplification after the 2.5 μl portion was extracted from the volume of 0.25 ml) was subjected to refrigerated centrifugation (10,000×g, 5 minutes, 4° C.), and 12.25 μl of the pretreatment agent solution and 12.75 μl of the PCR buffer were added to 2.5 μl of the supernatant to perform PCR (supernatant I). Then, to the pellet obtained by the aforementioned centrifugation, 0.25 ml of physiological saline or the pretreatment agent solution mentioned in Table 5 was added to prepare suspensions, and to 2.5 μl of each suspension, 12.25 μl of the pretreatment agent solution and 12.75 μl of the PCR buffer were added to perform PCR (suspension II). The remainder of the suspension was subjected to refrigerated centrifugation under the same conditions as mentioned above, and to 2.5 μl of the supernatant, 12.25 μl of the pretreatment agent solution mentioned in Table 5 and 12.75 μl of the PCR buffer were added to perform PCR (supernatant II). Thereafter, the same procedure was repeated until the suspension IV and the supernatant IV were obtained, and PCR was performed with each of them.

Real-time PCR was performed according to the following PCR thermal cycle conditions by using a real-time PCR apparatus (iCycler iQ, Bio-Rad, Hercules, Calif.).
1) 4° C. for 3 minutes (1 cycle)
2) 95° C. for 15 seconds; 60° C. for 20 seconds; 72° C. for 30 seconds (50 cycles)
3) 95° C. for 3 minutes (1 cycle)

Then, according to the protocol of the melt analysis of the PCR amplified product (temperature was raised at intervals of 0.1° C. from 60° C., each temperature was maintained for 8 seconds, and this procedure was repeated 350 times in total up to the final temperature of 95° C.), the melting temperature of the PCR amplified product was measured.

TABLE 5

| Pretreatment agent solution (DB) | Amount (μL) | Final concentration |
| --- | --- | --- |
| 500 μg/mL lysozyme | 0.5 | 10 μg/mL |
| 4% Brij 58 | 6.25 | 1% |
| 2% BSA | 2.5 | 0.2% |
| 250 mM TSC | 0.1 | 1 mM |
| 750 mM MgCl$_2$ | 0.1 | 3 mM |
| 320 X SYBR Green I | 0.1 | 1.28 X |
| Sterilized water | 15.45 | — |
| Total | 25 | — |

2. Results
The results for the Ct values determined by the real-time PCR amplification are shown in Table 6. The indication "Not heated" in the table means a group for which the heat treatment according to the PCR thermal cycle (repeating 50 times a thermal cycle consisting of reactions at 95° C., 60° C. and 72° C.) was not performed, and "Heated with thermal cycle" means a group for which the heat treatment according to the PCR thermal cycle was performed 50 times. The live cell count of *Enterobacter sakazakii* in the suspension IV indicated with a) was $10^{7.6}$ cells/ml as determined on the standard agar medium plate, and the live cell count of *Enterobacter sakazakii* in the supernatant I indicated with b) was $10^{5.7}$ cells/ml as determined by the same method.

On the basis of the fundamental characteristic of this test, the measurement results of live cell counts in the suspension IV and supernatant I revealed that live cells were also contained at a ratio of 1% in the supernatant obtained by refrigerated centrifugation of the suspension of *Enterobacter sakazakii* in physiological saline. As for the non-heated group of *E. sakazakii* (in physiological saline), when the Ct values obtained for the suspension I or II and the supernatant I were compared, the Ct values for the suspension group were lower by about 5, and it is considered that this is mainly because the live cells were significantly collected in the precipitates (pellet), and an extremely small amount of them were also collected in the supernatant. That is, such a phenomenon means that the live cells were distributed between the precipitates and the supernatant at a specific ratio.

The results for the thermal cycle heated group of *E. sakazakii* (in physiological saline) means the test results obtained by subjecting the suspension of the live cells of *Enterobacter sakazakii* in physiological saline to the PCR thermal cycle 50 times, and then performing PCR amplification reaction with the supernatant and the pellet, and if the bacterial cells were lysed when the PCR thermal cycle was repeated, and the chromosomal DNA flew mainly out of the cells, it should basically become impossible to measure the Ct value for the suspensions II to IV. However, all of the Ct values were lower than 20, and thus the reactions of PCR were favorably performed. Thus, it was decided to determine how much degree *Enterobacter sakazakii* cells were lysed after they were subjected to 50 times of the PCR thermal cycles in physiological saline in the following examples.

TABLE 6

|  |  | Washing step | I | II | III | IV |
|---|---|---|---|---|---|---|
| *E. sakazakii* (in physiological saline) ($10^8$ cells/mL) | Not heated | Suspension | 16.4 ± 0.4 | 17.0 ± 0.6 | 17.0 ± 0.8 | 16.9 ± 0.5 [a)] |
|  |  | Supernatant | 21.5 ± 0.0 [b)] | 21.2 ± 0.5 | 23.2 ± 1.0 | 23.9 ± 1.2 |
|  | Heated with thermal cycle | Suspension | 14.3 ± 0.5 | 16.9 ± 0.4 | 18.0 ± 1.1 | 19.0 ± 0.8 |
|  |  | Supernatant | 15.2 ± 0.2 | 19.6 ± 0.6 | 20.6 ± 0.9 | 20.8 ± 1.2 |
| *E. sakazakii* (in DB) ($10^8$ cells/mL) | Not heated | Suspension | 15.8 ± 1.4 | 15.4 ± 0.7 | 15.7 ± 1.2 | 14.3 ± 0.9 |
|  |  | Supernatant | 23.9 ± 2.7 | 27.1 ± 0.8 | 25.5 ± 5.9 | 28.0 ± 1.4 |
|  | Heated with thermal cycle | Suspension | 22.4 ± 0.5 | 22.5 ± 0.4 | 22.4 ± 0.4 | 22.6 ± 0.2 |
|  |  | Supernatant | 30.7 ± 0.4 | 30.9 ± 0.8 | 30.7 ± 1.0 | 30.8 ± 1.2 |

Further, as for the *Enterobacter sakazakii* cells "not heated" in the presence of the pretreatment agent, the ratio of the *Enterobacter sakazakii* cells flown into the supernatant by the refrigerated centrifugation was suppressed 10 times compared with that obtained with physiological saline, i.e., the ratio was 0.1 to 0.2%, and the recovery efficiency as the pellet was markedly improved. If the *Enterobacter sakazakii* cells are lysed only by leaving them in the pretreatment agent solution, the Ct value significantly increases as the process proceeds from the step for the suspension I to the step for the suspension IV, and if they are completely lysed, the chromosomal DNA is recovered in the supernatant after the refrigerated centrifugation, and thus the measurement of the Ct value should become impossible. However, the results shown in Table 6 do not support such estimation.

What should be especially noted for the case where the *Enterobacter sakazakii* cells were subjected to 50 times of PCR thermal cycles in the pretreatment agent solution includes that the Ct value of the suspension I was smaller than the Ct value of the supernatant I by more than 8, that the Ct value of the suspension II is similarly smaller than the Ct value of the supernatant I by more than 8, and that the Ct values of the suspensions III and IV did not increase in spite of the increase of the number of washing operation of the pellet. If the *Enterobacter sakazakii* cells are completely lysed in the pretreatment agent solution during the repetition of the PCR thermal cycle, and the chromosomal DNA is completely flown out into the external solution, the Ct values of the suspension I and the supernatant I should be substantially the same values, and as the number of the washing of the pellet increases thereafter, the Ct value of the suspension should significantly increase, or the measurement thereof should become impossible. However, the results shown in Table 6 do not support such estimation. On the contrary, the Ct value of the suspension I was smaller than the Ct value of the supernatant I by more than 8, it is estimated that the ratio of the chromosomal DNA flown out into the supernatant was around 0.1 to 0.5% at most (as for the origin of Ct value of the supernatant I, an extremely small part of the *Enterobacter sakazakii* cells of which specific gravity became smaller due to the repetition of the thermal cycle may be recovered in the supernatant), and it is estimated that 99% or more of the origin of the Ct value of the suspension I is DNA in the cells of *Enterobacter sakazakii*. That is, it was suggested that even after the *Enterobacter sakazakii* cells were subjected to the PCR thermal cycle 50 times in the presence of the pretreatment agent, 99% or more of them were not lysed.

Further, the Ct values of the suspension I and the supernatant I of the "Not heated" group of *E. sakazakii* (in DB) shown in Table 6 are significantly smaller than those of the "Heated with thermal cycle" group, respectively. Supposing that most of the cells of *Enterobacter sakazakii* were lysed by 50 times of PCR thermal cycles in the presence of the pretreatment agent, and the chromosomal DNA moved to the solution side, the Ct values of the suspension I and the supernatant I of the "Heated with thermal cycle" group should be comparable. Further, in the suspension II, since *Enterobacter sakazakii* cells were in a state that they did not have the chromosomes, and therefore the cells should come to the state that the Ct value could not be measured. However, the results shown in Table 6 do not support such estimation. Furthermore, on the hypothesis that the Ct values of the aforementioned suspension I and the supernatant I in the "Not heated" group significantly smaller than those of the "Heated with thermal cycle" group were provided by denaturation due to the 50 times of the PCR thermal cycles, because proteins such as egg white lysozyme and bovine serum albumin were contained in the pretreatment agent, the experiment shown in Table 7 was further performed. The specific experimental procedure is shown below.

Ten portions of 25 µl of the pretreatment agent solution having the composition shown in Table 5 were prepared, subjected to 50 times of PCR thermal cycles, and combined to prepare 250 µl of the pretreatment agent solution subjected to the heating with thermal cycle. Then, a pellet of live cells (washed) of the *Enterobacter sakazakii* ATCC51329 strain obtained from 50 µl of a culture broth in which the cells were precultured overnight was added to physiological saline, a pretreatment agent solution or a pretreatment agent solution subjected to the heating with thermal cycle, at a density of $10^6$ to $10^9$ cells/ml, and suspended therein (50 µl of each suspension was prepared). Each suspension in a volume of 2.5 µl was added to 12.25 µl of the pretreatment agent solution mentioned in Table 5 (provided that the volume of sterilized water was changed to 2.7 µl), and 12.75 µl of the PCR buffer was further added to perform PCR (measurement was performed twice). The results are shown in Table 7.

TABLE 7

| E. sakazakii live cell (cells/mL) | Physiological saline | Pretreatment agent solution (DB) | |
|---|---|---|---|
| | | Not heated | Heated with thermal cycle |
| $10^9$ | 16.8 ± 0.5 | 15.8 ± 0.4 | 16.8 ± 0.8 |
| $10^8$ | 17.4 ± 0.7 | 16.2 ± 0.3 | 15.5 ± 0.7 |
| $10^7$ | 19.9 ± 0.2 | 19.9 ± 0.5 | 20.6 ± 0.6 |
| $10^6$ | 22.7 ± 1.1 | 24.0 ± 0.7 | 24.0 ± 0.8 |

It cannot be considered that the Ct value of the live cells of *Enterobacter sakazakii* suspended in the pretreatment agent solution and subjected to the heating with thermal cycle was significantly larger than the Ct value obtained with physiological saline or the pretreatment agent solution not subjected to the repetition of the thermal cycle, and thus it was confirmed that it could not be the cause of at least the increase of both the Ct values of the suspension I and the supernatant I of the "Heated with thermal cycle" group shown in Table 6. On the basis of these results, it is estimated that the chromosomal DNA in the cells of *Enterobacter sakazakii*, which was obtained by subjecting the *Enterobacter sakazakii* cells to 50 times of the PCR thermal cycles in the presence of the pretreatment agent, cooling them to 4° C., then returning them to room temperature, and subjecting them to refrigerated centrifugation so as to recover the chromosomal DNA in the pellet and the supernatant, was intricately twisted around denatured DNA binding proteins and denaturation enzymes, and could not function as a template for PCR at the beginning. Even if the Ct value of the supernatant I originated in that less than 1% of the *Enterobacter sakazakii* cells were lysed by 50 times of the PCR thermal cycles in the presence of the pretreatment agent, it is thought that DNA was not completely separated into single strands in the PCR thermal cycle treatment at 94° C. at the beginning of PCR for the aforementioned reason.

Example 5

It was evaluated whether the cells of *Enterobacter sakazakii* were lysed (lysis) by 50 times of PCR thermal cycles in the presence of the pretreatment agent, by using samples obtained before and after the repetition of the PCR thermal cycles on the basis of fluorescence microscopy and stereoscopic microscopy using a nuclear staining agent, and flow cytometry, which enables quantification of cells remaining after the repetition of the PCR thermal cycles.

A. Fluorescence Microscopy and Stereoscopic Microscopy
1. Experimental Methods

In the same manner as that of the method of Example 4, $10^9$ cells/ml of the cells of the *Enterobacter* Sakazakii ATCC51329 strain (ES) were suspended in physiological saline or the pretreatment agent solution mentioned in Table 5 to prepare suspensions (0.25 mL). Each suspension was divided into 25 μl portions and put into 200 μl PCR tubes, respectively, and subjected to a PCR thermal cycle repetition step (95° C. for 15 seconds, 60° C. for 20 seconds, and 72° C. 30 seconds, 50 times), and then the portions were combined into one again (total 0.25 ml). Each suspension was divided into halves, and supernatants were collected from one of them as it was and the other one subjected to refrigerated centrifugation (3000×g, 10 minutes, 4° C.). To 0.125 ml of each of the aforementioned suspensions and supernatants that underwent each process, SYTO9 was added at a ratio of 1.5 μl/ml, the mixture was maintained at 4° C. for 15 minutes under light shielding, and 2.5 μl of the mixture was placed on slide glass, covered with cover glass, set on a fluorescence/stereoscopic microscope AxiosKop2 motplus (lens: Plan-NEOFLUAR 100×/1.30 oil ∞/0.17, light source: KublercoDIX ebq 100 isolated, software: Axio-Vision Rel. 4.6.3, filter: FITC and DIC3, exposure time: FITC 347 ms fixed; DIC3 20 ms fixed, LEJ Leistungs elektronik Jena GmbH, Germany), and observed to confirm whether the bacterial cells emitted green fluorescence of 530 nm with argon laser light of 488 nm as an excitation light.

2. Results

Fluorescence microscopy images of the suspensions of *Enterobacter sakazakii* in physiological saline not heated or subjected to 50 times of PCR thermal cycles, and supernatants obtained by refrigerated centrifugation thereof, as well as the suspensions of *Enterobacter sakazakii* in the pretreatment agent solution not heated or subjected to 50 times of PCR thermal cycles, and supernatants obtained by refrigerated centrifugation thereof are shown in FIGS. 4 to 11, respectively. That is, the experiments were performed so that the fluorescence microscopy images should correspond to the suspension I to the supernatant I of the washing step I mentioned in Table 6. With these images, stereoscopic microscopy images, and superposed images of the stereoscopic microscopy images and fluorescence microscopy images are also shown.

Figure 4:
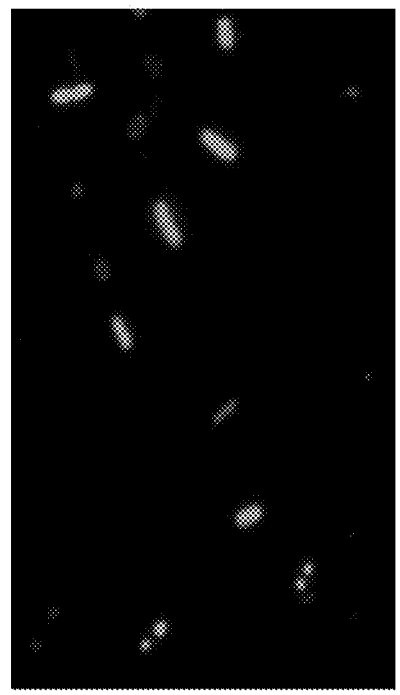
Figure 4:
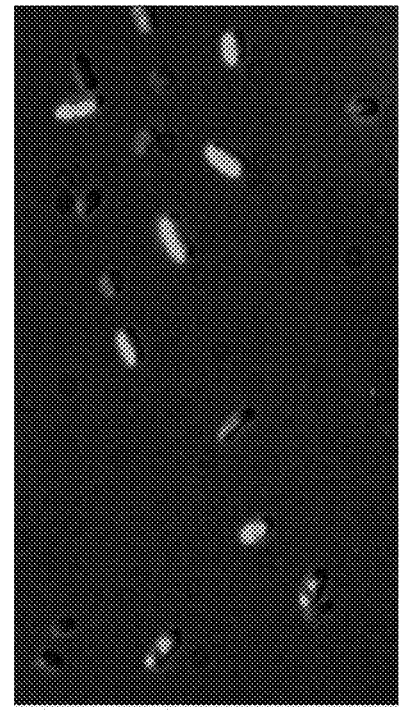
Figure 4:
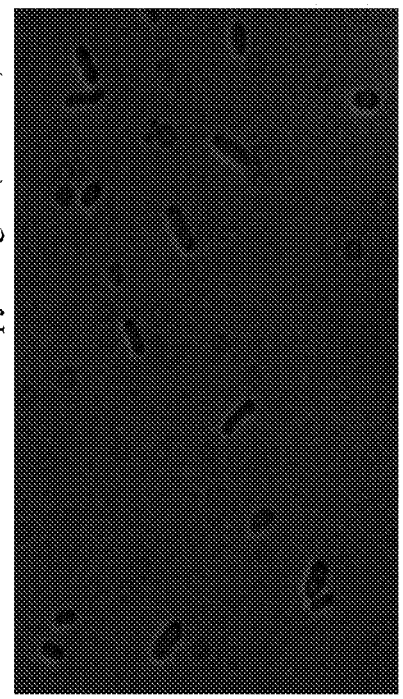
Figure 5:
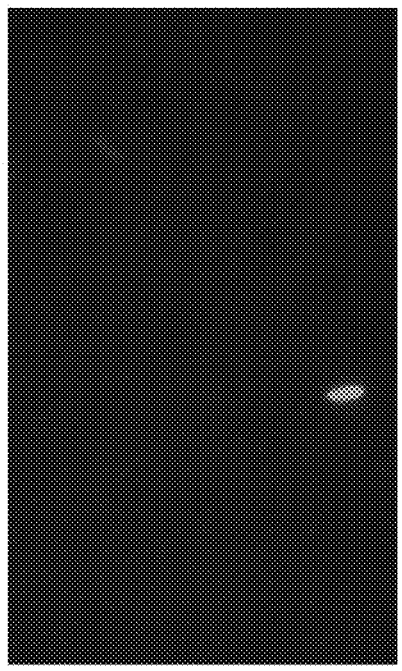
Figure 5:
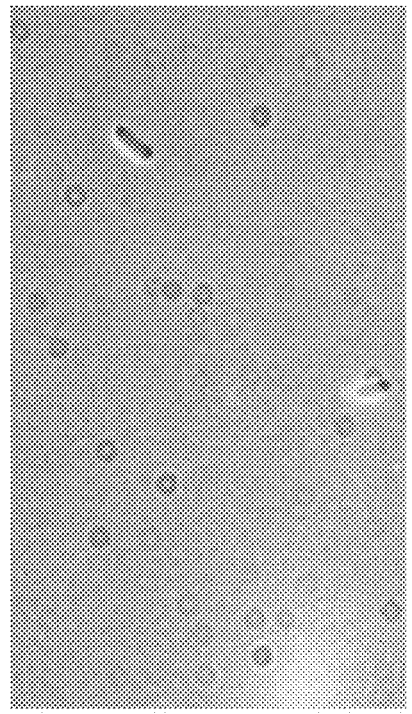
Figure 5:
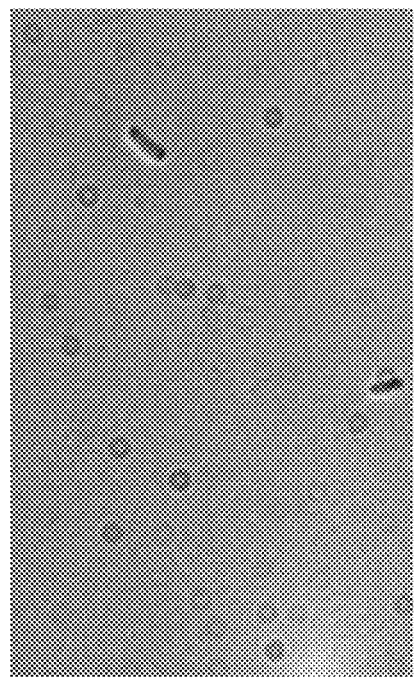
Figure 6:
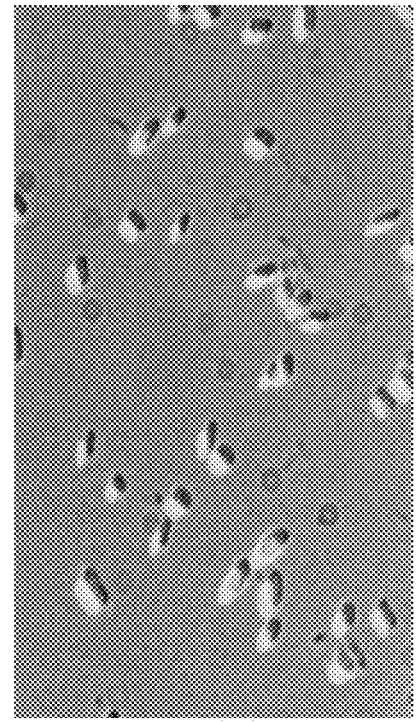
Figure 6:
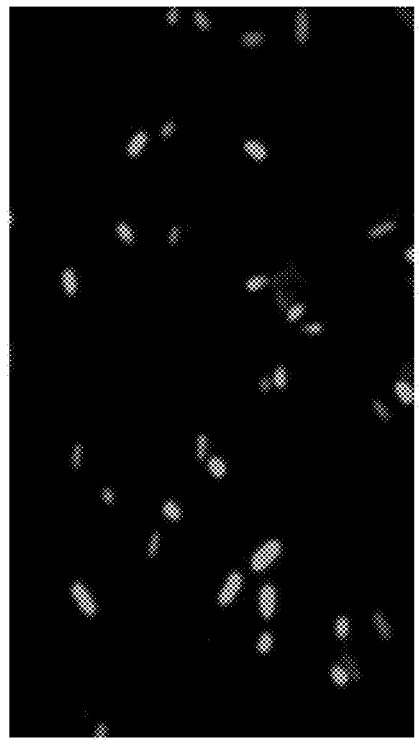
Figure 6:
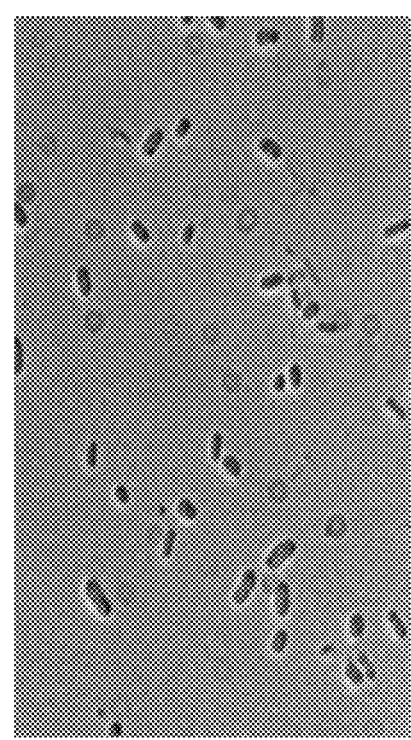
Figure 7:
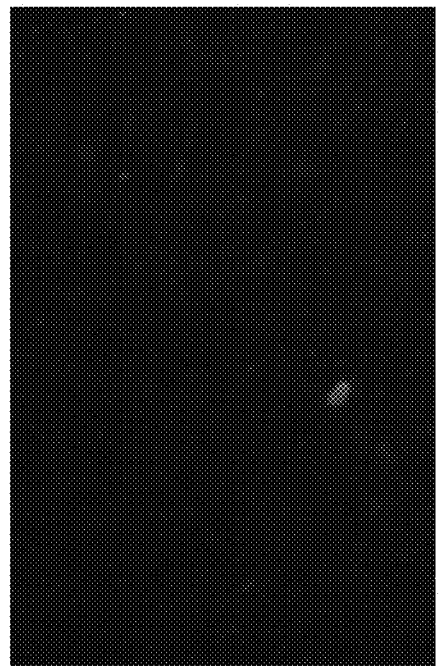
Figure 7:
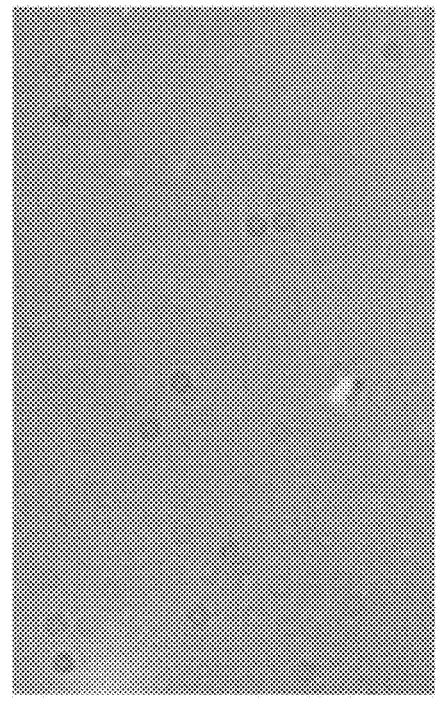
Figure 7:
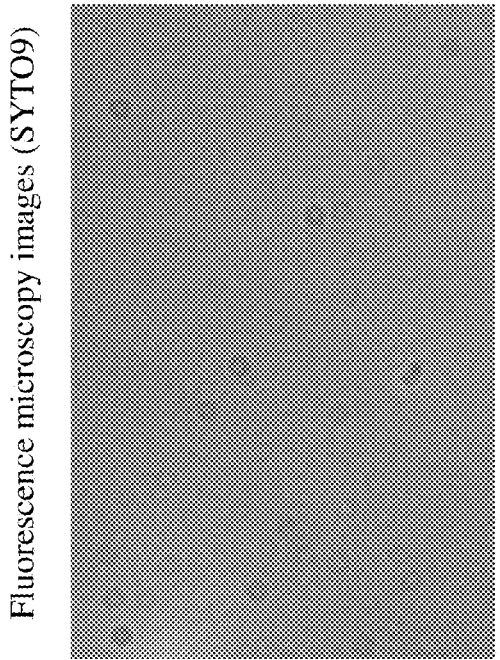

Regardless of use or disuse of the thermal cycle step, bacterial cells of *Enterobacter sakazakii* were also found in the centrifugation supernatant of the physiological saline suspension of *Enterobacter sakazakii*, and it also correlated with the results of PCR shown in Table 6. As shown in FIGS. 4 and 6, even if the cells of *Enterobacter sakazakii* were subjected to 50 times of the PCR thermal cycles in physiological saline, most of them maintained the bacterial cell morphology (stereoscopic microscopy image and fluorescence microscopy image), clear SYTO9 staining images were obtained, and therefore it was considered that the cells harbored the chromosomal DNA in the cells. Since cell wall debris were not found in the stereoscopic microscopy image shown in FIG. 6, a possibility was suggested that the small difference of the Ct values of the suspension I and the supernatant I of the thermal cycle heated group of the physiological saline suspension of *Enterobacter sakazakii* shown in Table 6 was not mainly due to flowing out of DNA into the aqueous phase caused by lysis of the cells of *Enterobacter sakazakii*, but it was observed because the specific gravity of the *Enterobacter sakazakii* cells became small due to 50 times of the PCR thermal cycles, and the ratio of the *Enterobacter sakazakii* cells recovered in the supernatant increased (this was also suggested by the results of the quantification by flow cytometry shown in FIG. 12 explained later).

Figure 8:
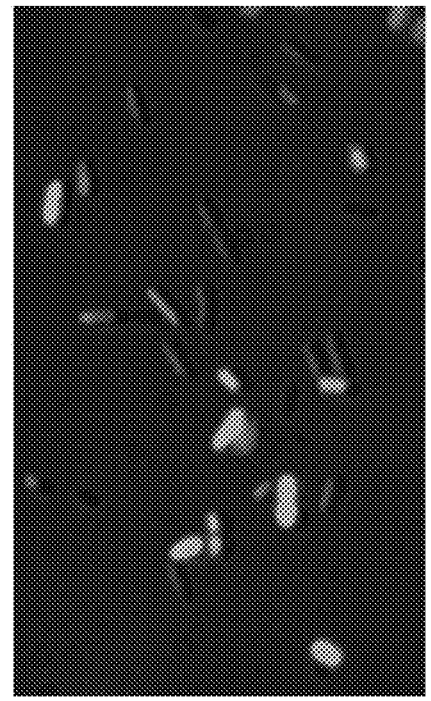
Figure 8:
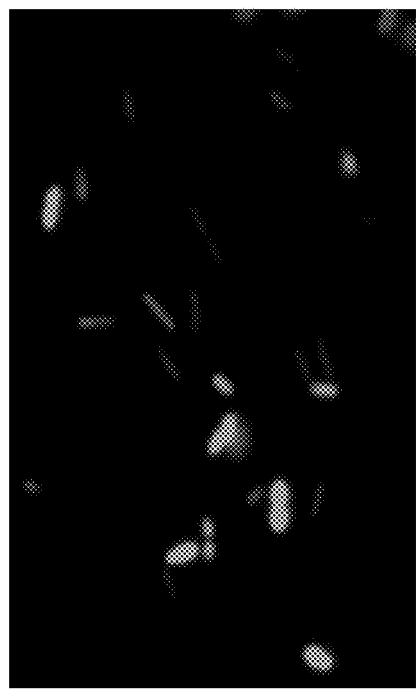
Figure 8:
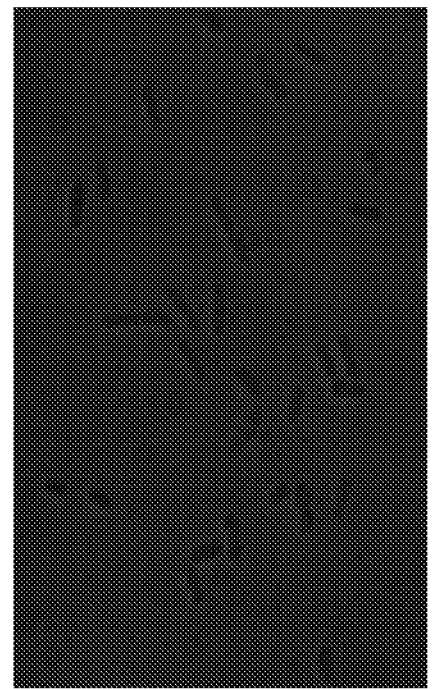
Figure 9:
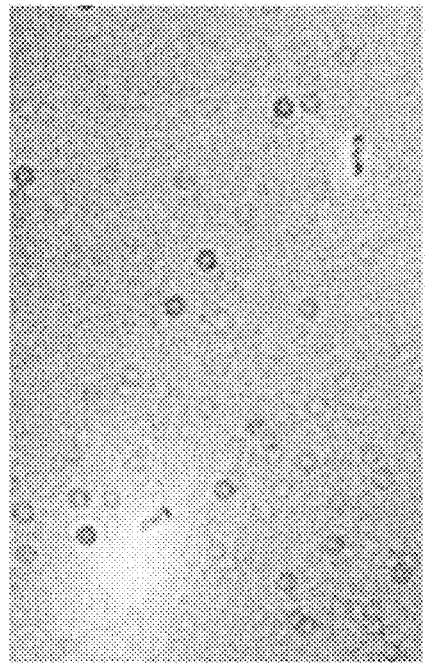
Figure 9:
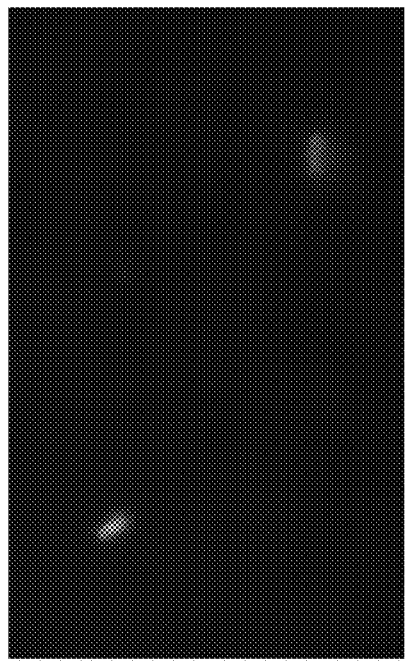
Figure 9:
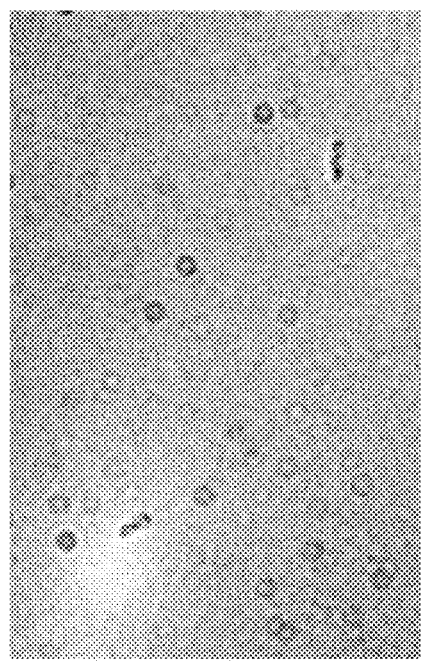
Figure 10:
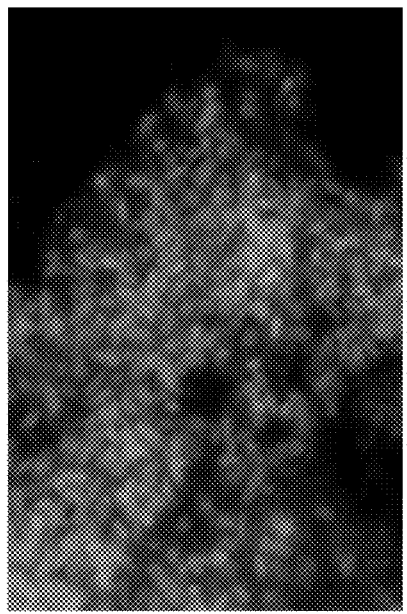
Figure 10:
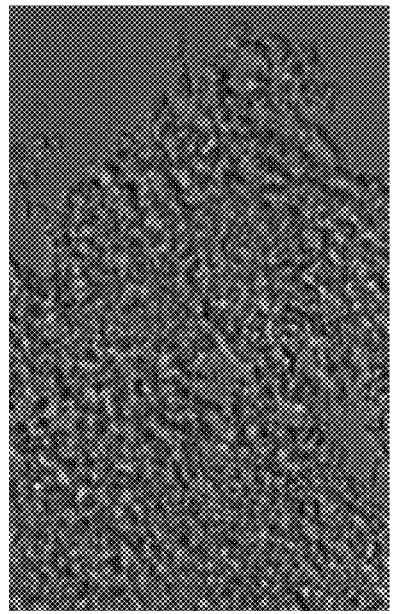
Figure 10:
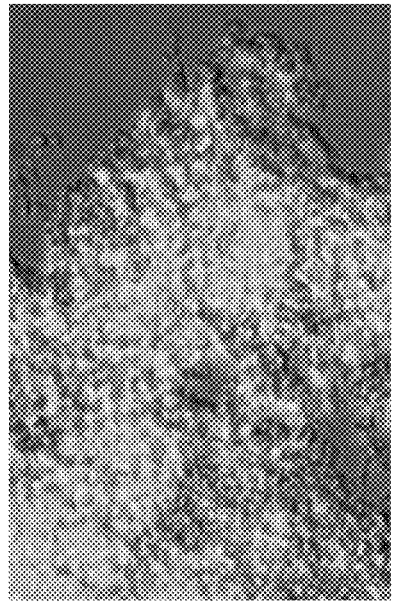
Figure 11:
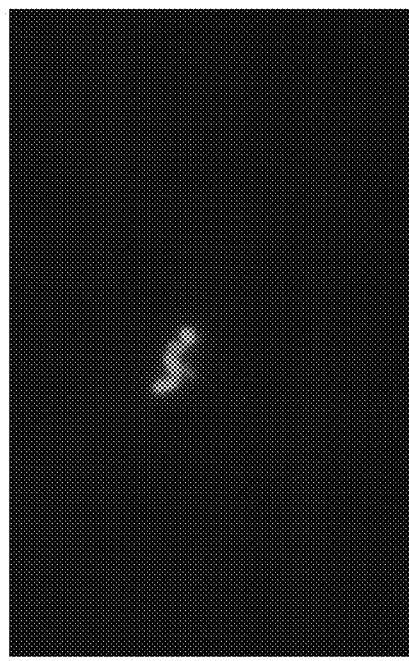
Figure 11:
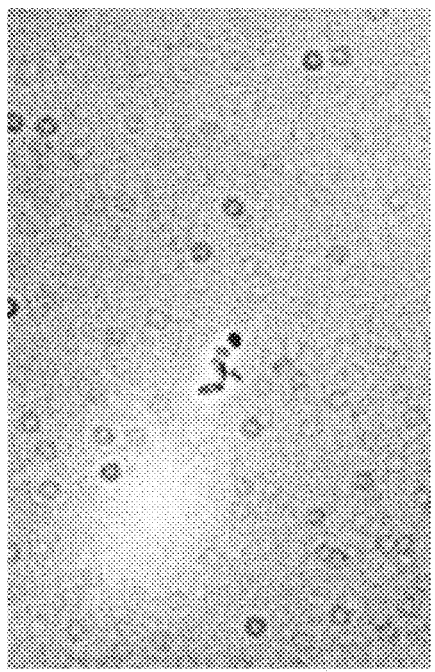
Figure 11:
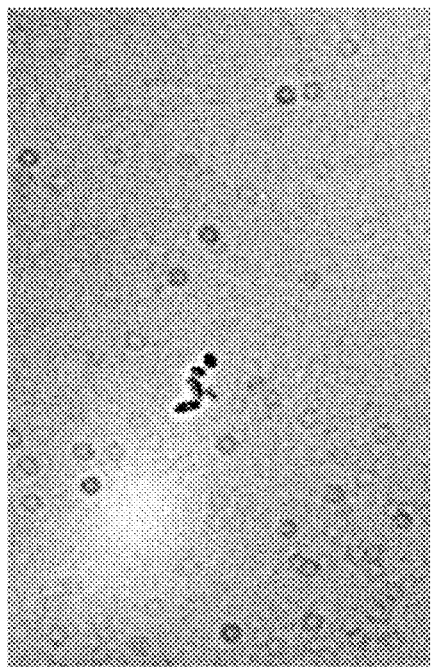

Further, as shown in FIGS. 8 and 10, lysis of the *Enterobacter sakazakii* cells themselves was not observed after 50 times of the PCR thermal cycles in the presence of the pretreatment agent, as in the case of physiological saline suspension, and it was considered that the *Enterobacter sakazakii* cells harbored the chromosomal DNA in the cells. However, as a marked difference from the case of using physiological saline, there was observed a phenomenon that the *Enterobacter sakazakii* cells coagulated after 50 times of the PCR thermal cycles were performed in the presence of the pretreatment agent, but lysis of the bacterial cells was not observed.

B. Flow Cytometry
1. Experimental Methods

The experimental methods for flow cytometry are shown below. First, in the same manner as that of the method of Example 4, $10^9$ cells/ml of the cells of the *Enterobacter* Sakazakii ATCC51329 strain (ES) were suspended in physiological saline or the pretreatment agent solution mentioned in Table 5 to prepare suspensions (0.25 mL). Each suspension was divided 25 μl portions and put into 200 μl PCR tubes, respectively, and subjected to a PCR thermal cycle repetition step (95° C. for 15 seconds, 60° C. for 20 seconds, and 72° C. 30 seconds, 50 times), and the portions were combined into one again (total 0.25 ml). Since suspension and supernatant thereof of each sample are used for the flow cytometry, three portions in a volume of 0.25 ml each were prepared for each sample. Specifically, the first portion consisted of the sample per se, the second portion was prepared by subjecting the sample to refrigerated centrifugation (3000×g, 10 minutes, 4° C.), then removing the supernatant, and adding 0.25 ml of physiological saline to the precipitates to suspend the cells therein, and the third portion consisted of a supernatant obtained by refrigerated centrifugation of the sample similar to the above. To each portion, SYTO9 was added at a concentration of 1.5 μl/ml, and the mixture was stored at 4° C. for 15 minutes under light shielding, and used as a test sample for flow cytometry.

The measurement apparatus was FACS Calibur (BECTON DICKINSON), and an argon laser of 488 nm was used to recognize bacterial cell plots by FSC (forward scattering light measurement) and SSC (side scattering light measurement). If SYTO9 intercalated into the intracellular chromosomal DNA, green fluorescence could be detected with an FL1 filter of which λmax is 530 nm by excitation with that laser, and therefore FL1 plotting was also performed. Although any nuclear staining agent based on propidium iodide (PI) was not especially used, red fluorescence was also measured with an FL3 filter for reference. The details of the measurement conditions of the flow cytometry are shown in Table 8.

TABLE 8

| Parameter | Detection | Voltage | Amp-Gain | Mode |
|---|---|---|---|---|
| p1 | FSC | E02 | | log |
| p2 | SSC | 427 | | log |
| p3 | FL1 | 542 | | log |
| p4 | FL2 | 647 | | log |
| p5 | FL3 | 633 | | log |
| p6 | FL1-A | | 1.00 | lin |
| p7 | FL1-W | | 1.00 | lin |

DDM Param: FL1

2. Results

Figure 12:
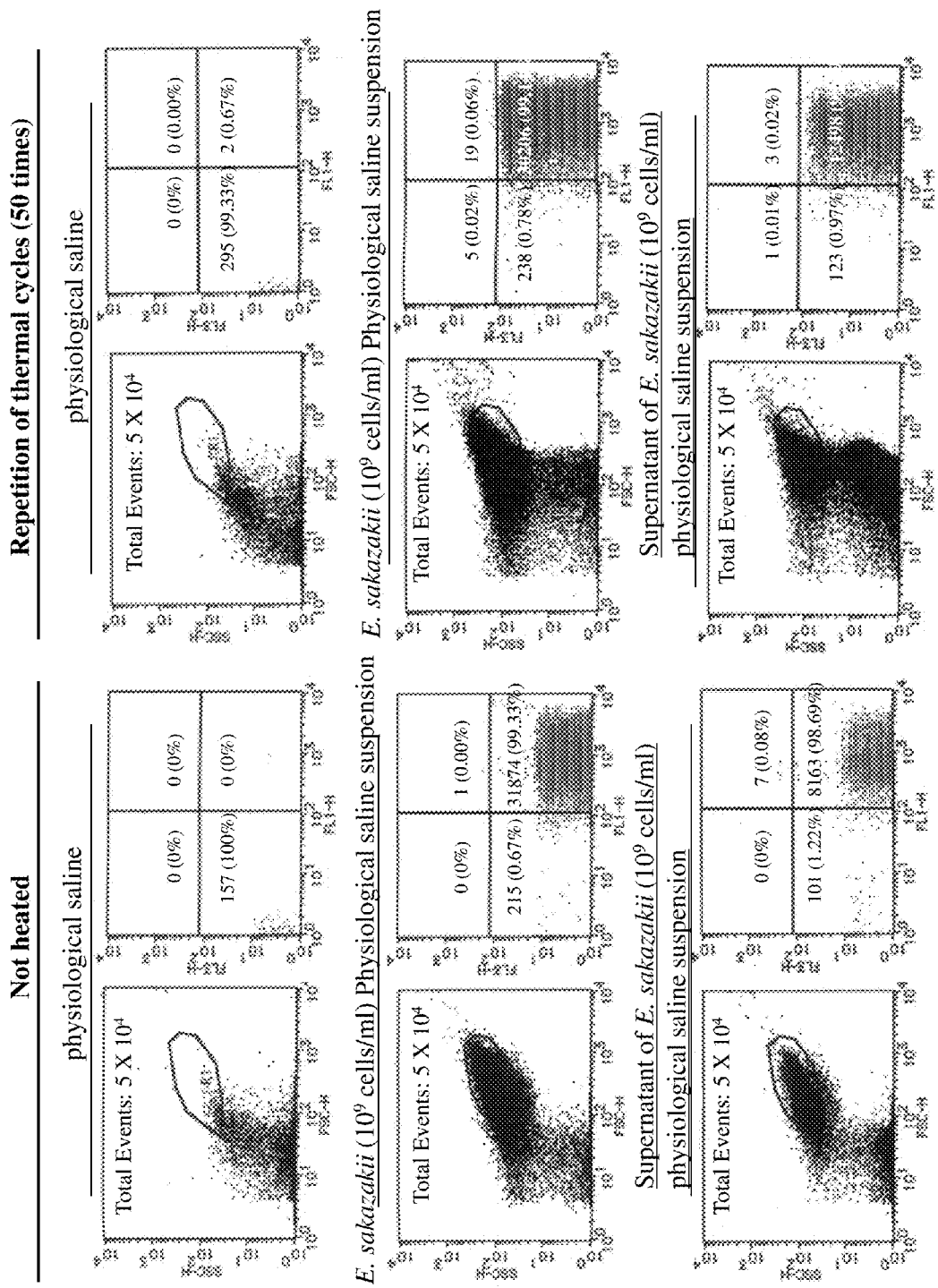
Figure 13:
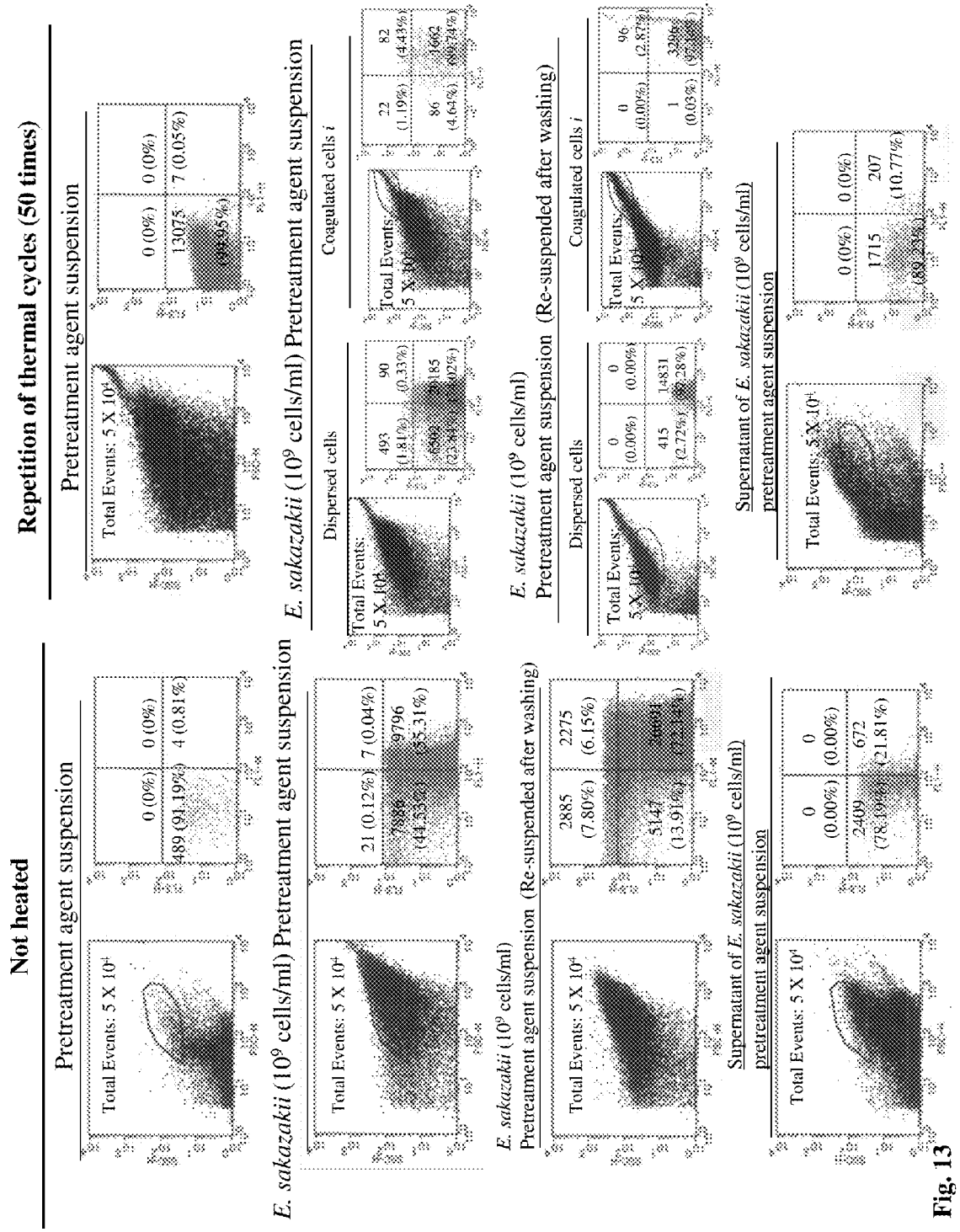

The experimental results for the physiological saline suspension of the *Enterobacter sakazakii* cells and the supernatant thereof (not heated or treated with repetition of PCR thermal cycles) are shown in FIG. 12, and the experimental results for the bacterium suspended in the pretreatment agent solution (including re-suspended suspension after washing once) and the supernatant thereof (not heated or treated with repetition of PCR thermal cycles) are shown in FIG. 13. As for the physiological saline suspension of the *Enterobacter sakazakii* cells, if most of the cells were lysed by 50 times of the PCR thermal cycles, they were divided into small portions, and were not included in the bacterium gate region (the region surrounded by the polygon is a region where bacteria are plotted) of the FSC-SSC chart, and nothing was plotted in the FL1 (FL1-H in the drawing) positive (+) region (right half field with respect to the X-axis), which means green fluorescence by SYTO9 thereafter, or plots therein should markedly decrease. However, the results for the samples of the physiological saline suspension of *Enterobacter sakazakii* cells not heated or subjected to the repetition of PCR thermal cycles shown in FIG. 12 do not support such estimation. On the contrary, even from the simple comparison of numerical values, it is estimated that 95% of the cells maintained bacterial morphology even after the thermal cycles, and also harbored the chromosomal DNA. If the intrinsic standard deviation for the results of two or more times of flow cytometry measurements is taken into consideration, the numerical difference is highly possibly within the range of measurement error, and it can be considered that substantially 100% of the bacterial cells of *Enterobacter sakazakii* maintained the morphology after 50 times of the PCR thermal cycles, and harbored the chromosomal DNA.

Similarly, on the basis of the results for *Enterobacter sakazakii* cells suspended in the pretreatment agent solution (not heated or treated with repetition of PCR thermal cycles) and the suspension obtained by washing and re-suspending the cells (not heated or subjected to PCR thermal cycles) of the *Enterobacter sakazakii* cells, shown in FIG. 13, it is hard to consider that the bacterial cells of *Enterobacter sakazakii* were lysed in the presence the pretreatment agent. On the basis of comparison of the results shown in FIGS. 12 and 13, it is easily estimated that the SYTO9 staining is somewhat inhibited in the presence of the pretreatment agent. Therefore, it is appropriate that the plots for *Enterobacter sakazakii* suspended in the pretreatment agent solution (not heated or subjected to thermal cycles, dispersed cells) at an FL1-H intensity (SYTO9) of $10^1$ to $10^3$ shown in FIG. 13 are regarded as the plots derived from the *Enterobacter sakazakii* cells. On such a premise, it is obvious that the bacterial cells of *Enterobacter sakazakii* were not lysed on the basis of the data for *Enterobacter sakazakii* cells suspended in the pretreatment agent solution not heated or subjected to PCR thermal cycles, but as for the data for *Enterobacter sakazakii* cells suspended in the pretreatment agent solution (obtained by washing and re-suspending the cells) not heated or subjected to PCR thermal cycles, supplementation is needed. In such a case, as a major premise, since the *Enterobacter sakazakii* SYTO9 staining plots were obtained for the cells once washed and re-suspended in physiological saline, they must be evaluated by using the FL1-H (+) region. In this case, although the total of the numbers of plots in the FL1-H(+) region for the "dispersed cells" and "coagulated cells" after the PCR thermal cycles apparently still smaller than that for the cells not heated, if it is taken into consideration that 1 μlot of the "coagulated *Enterobacter sakazakii* cells" is considered to highly possibly consist of at least several to several tens of *Enterobacter sakazakii* bacterial cells as estimated from the result shown in FIG. 10, it is inferred that the number is equivalent to or higher than that for the cells not heated, and if the data obtained without washing are also taken into consideration in combination, it is considered that substantially 100% of the bacterial cells of *Enterobacter sakazakii* were not lysed.

Example 6

Real-Time PCR Measurement Using Number of Bacterial Cells of *Enterobacter sakazakii* and Purified Chromosomes in the Same Amount of Chromosomal DNA Contained in the Cells 1. Experimental Methods From culture broths of *Enterobacter sakazakii* ATCC29544 and ATCC51329 strains in which the cells were proliferated overnight, purified DNA free from contamination of RNA was obtained according to the DNA extraction method described in WO2007/094077, absorbance values thereof were measured at 260 nm and 280 nm ($OD_{260}$ and $OD_{280}$, $OD_{260}$=1.0 for 50 µg/ml DNA solution, cell length: 1 cm), the DNA concentration was calculated from $OD_{260}$, and purity of the purified DNA was estimated on the basis of $OD_{260}/OD_{280}$.

Furthermore, the cells of the aforementioned culture broths in which the cells were proliferated overnight were washed, and then serially diluted with sterilized water to prepare live cell suspensions of Enterobacter sakazakii at densities of $4 \times 10^3$ to $4 \times 10^8$ cells/ml. Then, according to the method of Example 4, 2.5 µl of each suspension was added to 12.25 µl of the pretreatment agent solution mentioned in Table 5 (provided that the volume of sterilized water was changed to 2.7 µl), and 12.75 µl of the PCR buffer for detection of ompA gene was further added to the mixture to perform PCR in the same manner as that of Example 4. Each PCR tube contained $10^1$ to $10^6$ cells of Enterobacter sakazakii. Since the amount of chromosomal DNA obtained from 1 cell of Enterobacter sakazakii can be regarded 5 fg ($5 \times 10^{-15}$ g), the amount of chromosomal DNA contained in each PCR tube was calculated by using that value, and the same amount of the aforementioned purified DNA (2.5 µl) was put into each PCR tube, and the pretreatment agent solution and the PCR buffer were successively added in the same manner to perform PCR.

2. Results

Purification degrees of DNA are shown in Table 9, and the results of real-time PCR are shown in Table 10. As seen from the results shown in Table 9, the values of $OD_{260}/OD_{280}$ were around 2.0, and therefore high purity DNA with little contamination of RNA could be prepared from each of the two strains of Enterobacter sakazakii, respectively. Further, as seen from the results shown in Table 10, no significant difference was seen in the Ct values for bacterial cells of Enterobacter sakazakii bacterium and the chromosomal DNA in amounts corresponding to the same number of the cells, and thus it was found that if 100% of the purified DNA dissolved in the tube functioned as a template of PCR, 100% of the chromosomal DNA of the bacterial cells of Enterobacter sakazakii also functioned as a template for PCR.

As for the case of suspending the cells of Enterobacter sakazakii in a similar pretreatment agent solution or physiological saline (or sterilized water) and then adding such a PCR buffer as shown in Example 4 to the suspension to perform PCR, it is inferred that there may be a misunderstanding according to conventional knowledge that a part of the cells of Enterobacter sakazakii are lysed so that the chromosomal DNA flows out into the external solution, and serves as a template of PCR to cause the reactions of PCR. However, if this hypothesis is applied to this case, it is necessary that substantially 100% of the Enterobacter sakazakii cells should be lysed, but it is obvious that such a 100% lysis phenomenon is denied by the experimental results of Examples 4 and 5. That is, as for Example 4, in the comparison of the Ct values of the suspensions I and II and the supernatant I of the Enterobacter sakazakii cells after 50 times of the PCR thermal cycles in the presence of the pretreatment agent shown in Table 6, if 100% of the cells were lysed, the Ct value of the supernatant I needs to be significantly smaller than the Ct value of the suspension II, and the Ct value of this supernatant should be equivalent to that of the suspension I. However, the results shown in Table 6 do not support such estimation. Further, as for Example 5, on the basis of the results of the quantification of cell numbers of Enterobacter sakazakii before and after the repetition of the PCR thermal cycles shown in FIG. 13, which are the results of the flow cytometry measurement, lysis of substantially 100% of the cells is impossible, and even lysis of 10% of the cells is also improbable. That is, the hypothesis that "a part of bacterial cells are lysed, and chromosomal DNA flows out therefrom to the external solution to induce PCR" according to the general scientific knowledge cannot be applied to at least PCR in the presence of the pretreatment agent (50 times) according to the present invention.

TABLE 9

| Purified DNA of E. sakazakii after RNAse treatment | $OD_{260}$ | $OD_{280}$ | $OD_{260}/OD_{280}$ |
|---|---|---|---|
| ATCC29544 | 0.1108 | 0.0538 | 2.0595 |
| ATCC51329 | 0.1082 | 0.0540 | 2.0037 |

TABLE 10

| E sakazakii live cell (cells/PCR tube) | | $10^6$ | $10^5$ | $10^4$ | $10^3$ | $10^2$ | $10^1$ |
|---|---|---|---|---|---|---|---|
| ATCC29544 | DNA | $21.2 \pm 0.6$ [3)] | $24.0 \pm 0.9$ | $27.1 \pm 0.8$ | $31.2 \pm 0.9$ | $34.2 \pm 1.6$ | $41.3 \pm 5.4$ |
| | Cell | $20.7 \pm 0.2$ | $23.9 \pm 0.1$ | $27.7 \pm 0.1$ | $31.0 \pm 0.1$ | $34.3 \pm 0.4$ | $38.3 \pm 0.8$ |
| ATCC51329 | DNA | $19.1 \pm 0.8$ | $22.1 \pm 0.9$ | $25.3 \pm 1.0$ | $29.5 \pm 1.1$ | $32.5 \pm 1.4$ | $37.3 \pm 2.1$ |
| | Cell | $17.2 \pm 0.5$ | $20.6 \pm 0.4$ | $24.9 \pm 0.3$ | $28.6 \pm 0.1$ | $32.1 \pm 0.8$ | $37.1 \pm 2.0$ |

Example 7

From the results of Examples 4 to 6, it was found that most of the Enterobacter sakazakii cells were not lysed even after the reactions of PCR (50 times) with the PCR buffer in the presence of the pretreatment agent, and the cells harbored the chromosomal DNA in the cells. On the other hand, in the TM pattern analysis of the PCR amplified products after the real-time PCR (melting temperature measurement), a thermal peak estimated to be that of the ompA gene product was obtained, and it had judged to be positive for the real-time PCR. However, to be precise, it was not certain whether the PCR amplified product existed in the bacterial cells, in the reaction solution for PCR, or in the both. From a commonsense point of view, it is considered that the PCR amplified product is mainly dissolved in the solution for PCR, but even this is not definitely clarified, and for the PCR in the presence of the pretreatment agent according to the present invention, it was still less clarified. In the aforementioned example, it is suggested that the PCR in the presence of the pretreatment agent might be carried out in the bacterial cells, but in the following examples, a possibility that the PCR amplified product remains also in the bacterial cells will be demonstrated.

1. Experimental Methods

Five portions of 500 μl of culture broth of the *Enterobacter sakazakii* ATCC51329 strain ($9.3 \times 10^8$ cells/ml) in which the cells were proliferated overnight were prepared, and subjected to refrigerated centrifugation (3000×g, 10 minutes, 4° C.), the supernatant was removed, and then 500 μl of a common fixation solution A for bacteria (4% paraformaldehyde), or a fixation solution B (methanol/acetic acid=3/1), fixation solution C (Mildform 10N, 10% formalin, Neutral Buffer Solution Deodorized, Wako Pure Chemical Industries, Osaka), or fixation solution D (Mildform 10NM, 10% formalin, Neutral Buffer-Methanol Solution Deodorized, Wako Pure Chemical Industries, Osaka) was added to the pellet, and the mixture was incubated overnight at 4° C., so that the chromosomal DNA in the bacterial cells and cell wall proteins were crosslinked to fix the chromosomal DNA in the cells beforehand. As a control, a sample in which the fixation is not performed was prepared by using 500 μl of physiological saline instead of the fixation solution.

Then, the cells were washed three times with 500 μl of physiological saline, and finally suspended in 250 μl of physiological saline. Since recovery ratio of bacteria as a pellet after washing operation is generally considered 80%, and the centrifugation was performed 4 times, the estimated cell density of *Enterobacter sakazakii* in the final preparation was $7.6 \times 10^8$ cells/ml. Such a suspension in physiological saline in a volume of 250 μl was further diluted 10 times. The estimated cell density of *Enterobacter sakazakii* in this dilution was $7.6 \times 10^7$ cells/ml. This dilution in a volume of 2.5 μl was used as a sample for PCR amplification, and added to 12.25 μl of the pretreatment agent solution mentioned in Table 5 (provided that the volume of sterilized water was changed to 2.7 μl), and 12.75 μl of the PCR buffer for detection of gram-negative bacteria mentioned below was further added to the mixture. Portions in a volume of 27.5 μl were prepared in a number of 20 for each sample fixed with each fixation solution. As the primers, the forward primer 16S_1234F for 16S rRNA gene detection (SEQ ID NO: 3), and the reverse primer 23S_1703R for 23S rRNA gene detection (SEQ ID NO: 4) mentioned in Example 3 were used.

Composition of PCR buffer:
a) 16S_1234F (10 pmol/μl): 2 μl
b) 23S_1703R (10 pmol/μl): 2 μl
c) Ex-Taq (5 U/μl, Takara-Bio): 0.25 μl (containing 0.5% Tween 20, 0.5% Nonidet P-40, and 50% glycerol)
d) 10×Ex-Taq Buffer (Takara-Bio): 2.5 μl
e) dNTP mixture (Takara-Bio): 2 μl
f) 10×SYBR Green I (BMA): 4 μl Real-time PCR was performed according to the following PCR thermal cycle conditions by using a real-time PCR apparatus (iCycler iQ, Bio-Rad, Hercules, Calif.).

1) 4° C. for 3 minutes (1 cycle)
2) 95° C. for 15 seconds; 60° C. for 20 seconds; 72° C. for 3 minutes (30 cycles)
3) 95° C. for 3 minutes (1 cycle)

Then, according to the protocol of the melt analysis of the PCR amplified product (temperature was raised at intervals of 0.1° C. from 60° C., each temperature was maintained for 8 seconds, and this procedure was repeated 350 times in total up to the final temperature of 95° C.), the melting temperature of the PCR amplified product was measured.

After completion of PCR, the 20 portions of the PCR reaction solution for each fixation solution were combined into one, and subjected to refrigerated centrifugation (3000× g, 10 minutes, 4° C.). The supernatant was collected in a volume of 5 μl and used in 0.8% agarose gel electrophoresis (SYBR Gold staining, gel staining was performed by SYBR Gold staining for all the following cases), and the remaining supernatant was discarded. To the pellet, 200 μl of physiological saline was added to suspend the cells. The estimated bacterial cell count of *Enterobacter sakazakii* in the suspension was $1.5 \times 10^7$ cells/ml. SYTO9 was added to the suspension at a concentration of 1.5 μl/ml, and the mixture was left at 4° C. for 15 minutes under light shielding, and used to perform flow cytometry under the same conditions as those of Example 5. As a control, the same procedure was performed provided that PCR was performed for 0 cycle, not 30 cycle, to obtain a control sample.

Furthermore, for the samples obtained with the fixation solutions A and B, PCR was performed by using the ompA_F primer (SEQ ID NO: 7) and the ompA_R primer (SEQ ID NO: 8) described in Example 4 instead of 16S_1234F and 23S_1703R, the PCR thermal cycle conditions of Example 4, and the method of Example 7 except for the foregoing conditions, electrophoresis was performed for 5 μl of the supernatant obtained after PCR, and flow cytometry measurement was performed by using SYTO9 for a physiological saline suspension of the pellet obtained by removing the supernatant after PCR.

2. Results

Figure 14:
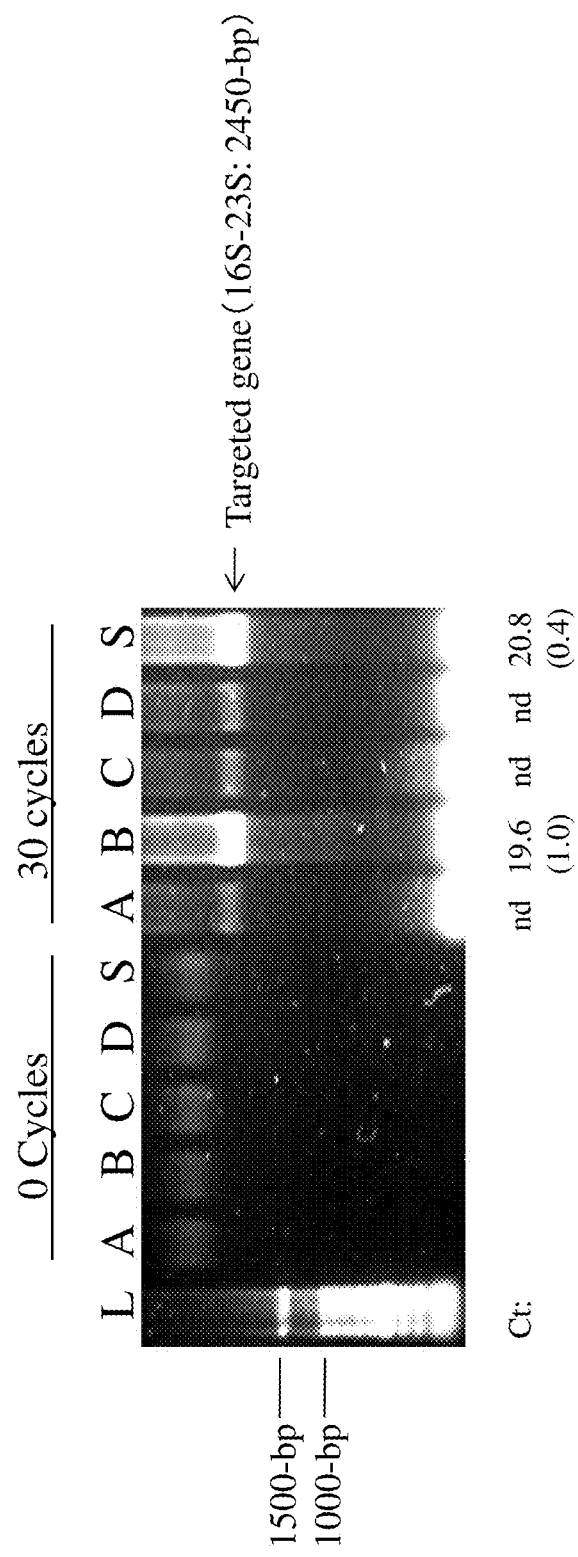

The results of the electrophoresis of the reaction supernatants after each of the aforementioned fixation solution treatments and PCR (16S-23S rRNA, 2450 bp) are shown in FIG. 14, and the Ct values of the corresponding reaction solutions determined in the real-time PCR are shown immediately below them. The results of the flow cytometry measurement performed by using SYTO9 for suspensions obtained by removing the supernatants of the samples after PCR, and suspending the pellets in physiological saline are shown in Table 11. The electrophoresis images of the supernatants after PCR targeting the ompA (469 bp) gene are similarly shown in FIG. 15. The results of the flow cytometry measurement performed by using SYTO9 for suspensions obtained by removing the supernatants of the samples after PCR, and suspending the pellets in physiological saline are shown in Table 12. As seen from the results shown in FIG. 14, the amount of the 16S-23S gene (2450 bp) product in the PCR mixture supernatant obtained with the fixation solution B was significantly larger than those obtained with the other fixation solutions, and the band strength was equivalent to that obtained without fixation ("S" in the drawing). Since, as a standard fixation method of bacteria, use of the fixation solution A is common, and the fixation solutions C and D also have a composition similar to that of the fixation solution A, it is considered that the chromosomal DNA in the cells of *Enterobacter sakazakii* and the cell wall proteins were firmly crosslinked. On the basis of the results shown in FIG. 14, it is appropriate to consider that the fixation solution B may have only a function equivalent to no fixation (S), but since the fixation solution B firmly crosslinks mammalian cell chromosomes and cell membrane proteins, it somewhat exhibits the fixation function also in bacteria.

TABLE 11

| FixA 0 cycles | Quad | Events | % Gated | %Total | FixB 0 cycles | Quad | Events | % Gated | % Total |
|---|---|---|---|---|---|---|---|---|---|
| Syto9 | UL | 0 | 0.00 | 0.00 | Syto9 | UL | 0 | 0.00 | 0.00 |
| Total Events 50000 | UR | 12 | 0.15 | 0.02 | Total Events 50000 | UR | 1 | 0.03 | 0.00 |
| Gated Events 7844 | LL | 292 | 3.72 | 0.58 | Gated Events 3761 | LL | 296 | 7.87 | 0.59 |
|  | LR | 7540 | 96.12 | 15.08 |  | LR | 3464 | 92.10 | 6.93 |
| FixA 30 cycles | Quad | Events | % Gated | % Total | FixB 30 cycles | Quad | Events | % Gated | % Total |
| Syto9 | UL | 0 | 0.00 | 0.00 | Syto9 | UL | 0 | 0.00 | 0.00 |
| Total Events 50000 | UR | 0 | 0.00 | 0.00 | Total Events 50000 | UR | 0 | 0.00 | 0.00 |
| Gated Events 7816 | LL | 1054 | 13.49 | 2.11 | Gated Events 7905 | LL | 1930 | 24.41 | 3.86 |
|  | LR | 6762 | 86.51 | 13.52 |  | LR | 5975 | 75.59 | 11.95 |
| FixC 0 cycles | Quad | Events | % Gated | % Total | FixD 0 cycles | Quad | Events | % Gated | % Total |
| Syto9 | UL | 0 | 0.00 | 0.00 | Syto9 | UL | 0 | 0.00 | 0.00 |
| Total Events 50000 | UR | 1 | 0.01 | 0.00 | Total Events 50000 | UR | 0 | 0.00 | 0.00 |
| Gated Events 6873 | LL | 284 | 4.13 | 0.57 | Gated Events 5785 | LL | 163 | 2.82 | 0.33 |
|  | LR | 6588 | 95.85 | 13.18 |  | LR | 5622 | 97.18 | 11.24 |
| FixC 30 cycles | Quad | Events | % Gated | % Total | FixD 30 cycles | Quad | Events | % Gated | % Total |
| Syto9 | UL | 0 | 0.00 | 0.00 | Syto9 | UL | 0 | 0.00 | 0.00 |
| Total Events 50000 | UR | 0 | 0.00 | 0.00 | Total Events 50000 | UR | 0 | 0.00 | 0.00 |
| Gated Events 7175 | LL | 733 | 10.22 | 1.47 | Gated Events 8726 | LL | 1845 | 21.14 | 3.69 |
|  | LR | 6442 | 89.78 | 12.88 |  | LR | 6881 | 78.86 | 13.76 |
| S 0 cycles | Quad | Events | % Gated | % Total |  |  |  |  |  |
| Syto9 | UL | 0 | 0.00 | 0.00 |  |  |  |  |  |
| Total Events 50000 | UR | 1 | 0.03 | 0.00 |  |  |  |  |  |
| Gated Events 3081 | LL | 1331 | 43.20 | 2.66 |  |  |  |  |  |
|  | LR | 1749 | 56.77 | 3.50 |  |  |  |  |  |
| S 30 cycles | Quad | Events | % Gated | % Total |  |  |  |  |  |
| Syto9 | UL | 0 | 0.00 | 0.00 |  |  |  |  |  |
| Total Events 50000 | UR | 2 | 0.04 | 0.00 |  |  |  |  |  |
| Gated Events 5114 | LL | 690 | 13.49 | 1.38 |  |  |  |  |  |
|  | LR | 4422 | 86.47 | 8.84 |  |  |  |  |  |

TABLE 12

| A 0 cycles | Quad | Events | % Gated | % Total | B 0 cycles | Quad | Events | % Gated | % Total |
|---|---|---|---|---|---|---|---|---|---|
| Syto9 | UL | 0 | 0.00 | 0.00 | Syto9 | UL | 0 | 0.00 | 0.00 |
| Total Events 50000 | UR | 1 | 0.01 | 0.00 | Total Events 50000 | UR | 2 | 0.01 | 0.00 |
| Gated Events 19549 | LL | 566 | 2.90 | 1.13 | Gated Events 16148 | LL | 5142 | 31.84 | 10.28 |
|  | LR | 18982 | 97.10 | 37.96 |  | LR | 11002 | 68.13 | 22.00 |
| A 15 cycles | Quad | Events | % Gated | % Total | B 15 cycles | Quad | Events | % Gated | % Total |
| Syto9 | UL | 0 | 0.00 | 0.00 | Syto9 | UL | 0 | 0.00 | 0.00 |
| Total Events 50000 | UR | 1 | 0.01 | 0.00 | Total Events 50000 | UR | 2 | 0.01 | 0.00 |
| Gated Events 15919 | LL | 59 | 0.37 | 0.12 | Gated Events 16803 | LL | 3730 | 22.20 | 7.46 |
|  | LR | 15859 | 99.62 | 31.72 |  | LR | 13071 | 77.79 | 26.14 |
| A 30 cycles | Quad | Events | % Gated | % Total | B 30 cycles | Quad | Events | % Gated | % Total |
| Syto9 | UL | 0 | 0.00 | 0.00 | Syto9 | UL | 0 | 0.00 | 0.00 |
| Total Events 50000 | UR | 5 | 0.03 | 0.01 | Total Events 50000 | UR | 5 | 0.03 | 0.01 |
| Gated Events 15707 | LL | 1563 | 9.95 | 3.13 | Gated Events 14533 | LL | 1431 | 9.85 | 2.86 |
|  | LR | 14139 | 90.02 | 28.28 |  | LR | 13097 | 90.12 | 26.19 |

The results of the flow cytometry (Quadrant: LR among the 4 quadrants, i.e., comparison of the numbers of bacterial cells of *Enterobacter sakazakii* before and after PCR using the number of SYTO9+ of the bacterium as the index) shown in Table 11 (also Table 12) suggest that even when the bacterial cells were fixed by using each fixation solution or without fixation (S) beforehand, namely, the bacterial chromosomal DNA was fixed in the cells, and then PCR thermal cycle was repeated for 30 times in the presence of the pretreatment agent, most of the bacterial cells were not lysed, but maintained the morphology, and the chromosomes were retained in the cells. Further, although presence of the target gene amplified product also in the PCR reaction mixture supernatant was suggested by the electrophoresis images (FIG. 14), the Ct values determined in the real-time PCR indicated under the gel images in FIG. 14 were observed for only the samples obtained with the fixation solution B and without fixation (S), and Ct value was not observed in real-time PCR with the other fixation solutions.

Figure 15:
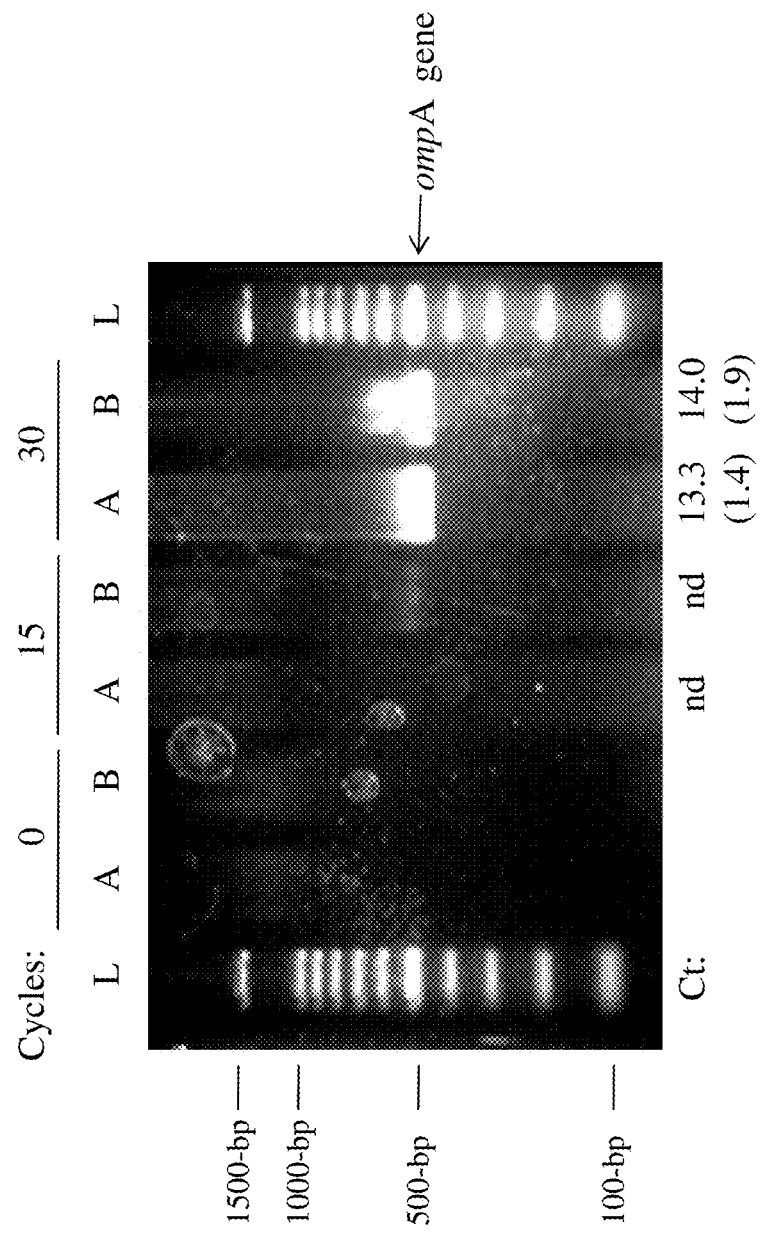

It may be considered that this is because, in the cases of the fixation solutions A, C and D, the fixation degree between the chromosome and the cell wall was high, therefore the thermal denaturation in PCR (95° C.) was not favorably attained, thus the chromosomal DNA could not become single strands, and therefore adhesion of primers to the chromosome became poor, but if the results of the similar experiment (30 cycles) targeting the ompA gene (469 bp) shown in FIG. 15 are taken into consideration, the Ct values determined in the real-time PCR and band intensities obtained with the fixation solutions A and B did not show significant difference, and therefore the above hypothesis is denied.

That is, it is considered that the small amounts of the target gene amplified products in the PCR reaction mixture supernatants obtained with the fixation solution A, C and D shown in FIG. 14 were provided because although the PCR reaction itself favorably advanced by using the chromosome harbored by the bacterial cells as a template, the gene products were 5 times longer than that of FIG. 15 (2450 bp), and as a result, flowing out of the gene products amplified in the cells into the external solution was suppressed. If this hypothesis is correct, the gene amplified product of 2450 bp should be detected also in the bacterial cells of *Enterobacter sakazakii* after PCR. This was verified in Example 8. As discussed above, it can be concluded that even if a treatment for fixing the bacterial chromosome in the cells to inhibit flowing out of the chromosome into the external solution was performed beforehand, substantially 100% of the bacterial cells maintained the bacterial morphology, and the chromosome was maintained in the cells even after repeating a PCR thermal cycle 50 times, so long as it was performed in the presence of the pretreatment agent, but in spite of that, the reactions of PCR advanced, and the PCR amplified product existed also in the external solution, and therefore the reactions of PCR occurred mainly in the bacterial cells. Further, as shown in Example 8 mentioned below, a part of the PCR product existed also in the cells under the aforementioned conditions.

Example 8

In Examples 4 to 7, it was suggested that the PCR in the presence of the pretreatment agent possibly occurred in the bacterial cells, i.e., in situ PCR possibly occurred. In situ PCR (for example, Gerard J. et al., American Journal of Pathology, 139: 847-854, 1991) is a technique for detecting and quantifying a gene such as the HPV gene incorporated into a chromosomal DNA in human cells, in which before the detection and quantification, human immunocytes are fixed with such a fixation solution as mentioned in Example 7 to crosslink the chromosomal DNA and human cell membrane proteins, and the cells are treated with a protease for a short period of time, or cell membranes of the human immunocytes are treated by microwave irradiation.

This technique is a technique of placing a solution for PCR on fixed human immunocytes to induce PCR amplification reactions within the human immunocytes, with which even a PCR product of about 500 bp does not flow out of the cells. Since the PCR product does not flow out of the cells, if the reactions of PCR are suspended in an early stage of less than 5 to 10 cycles, it can be a technique enabling not only detection of a gene in cells, but also estimation of the number of incorporated gene.

If PCR in the presence of the pretreatment agent according to the present invention is in situ PCR, a part of the amplified product may remain also in the bacterial cells, and in this example, an experiment was performed in order to verify it. In Example 7, in particular, although the chromosomal DNA of *Enterobacter sakazakii* was probably crosslinked with cell wall proteins with the fixation solution B, there was observed a tendency that the amplified product of PCR in the presence to the pretreatment agent more flew out into the external solution as compared with the case of using the other fixation solutions, and a phenomenon similar to that observed with the technique of the present invention not using any fixation solution (technique using no fixation (S)).

Therefore, the researches were focused on the fixation solution B and no fixation (S) mentioned in Example 7, and it was examined whether the PCR amplified product would partially remain in the bacterial cells even when a large amount of the PCR amplified product flew out into the external solution.

1. Experimental Methods

Two portions of 500 µl of a culture broth of the *Enterobacter sakazakii* ATCC51329 strain ($4.3 \times 10^8$ cells/ml) in which the cells were proliferated overnight were prepared, and subjected to refrigerated centrifugation (3000×g, 10 minutes, 4° C.), the supernatants were removed, then 500 µl of the fixation solution B (methanol/acetic acid=3/1) was added to each pellet, the mixture was incubated overnight at 4° C. to crosslink the chromosomal DNA in the bacterial cells and the cell wall proteins, and thereby DNA was fixed in the cells beforehand. As a control, a sample for which the fixation was not performed was prepared by using 500 µl of physiological saline instead of the fixation solution B. The same methods as those of Example 7 were used thereafter, and the sample was finally diluted 10 times to obtain 250 µl of a suspension of *Enterobacter sakazakii* in physiological saline. The estimated cell density of *Enterobacter sakazakii* in the suspension was about $3.5 \times 10^7$ cells/ml. This suspension was used in a volume of 2.5 µl as a sample for PCR amplification, and added to 12.25 µl of the pretreatment agent solution mentioned in Table 5 (provided that the volume of sterilized water was changed to 2.7 µl), and 12.75 µl of the PCR buffer for detection of gram-negative bacteria mentioned below was added to the mixture to perform PCR under the following conditions. At the time of PCR, portions in a volume of 27.5 µl were prepared in a number of 20 for each of the sample obtained with the fixation solution and the control sample. As the primers, the forward primer 16S_1234F for 16S rRNA gene detection (SEQ ID NO: 3), and the reverse primer 23S_1703R for 23S rRNA gene detection (SEQ ID NO: 4) mentioned in Example 3 were used.

After completion of PCR, the 20 portions of the PCR reaction solution for each fixation solution were combined into one, and subjected to refrigerated centrifugation (3000× g, 10 minutes, 4° C.). The supernatant was collected in a volume of 5 µl and used in 0.8% agarose gel electrophoresis, and the remaining supernatant was discarded. The pellet was washed twice with 500 µl of physiological saline, and DNA was extracted by using QuickGene SP kit DNA tissue.

Separately, two 500-µl portions of culture broth in which the cells were proliferated overnight ($4.3 \times 10^8$ cells/ml) were prepared, and subjected to refrigerated centrifugation (3000×g, 10 minutes, 4° C.), the supernatants were removed, then 500 µl of the fixation solution B (methanol/acetic acid=3/1) was added to each pellet, and the mixture was incubated overnight at 4° C. The cells were washed 3 times with 500 µl of physiological saline, and DNA was extracted and purified by using QuickGene SP kit DNA tissue (Fuji Photo Film Co., Ltd.). As a control, a sample in which the fixation was not performed was prepared by using 500 µl of physiological saline instead of the fixation solution B. According to the above description, the cell count in the case of applying only washing immediately after the fixation and directly extracting DNA from the pellet was, since the sample was subjected to centrifugation 4 times in total, $4.3 \times 10^8 \times 0.5 \times 0.41 = 0.9 \times 10^8$ cells, but the bacterial count used for PCR was calculated to be about $3.5 \times 10^7$ cells/ml $\times$ 2.5 µl $\times 20 = 1.8 \times 10^6$ cells in terms of estimated cell density, and if it is taken into consideration that the sample was further subjected to centrifugation 3 times thereafter, it is estimated to be $0.9 \times 10^6$ cells.

Since the bacterial number used for the DNA extraction step in the sample before PCR was 100 times larger than that in the sample after PCR for each case, in order to use them in the same cell number, 20 portions each in a volume of 2.5 µl ($=1.8 \times 10^6$ cells) of a physiological saline suspension of *Enterobacter sakazakii* ($3.5 \times 10^7$ cells/ml) were prepared (fixation solution B and control S), combined into one without performing PCR, then washed 3 times in total by centrifugation, and used for the DNA extraction.

Further, even if the long PCR amplified product of about 2450 bp was confirmed within the bacterial cells of *Enterobacter sakazakii* by the aforementioned examination, since the PCR amplified product existed in the external solution as shown in FIG. 14 or 15 when PCR was performed in the presence of the pretreatment agent, it may be misunderstood that the PCR amplified product in the external solution might adsorb on the bacterial cell walls of *Enterobacter sakazakii*, as if the PCR amplified product apparently existed in the inside of the cells. Therefore, the following experiment was additionally performed.

Samples were prepared in a number of 20 by adding 2.5 µl of a DNA aqueous solution containing 0.44 ng of DNA (440 pg, the amount of chromosomal DNA contained in $8.8 \times 10^4$ cells) purified from the *Enterobacter sakazakii* ATCC51329 strain to each PCR tube, adding a pretreatment agent solution as in the aforementioned case, and then adding a PCR buffer to a total volume of 27.5 µl, and PCR was performed with each of them under the conditions shown below. Then, the contents of the 20 PCR tubes were combined into one, 50 µl of a $3.5 \times 10^7$ cells/ml physiological saline suspension of *Enterobacter sakazakii* (treated with the fixation solution B or with no fixation, and washed 3 times according to the method of Example 7) was added to the combined reaction solution, the mixture was sufficiently mixed, and subjected to refrigerated centrifugation (3000×g, 10 minutes, 4° C.) to remove the supernatant, and the pellet was washed twice and used for DNA extraction.

Composition of PCR Buffer:
a) 16S_1234F (10 pmol/µl): 2 µl
b) 23S_1703R (10 pmol/µl): 2 µl
c) Ex-Taq (5 U/µl, Takara-Bio): 0.25 µl (containing 0.5% Tween 20, 0.5% Nonidet P-40, and 50% glycerol)
d) 10×Ex-Taq Buffer (Takara-Bio): 2.5 µl
e) dNTP mixture (Takara-Bio): 2 µl
f) 10×SYBR Green I (BMA): 4 µl Real-time PCR was performed according to the following PCR thermal cycle conditions by using a real-time PCR apparatus (iCycler iQ, Bio-Rad, Hercules, Calif.).
1) 4° C. for 3 minutes (1 cycle)
2) 95° C. for 15 seconds; 60° C. for 20 seconds; 72° C. for 3 minutes (30 cycles)
3) 95° C. for 3 minutes (1 cycle)

Then, according to the protocol of the melt analysis of the PCR amplified product (temperature was raised at intervals of 0.1° C. from 60° C., each temperature was maintained for 8 seconds, and this procedure was repeated 350 times in total up to the final temperature of 95° C.), the melting temperature of the PCR amplified product was measured.

2. Results

Figure 16:
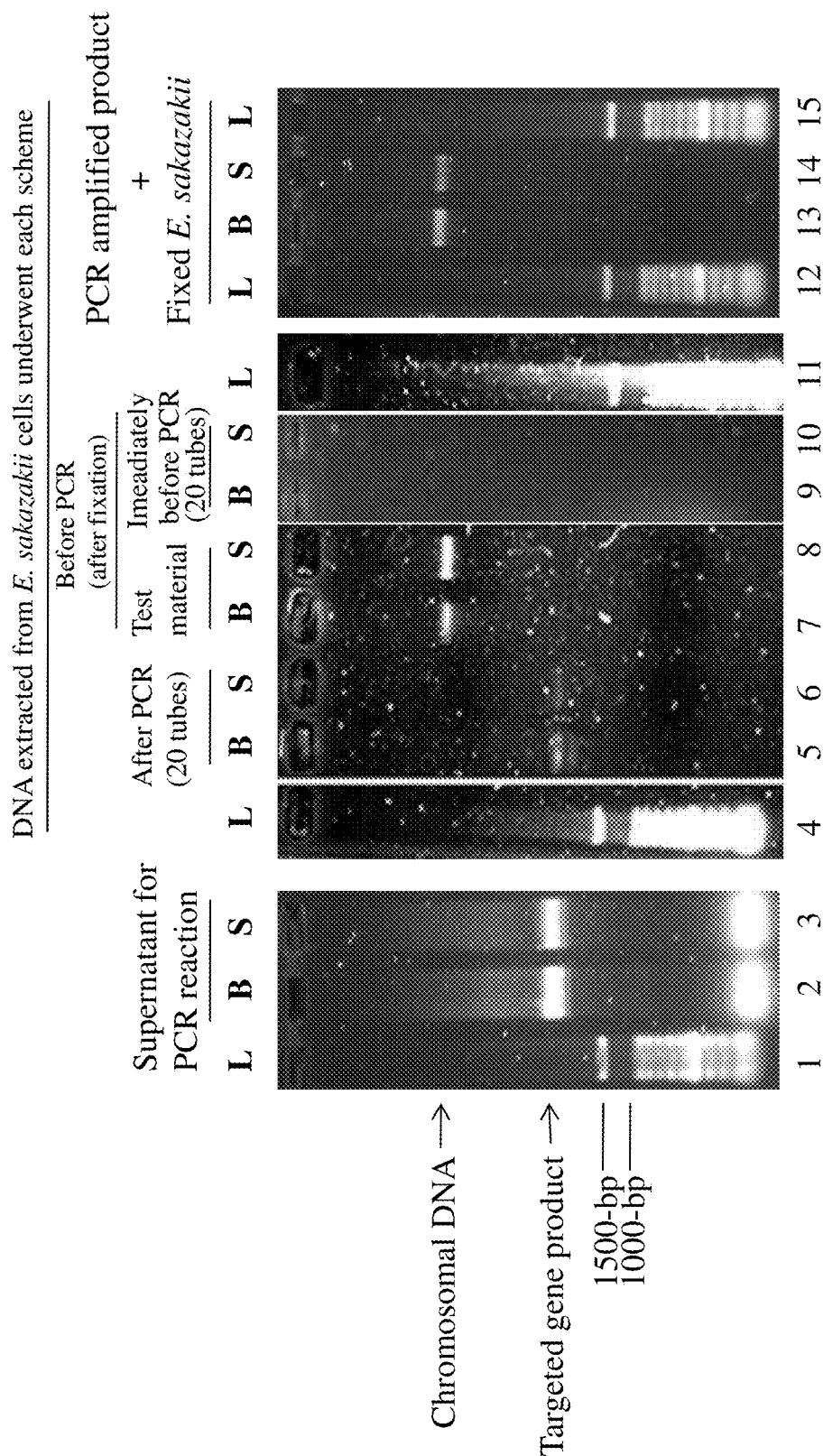

The results are shown in FIG. 16. The results of electrophoresis of supernatants of reaction mixtures obtained in PCR performed in the presence of the pretreatment agent (16S-23S: 2450 bp) with cells of *Enterobacter sakazakii* fixed with the fixation solution B or not fixed are shown in the lanes 2 and 3, the results of electrophoresis of DNA obtained by DNA extraction from the pellet obtained after the PCR mentioned above and washed twice are shown in the lanes 5 and 6, the results of electrophoresis of DNA directly extracted from the fixed or not fixed *Enterobacter sakazakii* cells, which were the test materials of this experiment, are shown in the lanes 7 and 8, the results of electrophoresis of DNA extracted from the fixed or not fixed *Enterobacter sakazakii* cells before they were used for the reactions of PCR are shown in the lanes 9 and 10, and the results of electrophoresis of DNA extracted from the *Enterobacter sakazakii* cells washed twice after addition of the PCR amplified product prepared beforehand are shown in the lanes 13 and 14, respectively.

As shown by the results of the lanes 13 and 14, it was demonstrated that even if the PCR gene product (2450 bp) adsorbed to *Enterobacter sakazakii* bacterial cell wall outer membranes etc. from the external solution side, the PCR gene product could be removed from the bacterium by washing twice for both the fixed and non-fixed cells. Therefore, the possibility of incorrect interpretation that the PCR gene product that might adsorb on the cell wall outer surfaces was regarded as the PCR gene product remained in the cells was eliminated. Further, by taking into consideration that a fragment estimated to be the PCR reaction product was detected in the lanes 5 and 6 indicating the results for DNA extracted from the cells of which pellet was washed twice after PCR, and that the fragment was not the PCR gene product that might adsorb on the outside of the cell wall as seen from the results of the lanes 13 and 14, the PCR gene product of the lanes 5 and 6 is highly possibly the PCR gene product remained in the cells and then extracted. Further, even if the concentrations of the PCR gene product in the external solution and in the cells became the same, because the cells were bacterial cells of which cell walls were injured, and thus the PCR gene product was in a state that it could freely pass through the cell walls, the volume of the external solution was about $10^{10}$ times larger than the volume of the cells, and the amount of the PCR gene product in the external solution should also be about $10^{10}$ times larger than that in the cells, that is, $1/10^{10}$ of the amount in the external solution should be distributed in the cells. However, on the basis of comparison of the band intensities of the lanes 2, 3, 5 and 6, it cannot be considered that the amount of the PCR product remained in the cells was the $1/10^{10}$ amount. That is, it was suggested that the PCR occurred in the method of the present invention might possibly be in situ PCR. As seen from the results of the lanes 7 and 8, the chromosomal DNA was detected from both the fixed and non-fixed *Enterobacter sakazakii* bacterial cells used as the test materials, but any band of the chromosomal DNA was not obtained in the lanes 5, 6, 9 and 10. This difference was probably provided by the difference of the cell number of the *Enterobacter sakazakii* bacterial cells used for the DNA extraction, specifically, the cell number of $0.9 \times 10^6$ cells was highly possibly insufficient for the DNA extraction, whereas in the lanes 7 and 8 for the test materials, the cell number was in fact as high as 0.9×10⁸ cells.

Example 9

The cells of *Enterobacter sakazakii* were subjected to a boiling treatment in physiological saline or in the presence of the pretreatment agent, and it was investigated how much the *Enterobacter sakazakii* chromosomal DNA was flown out into each supernatant depending on the treatment time.

1. Experimental Methods

Cells in a culture broth of the *Enterobacter sakazakii* ATCC51329 strain (1.1×10⁹ cells/ml) in which the cells were proliferated overnight were washed, and diluted 10 times with physiological saline, and the suspension was subjected to refrigerated centrifugation (3000×g, 10 minutes, 4° C.) to collect a pellet once, an equal volume (500 µl) of physiological saline or a pretreatment agent solution having the composition shown in Table 5 was added to the pellet, and the cells were sufficiently suspended. Then, the suspension was heated with boiling water for 0 to 5 minutes, and after the heating, immediately cooled. Each suspension immediately after the heating in a volume of 5 µl and a supernatant obtained by refrigerated centrifugation of each suspension in a volume of 5 µl were subjected to electrophoresis on 0.8% agarose gel, respectively.

2. Results

Figure 17:
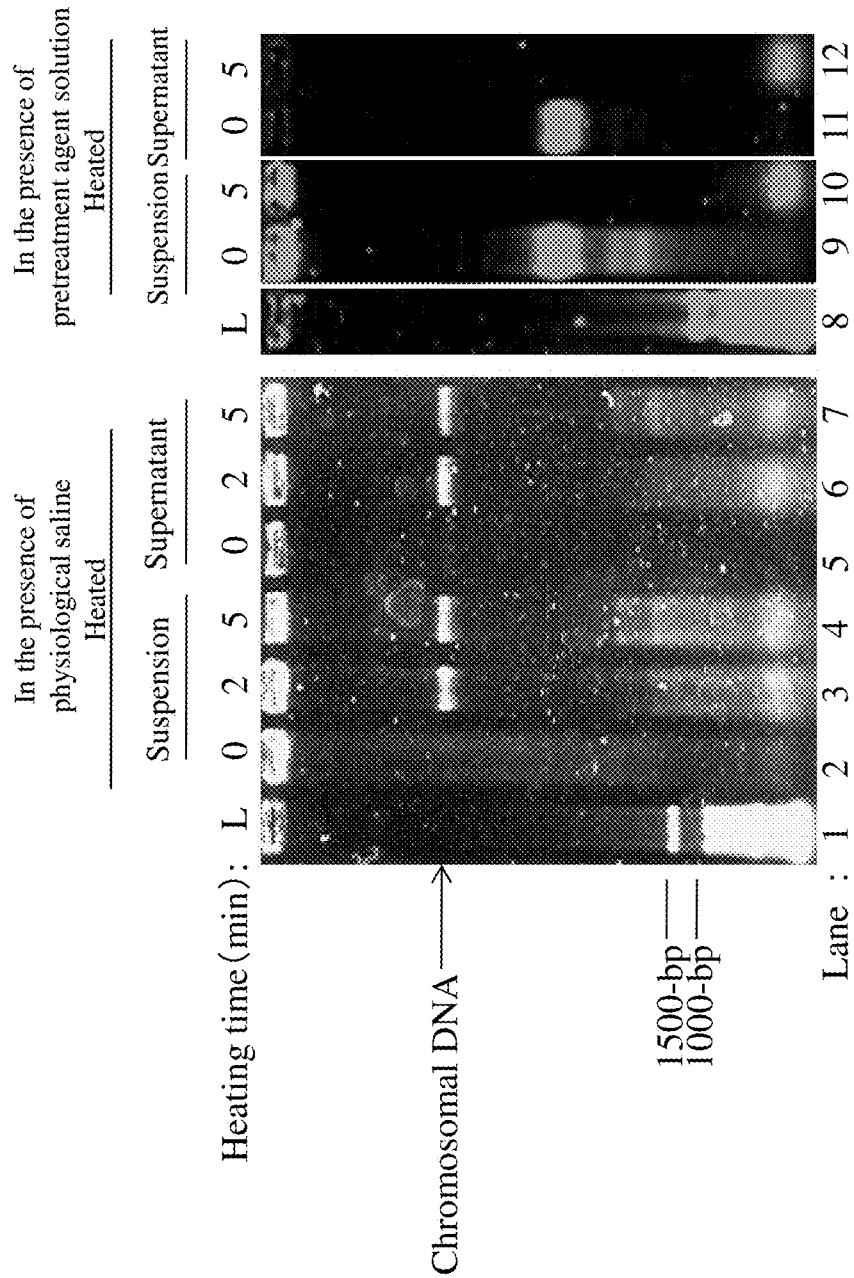

In FIG. 17, there are shown degrees of flowing out into the supernatant of the chromosomes of *Enterobacter sakazakii* subjected to the heat treatment in physiological saline or in the presence of the pretreatment agent using boiling water. First, as for the results of the lanes 2 and 9, although the cells were not heated, the presence of a trace amount of the chromosomal DNA was already suggested, but it is considered that this was because the cells in the culture broth in which the cells were proliferated overnight reached the resting stage, therefore a part of dead cells were lysed, and the chromosomal DNA thereof flew out into the external solution. Therefore, such a trace amount of the chromosomal DNA was ignored in the evaluation. Although it was estimated that DNA flew out in physiological saline from the bacterial cells of *Enterobacter sakazakii* due to the heating, any band of the chromosomal DNA was not detected for the suspension and the supernatant in the presence of the pretreatment agent even after boiling for 5 minutes. However, when evaluation was made on the basis of observation of the wells of the lanes 10 and 12, a band was observed in the well in the case of the suspension, but any band was not observed for the supernatant, and it was revealed that the chromosomal DNA did not flow out of the bacterial cells in the presence of the pretreatment agent, but remained in the cells. On the other hand, bands were also observed in the wells for the supernatants of physiological saline (lanes 5, 6 and 7), and it is considered that they were derived from a part of dead cells of *Enterobacter sakazakii* collected in the supernatant after centrifugation, of which specific gravity decreased due to the boiling. The results shown in Table 6 or FIG. 12 also support this estimation. From the above results, it was suggested that, although the conditions differed from those of the repetition of the PCR thermal cycle to be precise, it is more difficult for DNA to flow out of the bacterial cells in the presence of the pretreatment agent even when the cells are subjected to a heat treatment.

INDUSTRIAL APPLICABILITY

According to the method of the present invention, live cells of a microorganism can be detected with high sensitivity by distinguishing them from dead cells or injured cells. The present invention enables simple and quick distinction of live cells, injured cells and dead cells of a microorganism in foodstuffs, biological samples, swab samples and environments such as industrial water, environmental water and wastewater, based on the nucleic acid amplification method. The method and kit of the present invention can be used for voluntary investigation, and are advantageous also in an economical point of view.

According to a preferred embodiment of the present invention, it can also be applied to sanitation inspection of various foodstuffs containing 5 $\log_{10}$ cells/ml or more of injured cells or dead cells of *Escherichia coli*, or diagnosis of child bacteriemia in which *Escherichia coli* circulates in blood.

Further, according to a preferred embodiment of the present invention, only live cells of coliform bacteria including Enterobacteriaceae bacteria can be detected from foodstuffs with high sensitivity (1 CFU/2.22 ml of milk), and more quickly (7 hours and 30 minutes) compared with the regulated method (Food Sanitation Law/Ministerial Ordinance concerning the Ingredient Standards for Milk and Dairy Products), therefore use thereof is expected for determination before factory shipments after manufacture in various food factories represented by milk manufacturing factories, and it is assumed to be highly industrially useful.

Furthermore, the present invention enables quick detection and quantification of only live microorganisms at a low concentration, for microorganisms including not only coliform bacteria and Enterobacteriaceae bacteria, but also various bacteria including pathogenic bacteria, viruses, and so forth, and therefore it can be applied to various sanitation inspections, clinical tests, process control, and so forth.

What is claimed is:

1. A kit for detecting live cells of a microorganism in a test sample by distinguishing the live cells from dead cells or injured cells by a nucleic acid amplification method, which comprises the following components:
   1) an agent capable of covalently binding to DNA or RNA of the microorganism by irradiation with light having a wavelength of 350 nm to 700 nm;
   2) an agent for suppressing a nucleic acid amplification inhibitory substance, magnesium salt, and either one of an organic acid salt and a phosphoric acid salt; and
   3) a primer or primers for amplifying a target region of the DNA or RNA of the microorganism to be detected by a nucleic acid amplification method,
   wherein the agent for suppressing a nucleic acid amplification inhibitory substance is one or more selected from the group consisting of albumin, dextran, T4 gene 32 protein, acetamide, betaine, dimethyl sulfoxide, formamide, glycerol, polyethylene glycol, soybean trypsin inhibitor, α2-macroglobulin, tetramethylammonium chloride, lysozyme, phosphorylase and lactate dehydrogenase.

2. The kit according to claim 1, which further comprises a surfactant.

3. The kit according to claim 1, which further comprises an enzyme having an activity of decomposing cells other than that o the microorganism, a colloidal particle of a protein, a lipid or a saccharide existing in the test sample.

4. The kit according to claim 1, wherein the nucleic acid amplification method is PCR, RT-PCR, LAMP, SDA, LCR, TMA, TRC, HC or DNA microarray method.

5. The kit according to claim 1, wherein the agent capable of covalently binding to DNA or RNA by irradiation with light having a wavelength of 350 nm to 700 nm is selected from the group consisting of ethidium monoazide, ethidium diazide, propidium monoazide, psoralen, 4, 5', 8-trimethylpsoralen and 8-methoxypsoralen.

6. The kit according to claim 1, wherein the organic acid salt is selected from the group consisting of an acetic acid salt, a propionic acid salt and a citric acid salt.

7. The kit according to claim 1, wherein the phosphoric acid salt is a pyrophosphoric acid salt.

8. The kit according to claim 3, wherein the enzyme is selected from the group consisting of a protein-degrading enzyme, a lipid-degrading enzyme and a saccharide-degrading enzyme.

9. A kit for detecting live cells of a microorganism in a test sample by distinguishing the live cells from dead cells by a nucleic acid amplification method, which comprises the following components:
   1) an agent capable of covalently binding to DNA or RNA of the microorganism by irradiation with light having a wavelength of 350 nm to 700 nm;
   2) an agent for suppressing a nucleic acid amplification inhibitory substance, magnesium salt, and either one of an organic acid salt and a phosphoric acid salt; and
   3) a primer or primers for amplifying a target region of the DNA or RNA of the microorganism to be detected by a nucleic acid amplification method.

* * * * *

SEQUENCE LISTING

```
<160> NUMBER OF SEQ ID NOS: 10

<210> SEQ ID NO 1
<211> LENGTH: 16
<212> TYPE: DNA
<213> ORGANISM: Artificial sequence
<220> FEATURE:
<223> OTHER INFORMATION: primer 16S_10F

<400> SEQUENCE: 1 agtttgatcctggctc                                                    16

<210> SEQ ID NO 2
```

```
<211> LENGTH: 16
<212> TYPE: DNA
<213> ORGANISM: Artificial sequence
<220> FEATURE:
<223> OTHER INFORMATION: primer 16S_1500R

<400> SEQUENCE: 2 ggctaccttgttacga                                                    16

<210> SEQ ID NO 3
<211> LENGTH: 25
<212> TYPE: DNA
<213> ORGANISM: Artificial sequence
<220> FEATURE:
<223> OTHER INFORMATION: primer 16S_1234F

<400> SEQUENCE: 3 ctacaatggcgcatacaaagagaag                                           25

<210> SEQ ID NO 4
<211> LENGTH: 25
<212> TYPE: DNA
<213> ORGANISM: Artificial sequence
<220> FEATURE:
<223> OTHER INFORMATION: primer 23S_1703R

<400> SEQUENCE: 4 ccttctcccgaagttacggcaccat                                           25

<210> SEQ ID NO 5
<211> LENGTH: 19
<212> TYPE: DNA
<213> ORGANISM: Artificial sequence
<220> FEATURE:
<223> OTHER INFORMATION: primer hlyA-F

<400> SEQUENCE: 5 tgcaagtcctaagacgcca                                                 19

<210> SEQ ID NO 6
<211> LENGTH: 24
<212> TYPE: DNA
<213> ORGANISM: Artificial sequence
<220> FEATURE:
<223> OTHER INFORMATION: primer hlyA-R

<400> SEQUENCE: 6 cactgcatctccgtggtatactaa                                            24

<210> SEQ ID NO 7
<211> LENGTH: 22
<212> TYPE: DNA
<213> ORGANISM: Artificial sequence
<220> FEATURE:
<223> OTHER INFORMATION: primer ompA-F

<400> SEQUENCE: 7 ggatttaaccgtgaacttttcc                                              22

<210> SEQ ID NO 8
<211> LENGTH: 19
<212> TYPE: DNA
<213> ORGANISM: Artificial sequence
<220> FEATURE:
<223> OTHER INFORMATION: primer ompA-R

<400> SEQUENCE: 8
``` cgccagcgatgttagaaga                                                   19

<210> SEQ ID NO 9
<211> LENGTH: 22
<212> TYPE: DNA
<213> ORGANISM: Artificial sequence
<220> FEATURE:
<223> OTHER INFORMATION: primer MMS-F

<400> SEQUENCE: 9 gggatattgtcccctgaaacag                                                22

<210> SEQ ID NO 10
<211> LENGTH: 19
<212> TYPE: DNA
<213> ORGANISM: Artificial sequence
<220> FEATURE:
<223> OTHER INFORMATION: primer MMS-R

<400> SEQUENCE: 10 cgagaataagccgcgcatt                                                   19